US007062219B2

(12) United States Patent
Michnick et al.

(10) Patent No.: US 7,062,219 B2
(45) Date of Patent: *Jun. 13, 2006

(54) PROTEIN FRAGMENT COMPLEMENTATION ASSAYS FOR HIGH-THROUGHPUT AND HIGH-CONTENT SCREENING

(75) Inventors: Stephen William Watson Michnick, Westmount (CA); Ingrid Remy, Montreal (CA); Marnie MacDonald, Pleasanton, CA (US); Jane Lamerdin, Livermore, CA (US); Helen Yu, Mountain View, CA (US); John K. Westwick, San Ramon, CA (US)

(73) Assignee: Odyssey Thera Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/772,021

(22) Filed: Feb. 5, 2004

(65) Prior Publication Data

US 2004/0161787 A1    Aug. 19, 2004

Related U.S. Application Data

(63) Continuation-in-part of application No. 10/353,090, filed on Jan. 29, 2003, which is a continuation of application No. 10/154,758, filed on May 24, 2002, now Pat. No. 6,929,916, which is a continuation of application No. 09/499,464, filed on Feb. 7, 2000, now Pat. No. 6,428,951, which is a continuation of application No. 09/017,412, filed on Feb. 2, 1998, now Pat. No. 6,270,964.

(60) Provisional application No. 60/445,225, filed on Feb. 6, 2003.

(30) Foreign Application Priority Data

Jan. 31, 1997    (CA)    .................... 2196496

(51) Int. Cl.
*C12Q 1/00* (2006.01)
*C07K 14/00* (2006.01)
*C12N 15/11* (2006.01)

(52) U.S. Cl. .......................... 434/4; 530/350; 536/23.4
(58) Field of Classification Search .................... 434/4; 435/6; 530/350; 536/23.4
See application file for complete search history.

(56) References Cited

U.S. PATENT DOCUMENTS

| 6,270,964 | B1 * | 8/2001 | Michnick et al. | 435/6 |
| 6,294,330 | B1 * | 9/2001 | Michnick et al. | 435/6 |
| 6,428,951 | B1 * | 8/2002 | Michnick et al. | 435/4 |

OTHER PUBLICATIONS

Panayotou et al. The assembly of signaling complexes by receptor tyrosine kinases. BioEssays, vol. 15, No. 3 pp. 171-177 (1993).*
Ko et al. p53: puzzle and paradigm Genes and Development, vol. 10, pp. 1054-1072 (1996).*
Johnsson et al. Split ubiquitin as a sensor of protein interactions in vivo. Proc. Natl. Acad. Sci. USA vol. 91, pp. 10340-10344 (1994).*

* cited by examiner

*Primary Examiner*—John S. Brusca
(74) *Attorney, Agent, or Firm*—Issac A. Angres

(57) ABSTRACT

The present invention provides protein single-color and multi-color protein fragment complementation assays for drug discovery, in particular to identify compounds that activate or inhibit cellular pathways. Based on the selection of an interacting protein pair combined with an appropriate PCA reporter such as monomeric enzymes and fluorescent proteins, the assays may be run in high-throughput or high-content mode and may be used in automated screening of libraries of compounds. Methods are described for constructing such assays for one or more steps in a biochemical pathway; testing the effects of compounds from combinatorial, natural product, peptide, antibody, nucleic acid or other diverse libraries on the protein or pathway(s) of interest; and using the results of the screening to identify specific compounds that activate or inhibit the protein or pathway(s) of interest. The development of such assays provides for a broad, flexible and biologically relevant platform for drug discovery.

12 Claims, 24 Drawing Sheets

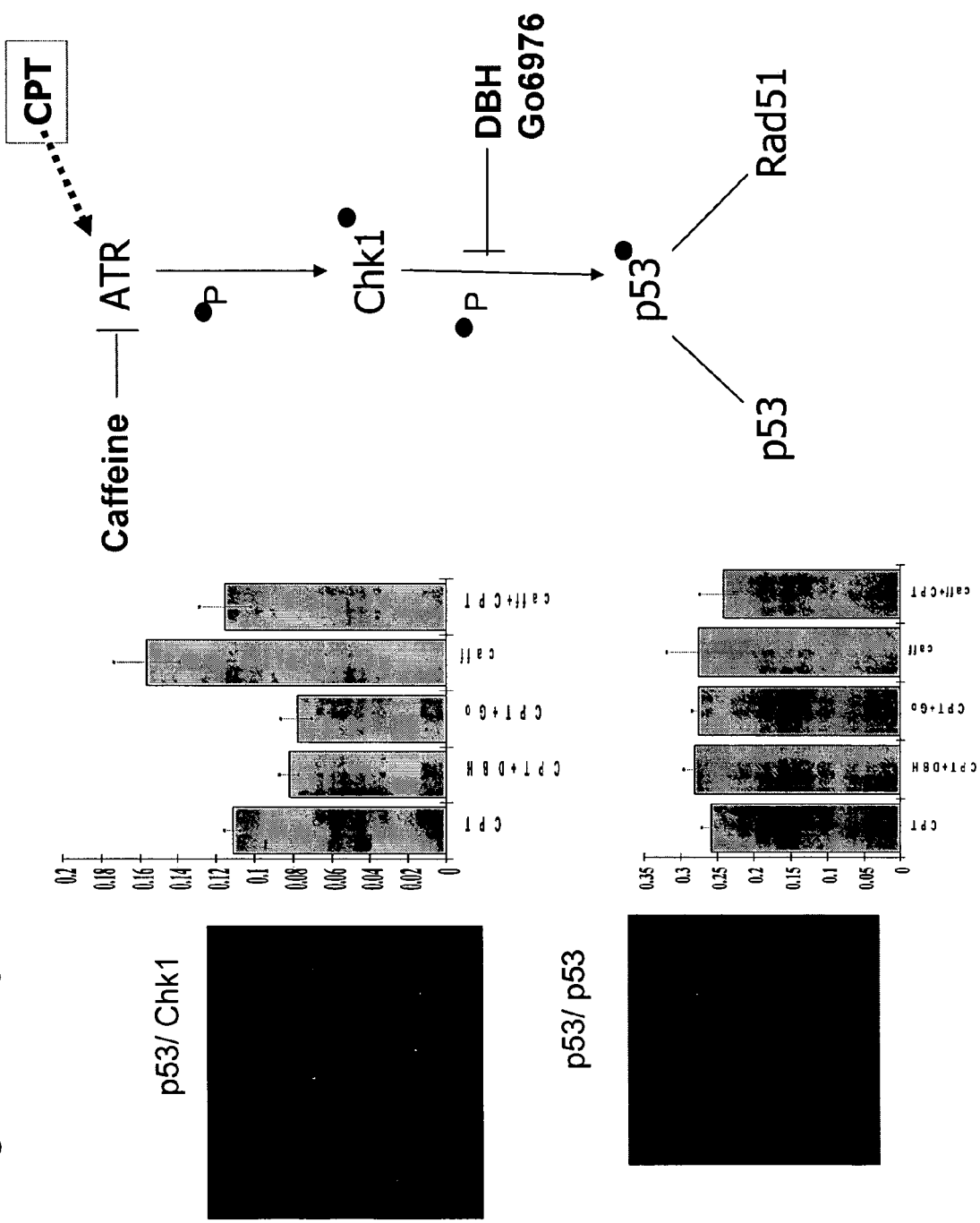
Fig. 2 Assays for the DNA damage response pathway

Fig. 3(A) A Luminescent PCA (RLuc PCA) for high-throughput screening (HTS)
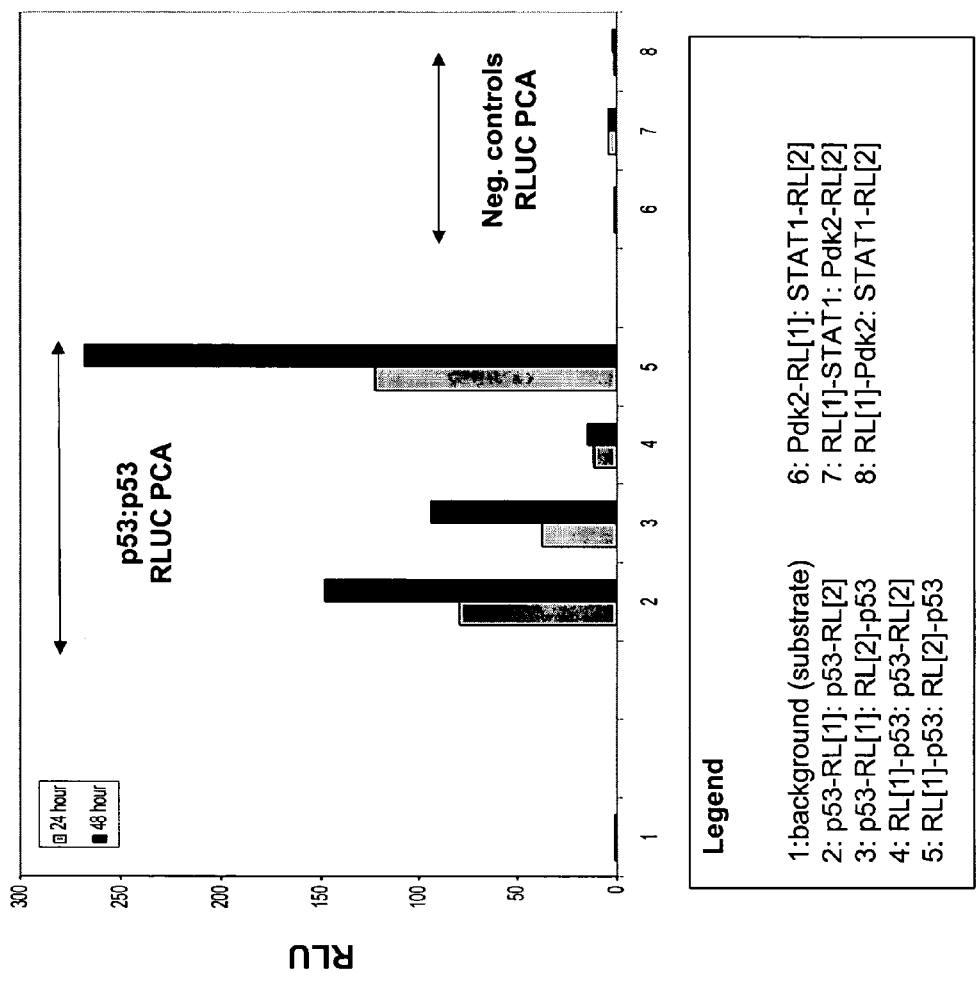

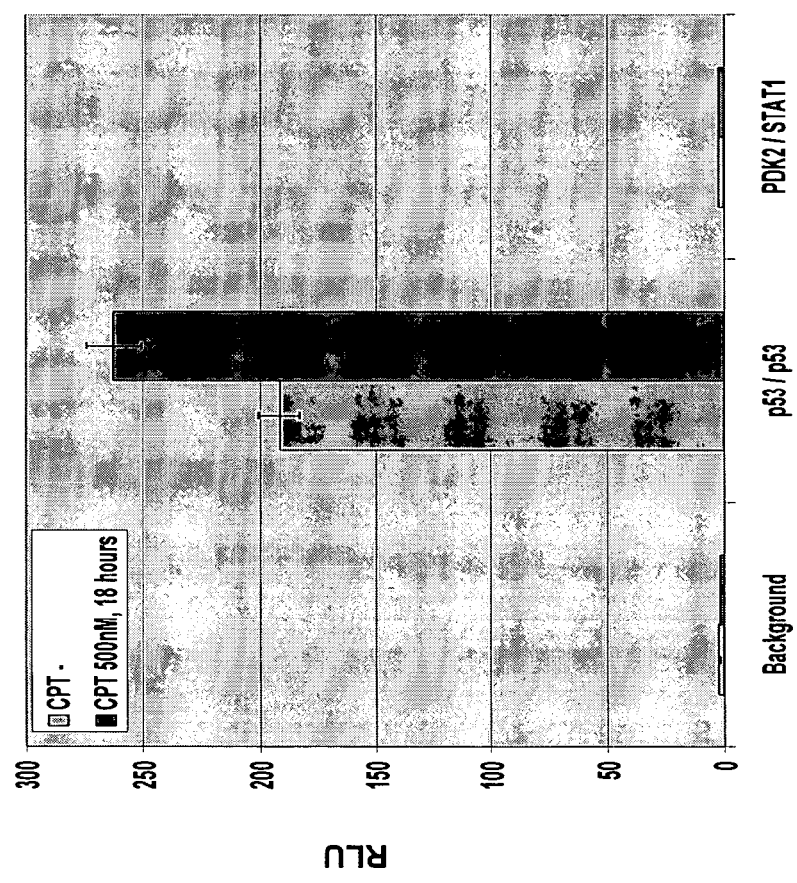
Fig. 3(B) Effect of camptothecin (CPT) treatment on p53/p53 (Renilla luciferase PCA)

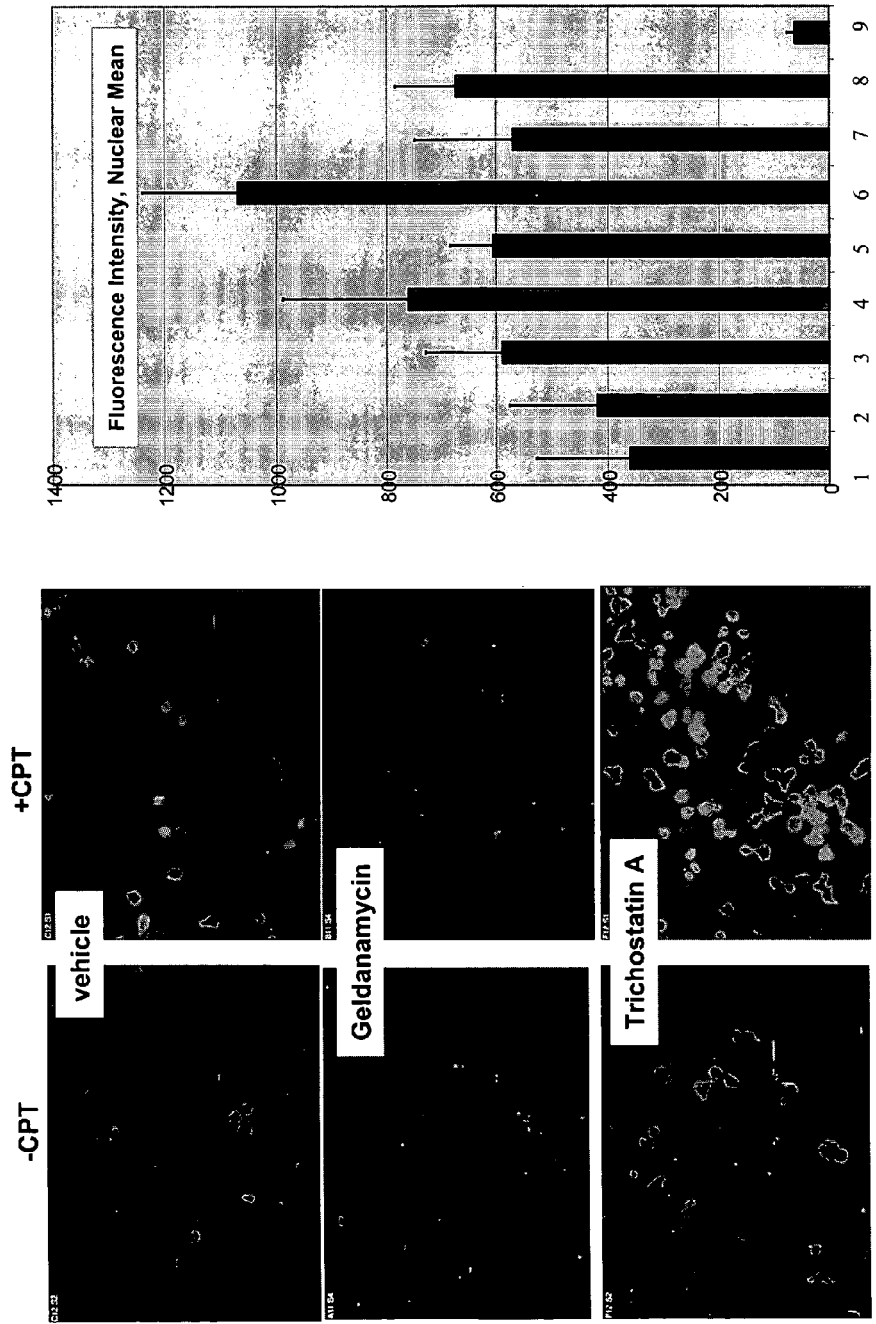
Fig. 4  IFP PCA demonstrating effects of drugs on p53/p53 in the presence and absence of camptothecin (CPT)

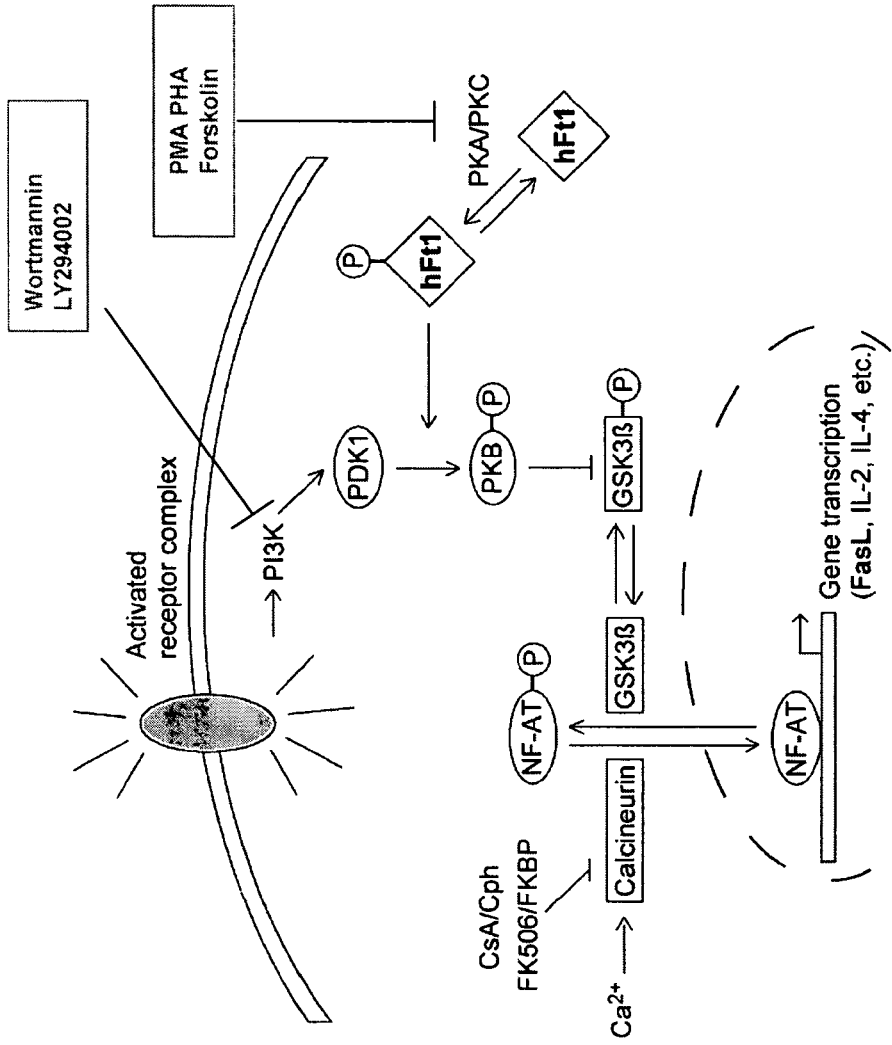
Fig. 5(A) PI3K pathway and the involvement of a novel interaction identified by PCA (hFt1/PKB)

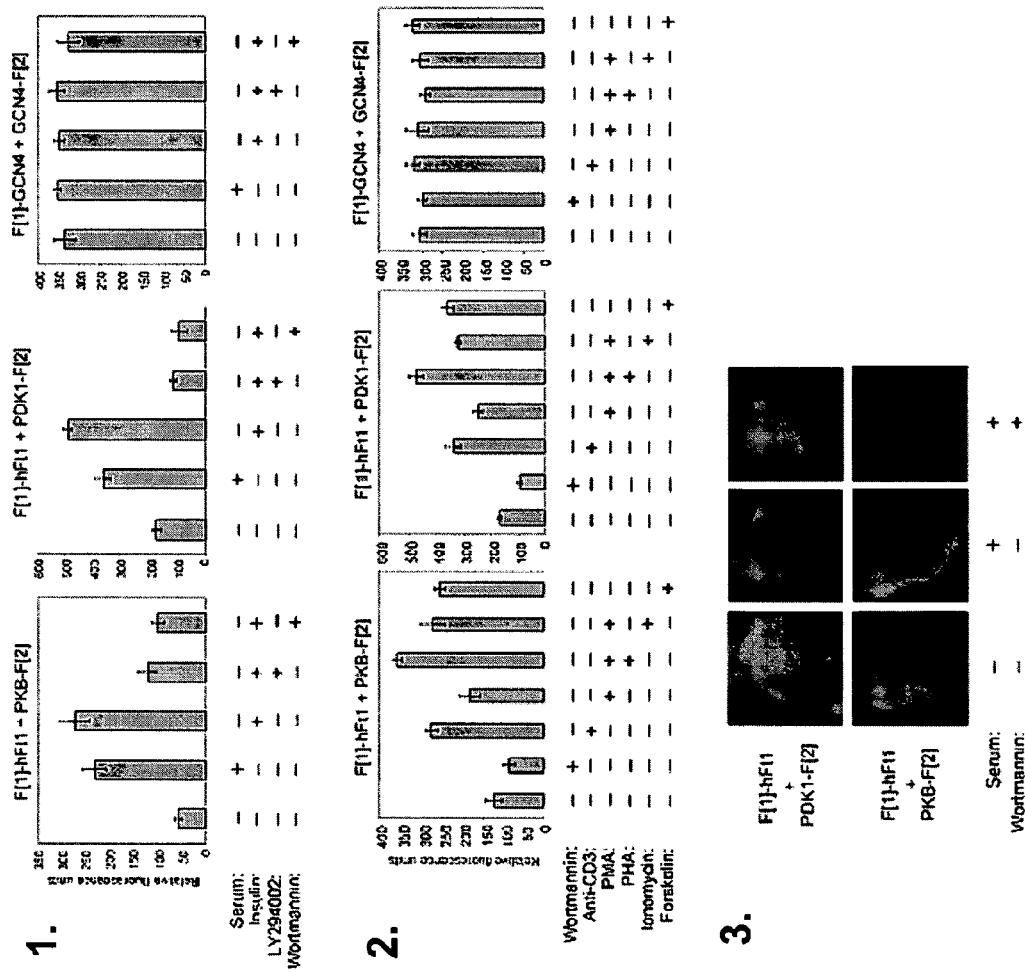
Fig. 5(B) Induction and inhibition of hFt1 complexes (GFP PCA)

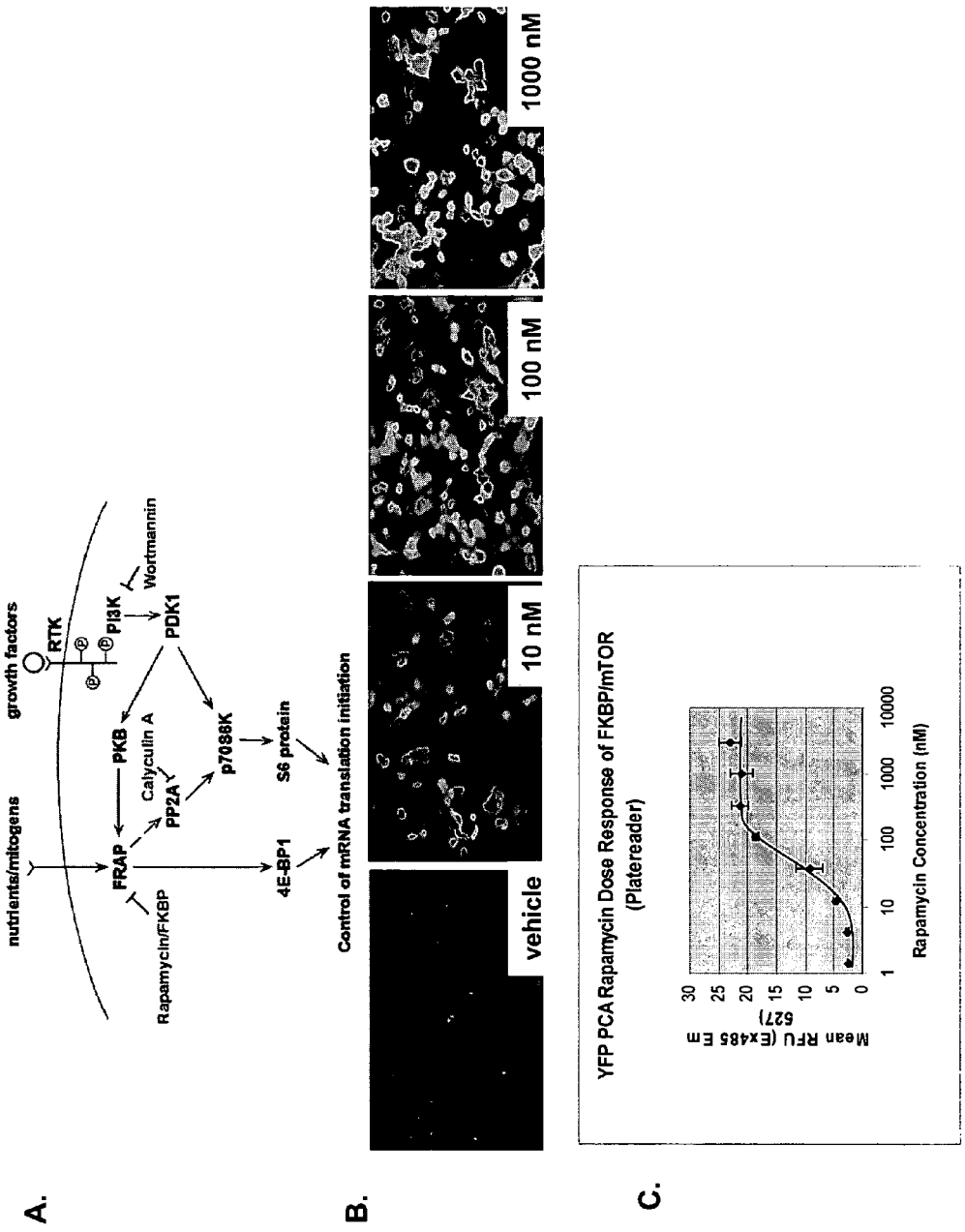
Fig. 6 A rapamycin-dependent HTS assay based on YFP PCA

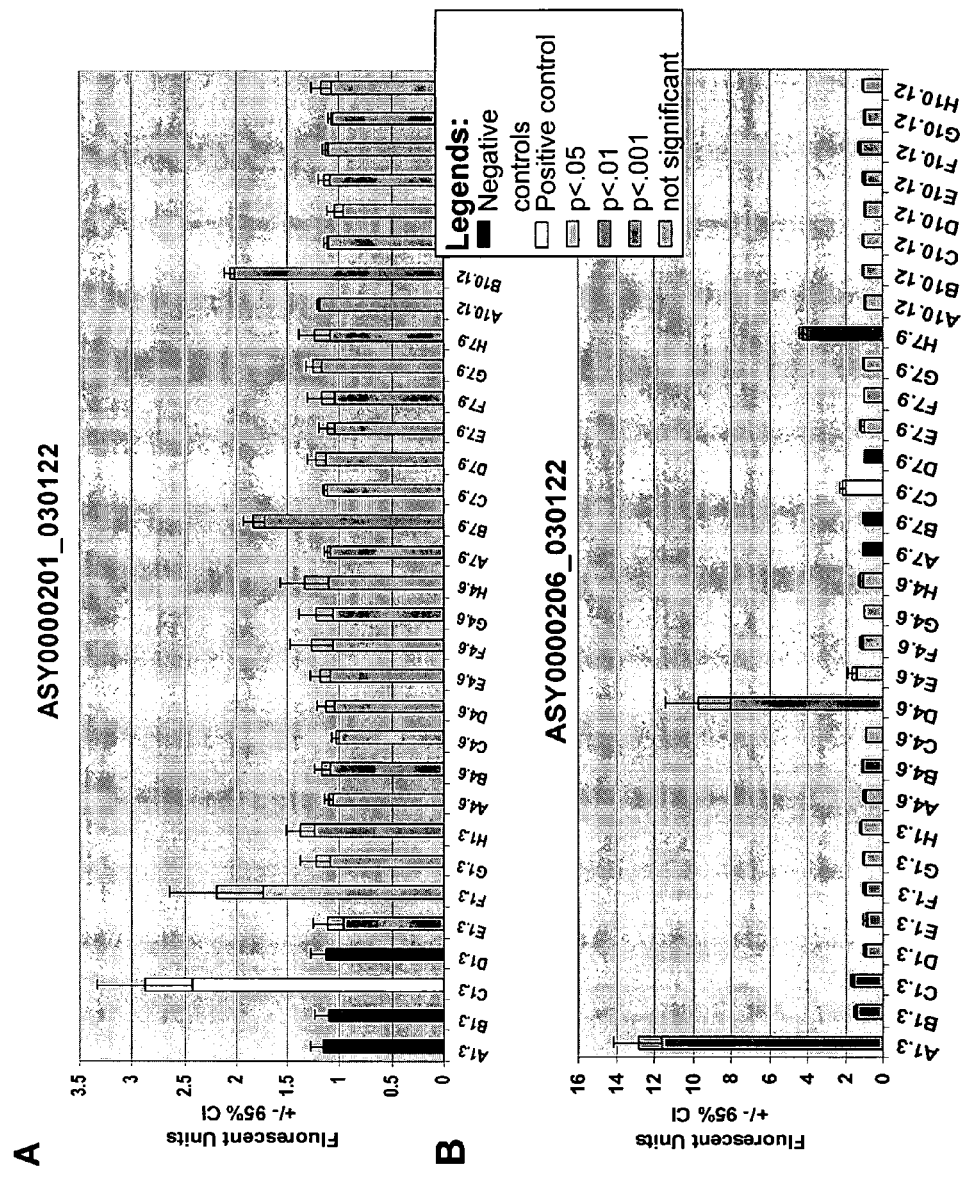
Fig. 7 Identifying interacting proteins with PCA: fluorescence spectrometry

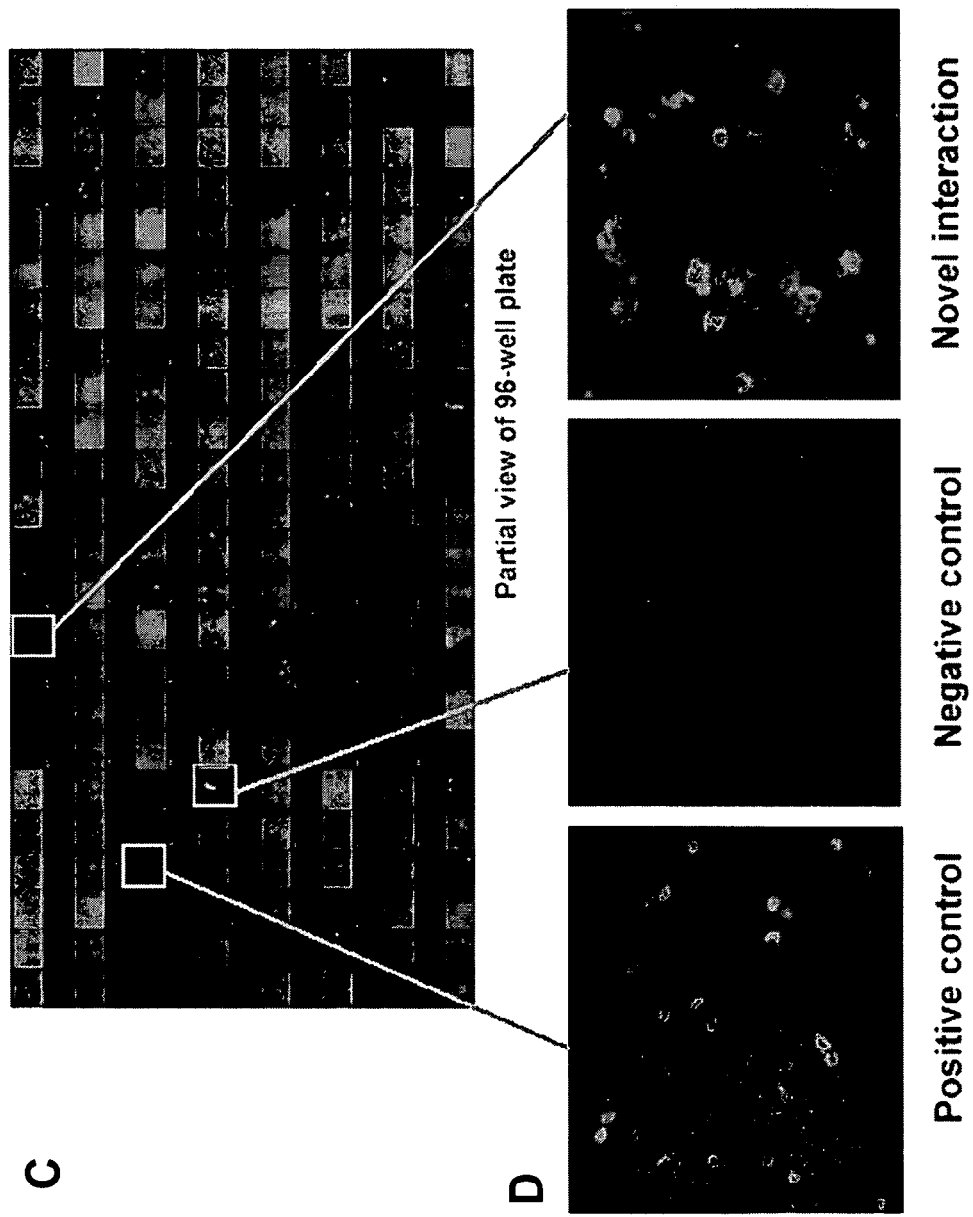
Fig 7. Identifying interacting proteins with PCA: automated microscopy

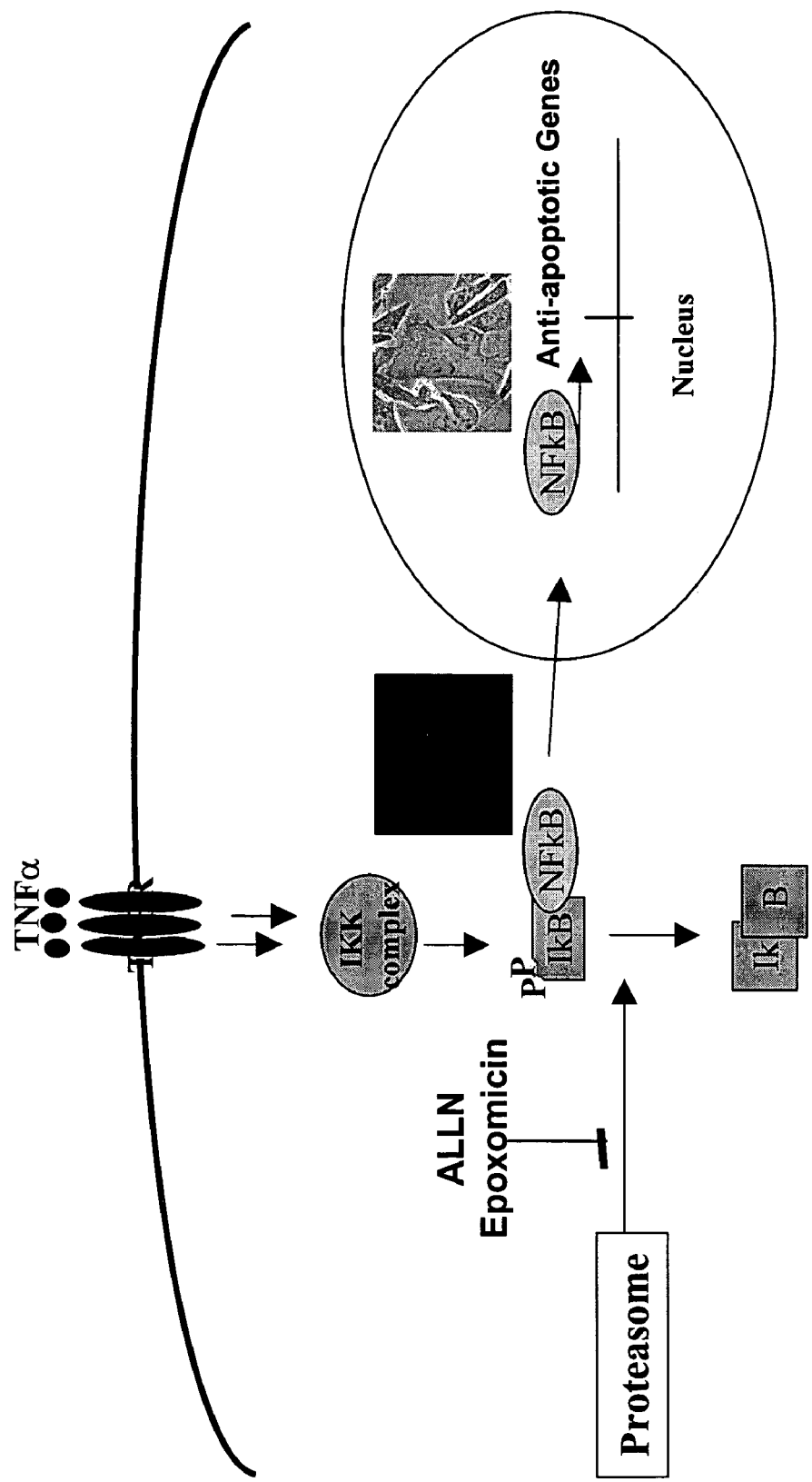
Fig. 8 TNF signaling pathway

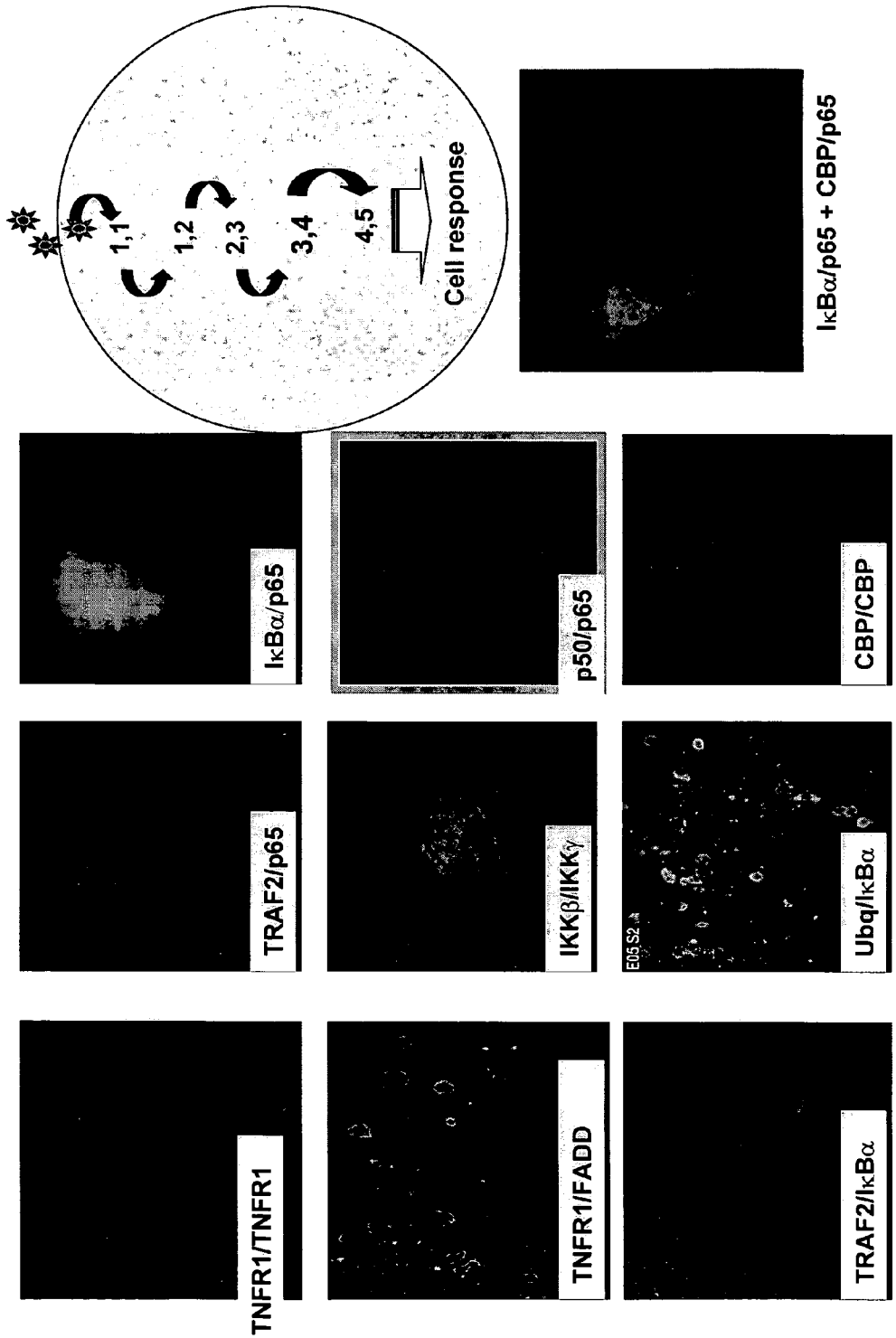
Fig. 9 Fluorescent PCAs for various steps in the TNF- and NFκB-dependent signaling pathways

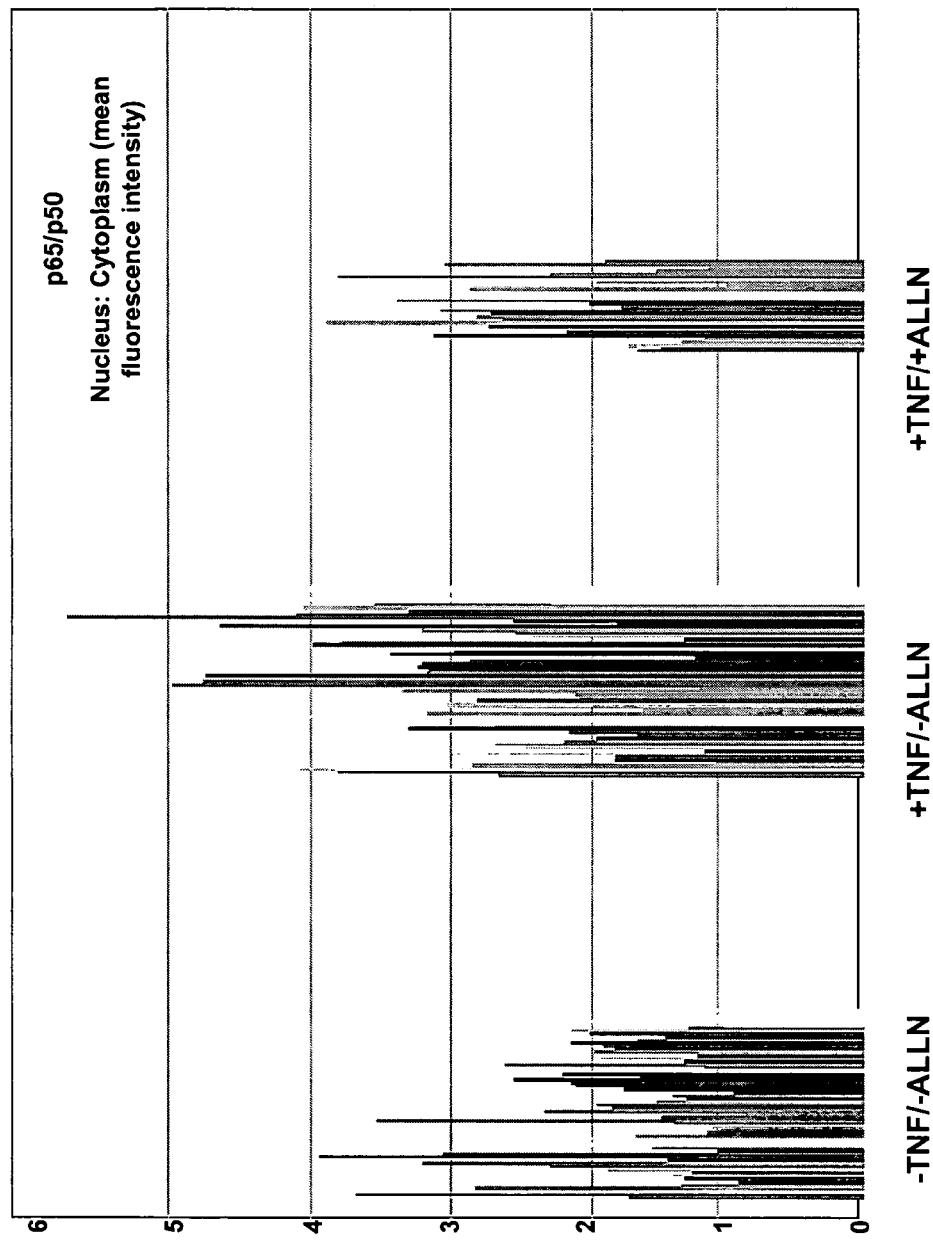
Fig. 10 TNF induction and ALLN inhibition of NFκB translocation in a transient YFP PCA

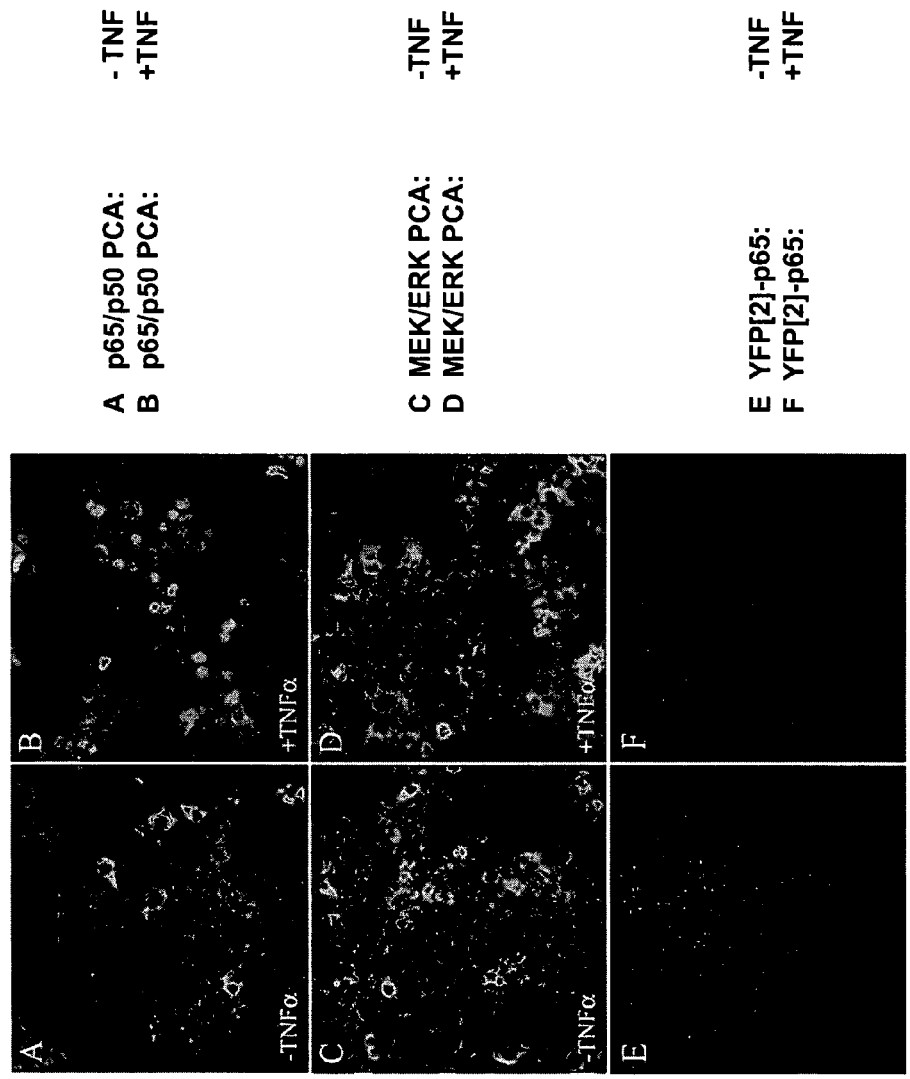
Fig. 11 Stable cell lines with PCA inside; and the absence of signal with individual gene constructs
A  p65/p50 PCA:    -TNF
B  p65/p50 PCA:    +TNF
C  MEK/ERK PCA:    -TNF
D  MEK/ERK PCA:    +TNF
E  YFP[2]-p65:     -TNF
F  YFP[2]-p65:     +TNF

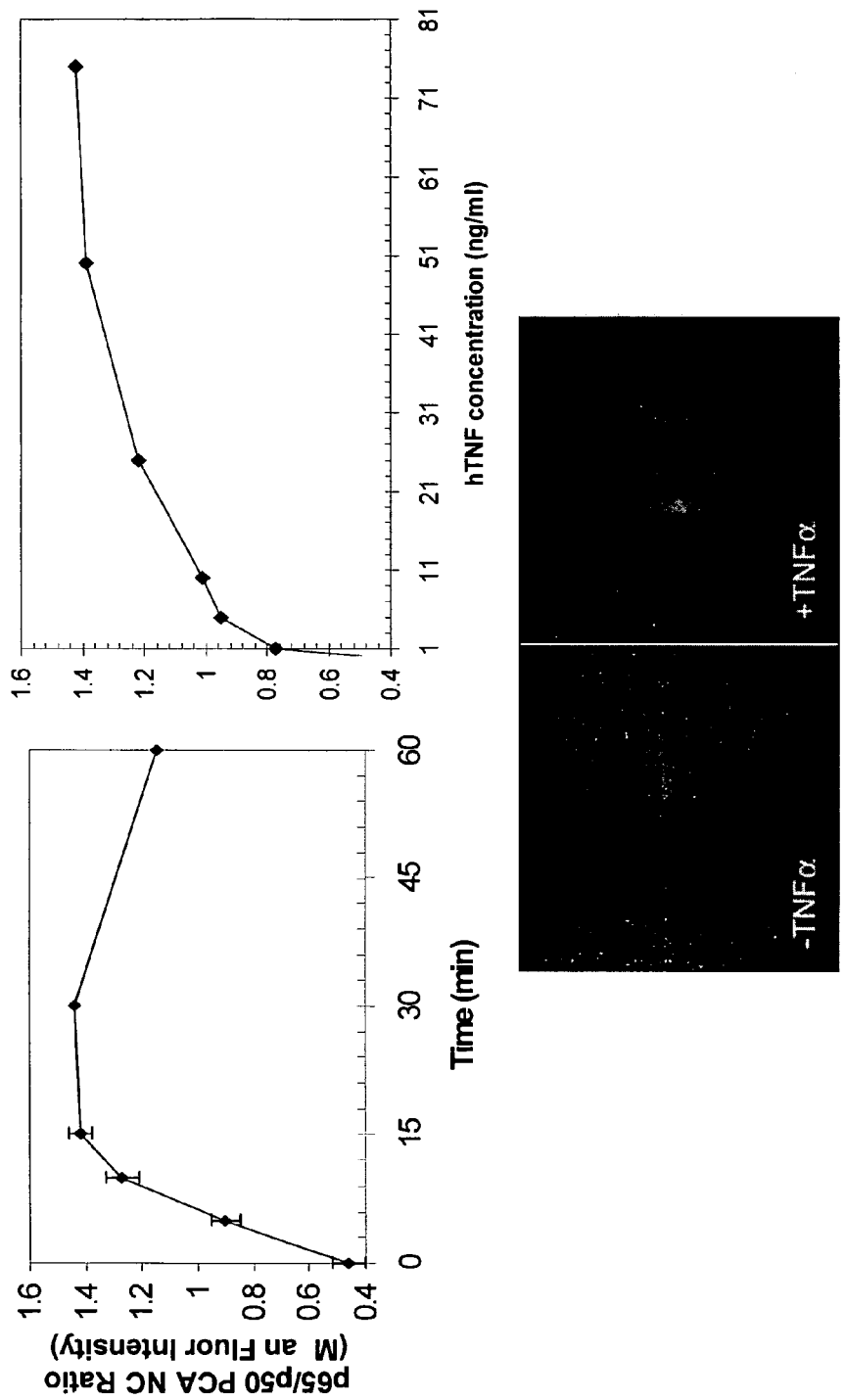
Fig. 12 (A) TNF induction of NFκB translocation in a stable cell line with PCA Inside

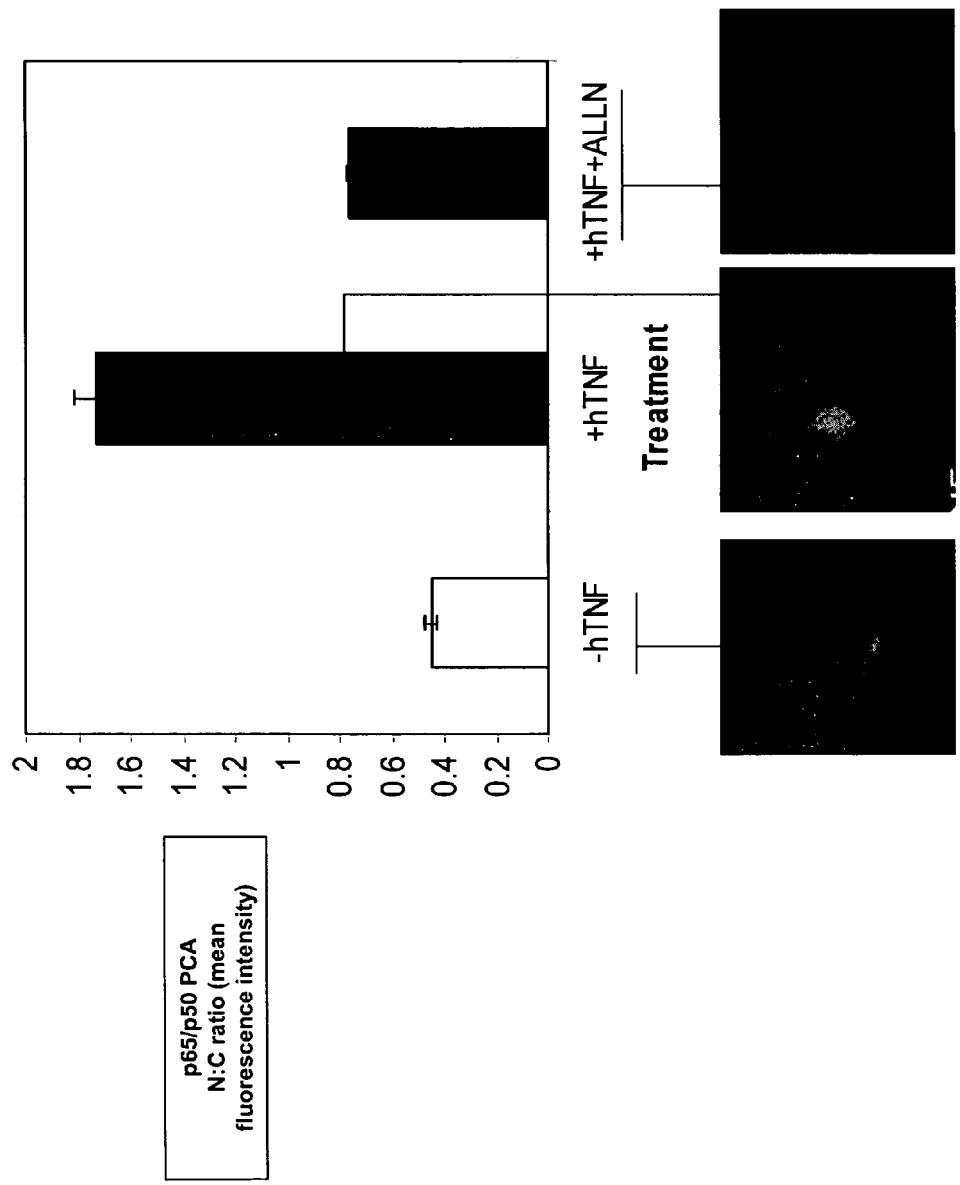
Fig. 12(B) Fluorescent high-content assay in a stable cell line showing inhibition by ALLN

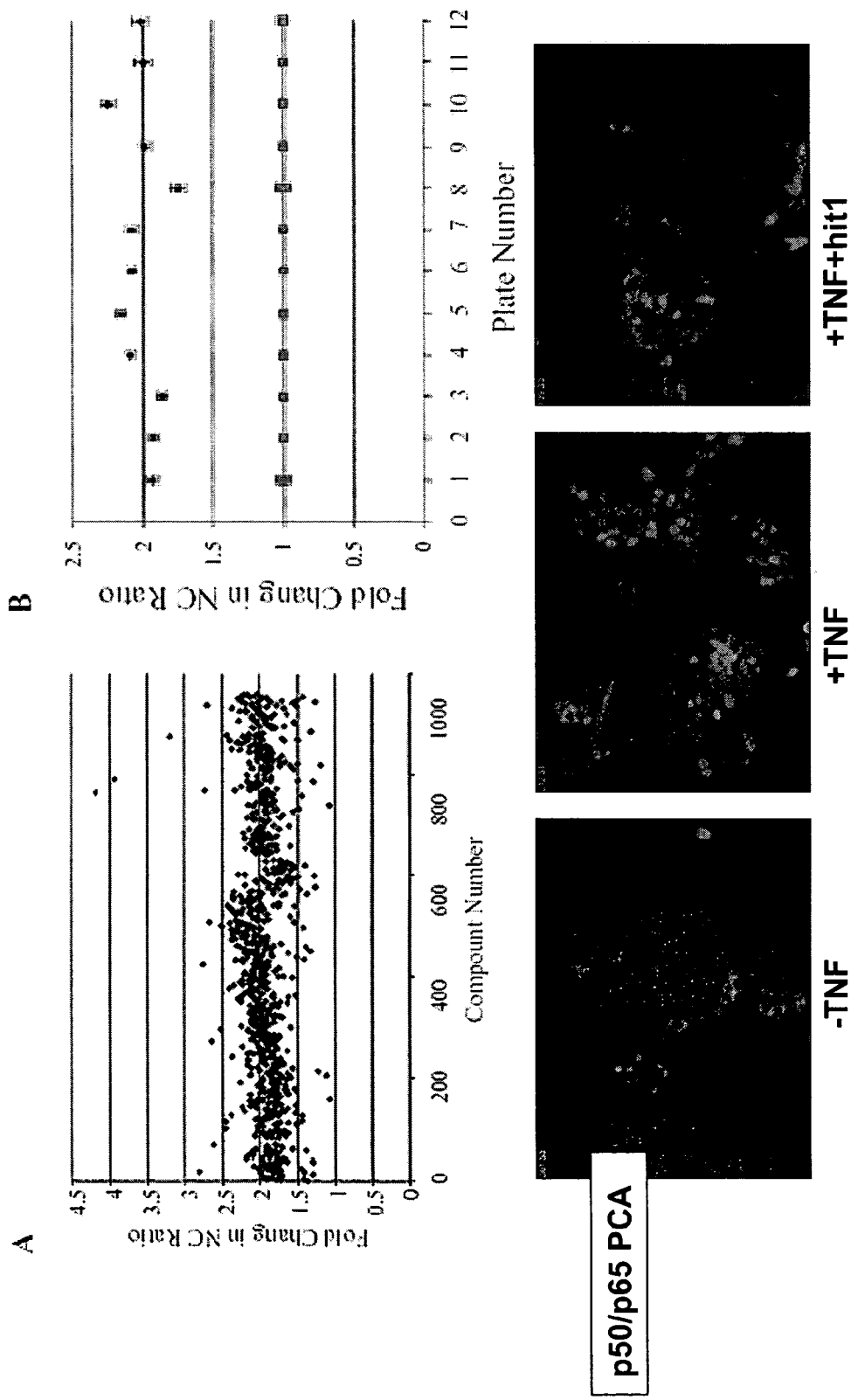
Fig. 12(C) High-content screening of a small-molecule library

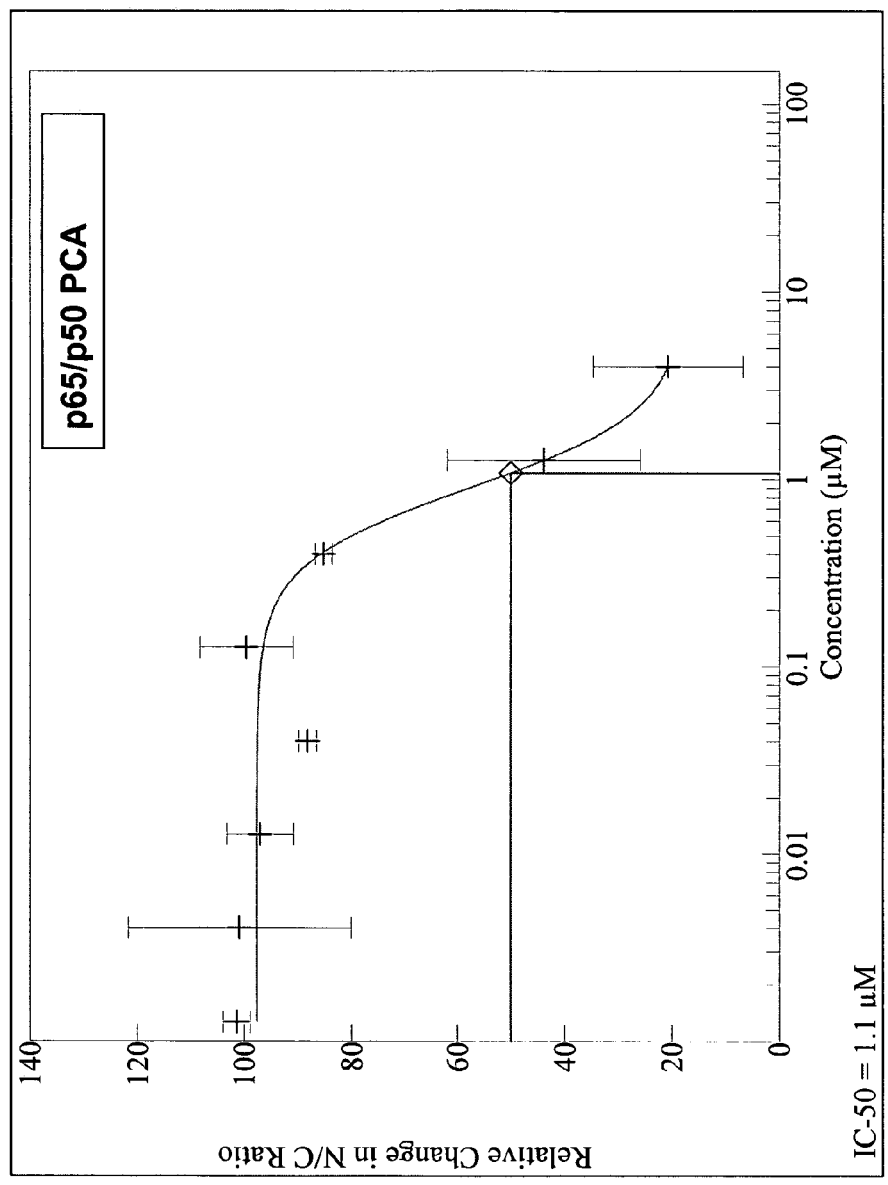
Fig. 12 (D) Dose response curve for a novel 'hit' identified by library screening

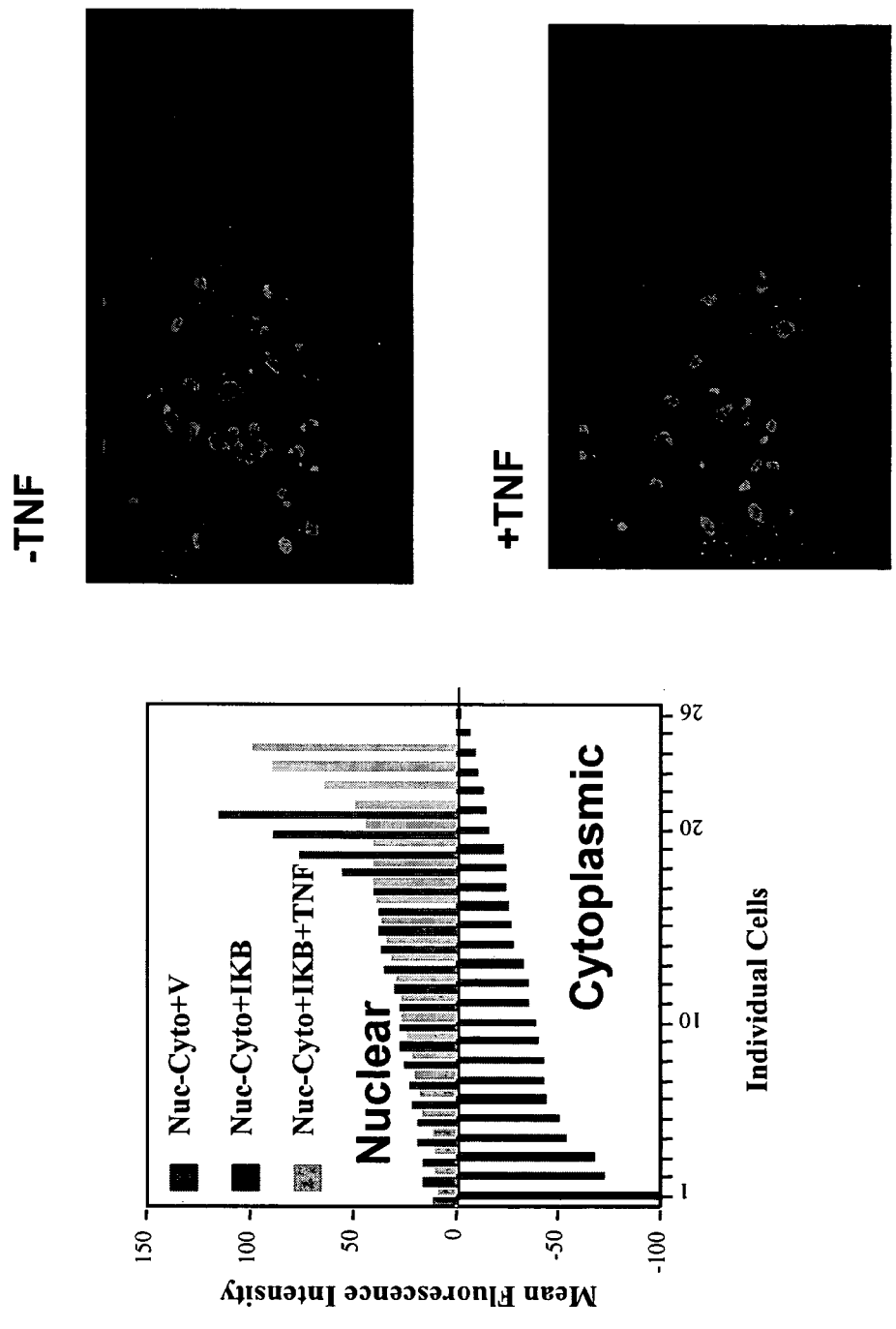
Fig. 13 (A) TNF induction of NFκB translocation (DHFR PCA in transient assays)

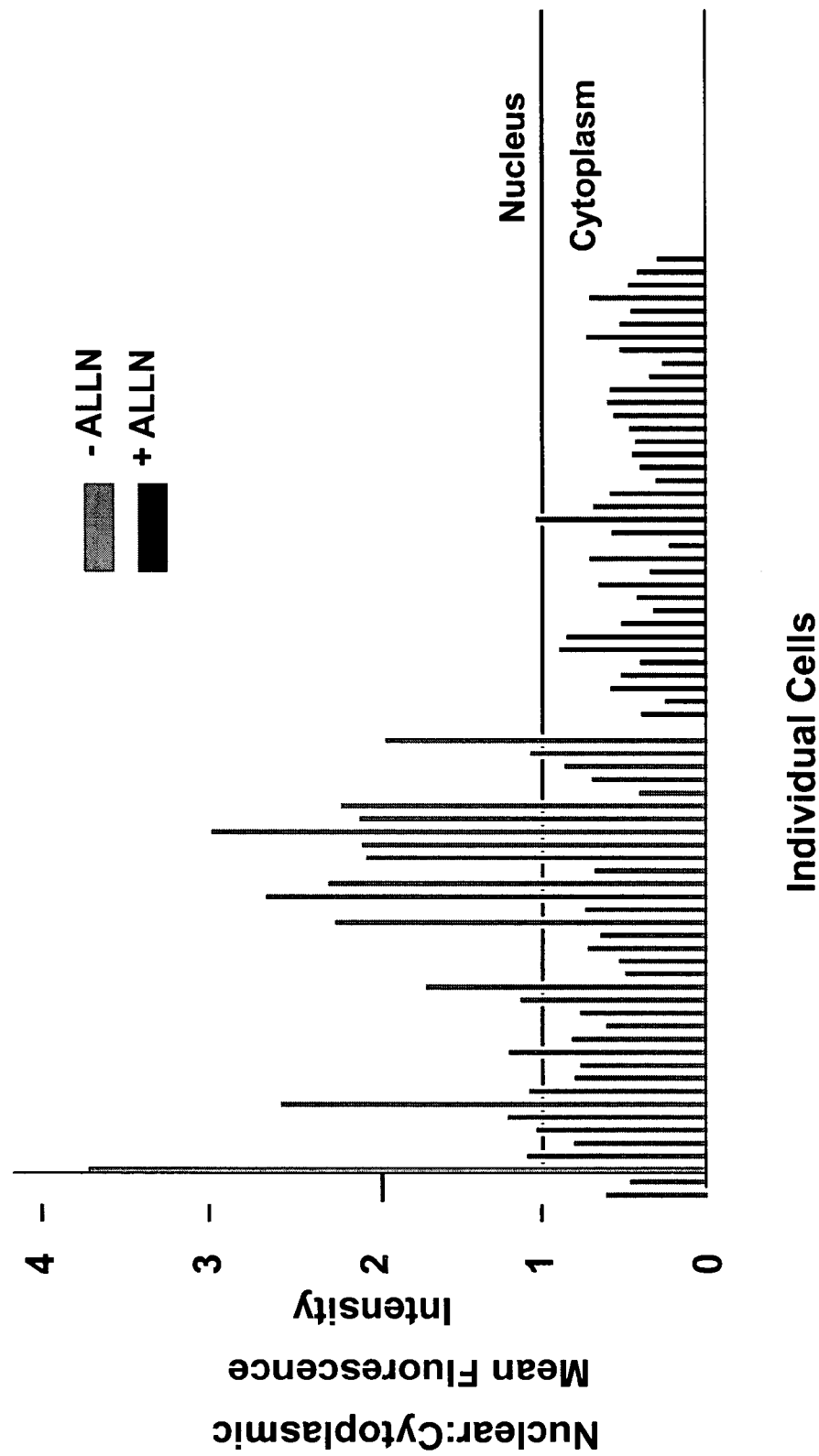
Fig. 13 (B) ALLN inhibition of NFκB translocation (DHFR PCA in transient assays)

Fig. 14 Fluorescent high-throughput assay for p65/IκB in a stable cell line (PCA Inside)
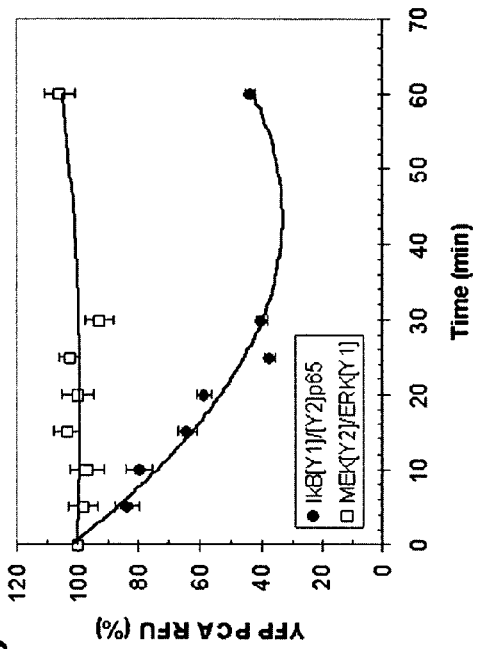
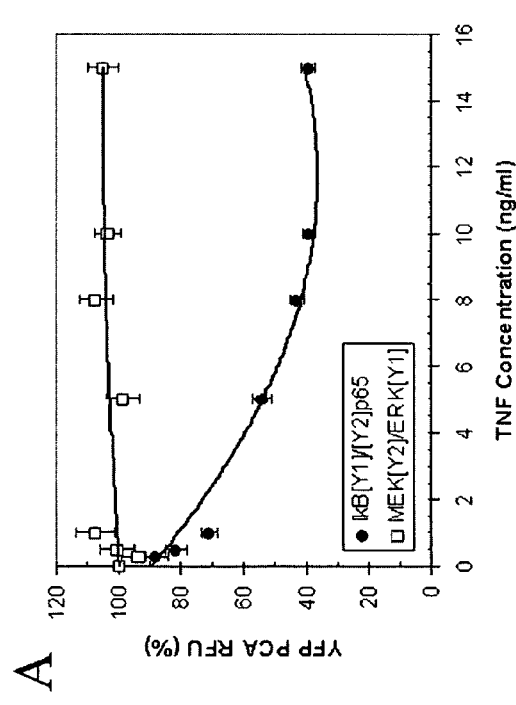

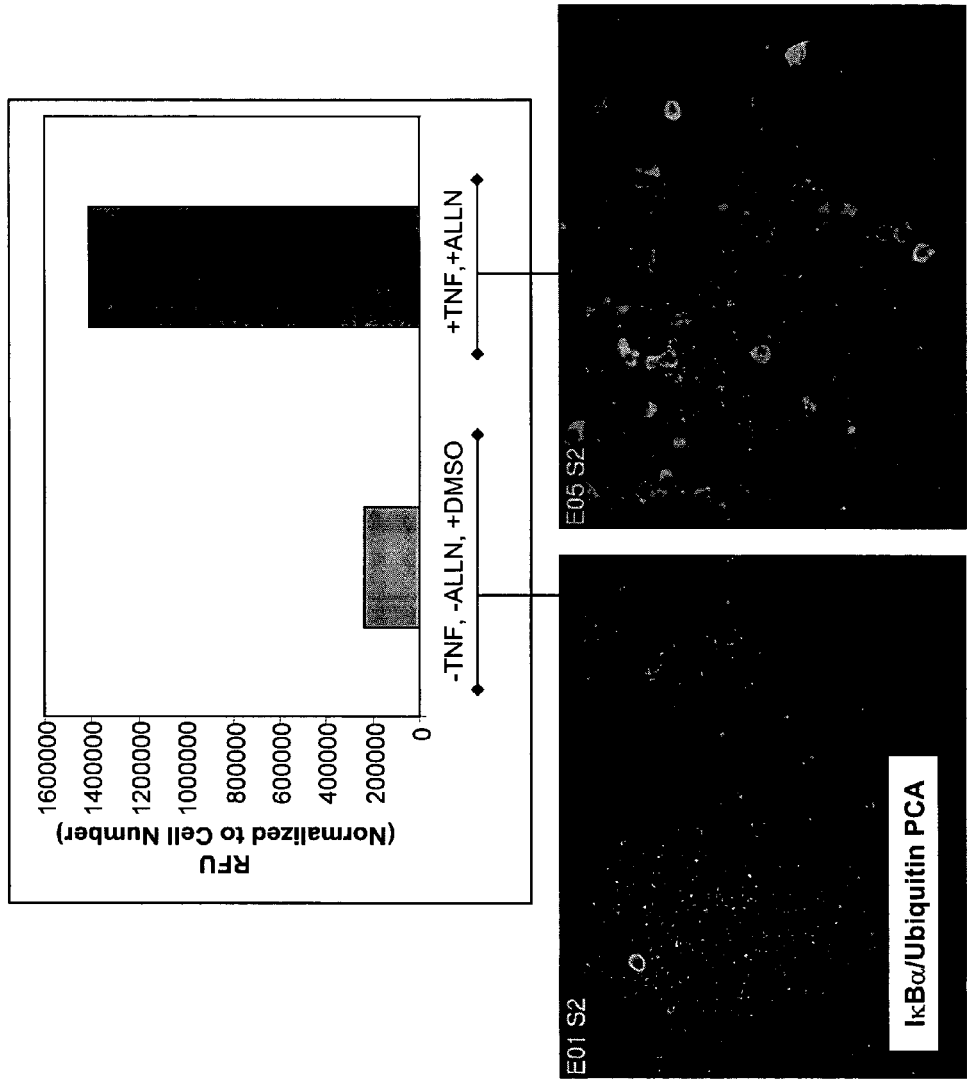
Fig. 15 Effects of TNF and ALLN on ubiquitin-protein complexes

Fig. 16 Vector construction and examples

1. Select each gene (or library) of interest;
2. Select PCA fragment pair (F1, F2) suitable for the assay type;
3. Select a constitutive or inducible promoter appropriate for the cell type;
4. Subclone each gene of interest (or gene library) into one or more fragment orientations (4 possible as shown below)
5. Perform PCA with complementary (F1/ F2) pairs of constructs containing genes of interest

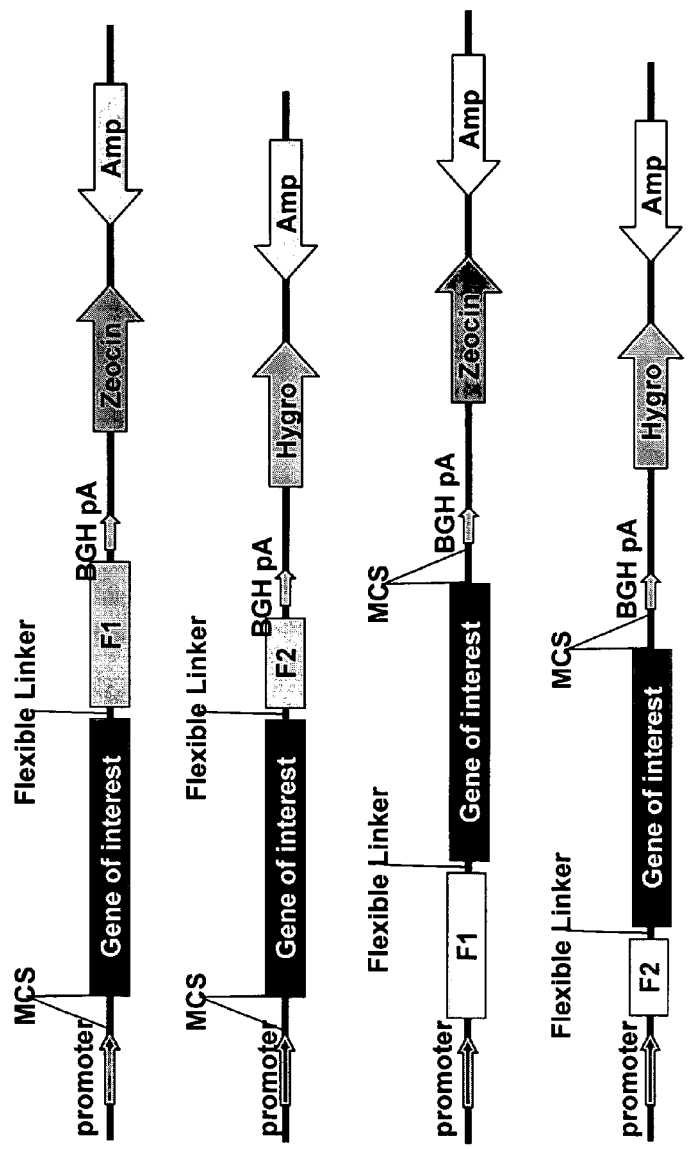

Fig. 17   Example of a Dual PCA

1. Select a survival/selection PCA (e.g. GCN4-DHFR-F[1,2]/GCN4-DHFR-F[3])

2. Select a PCA (F1, F2) suitable for HTS or HCS as described in the present invention 3. Select genes of interest (A,B) (or gene library(ies)) and subclone each gene into one or more fragments/orientations (2 possible orientations are shown below as A-F[1] and B-F[2])

4. Apply selective pressure to cells, using growth conditions based on the survival/selection PCA (e.g. DHFR selection with MTX). Cells that survive will also co-express the A-F[1] and B-F[2] fusion proteins.

5. With the cells selected in step 4, perform a fluorescent or luminescent HTS or HCS, using the assay conditions that are specific for the PCA chosen in step 2.

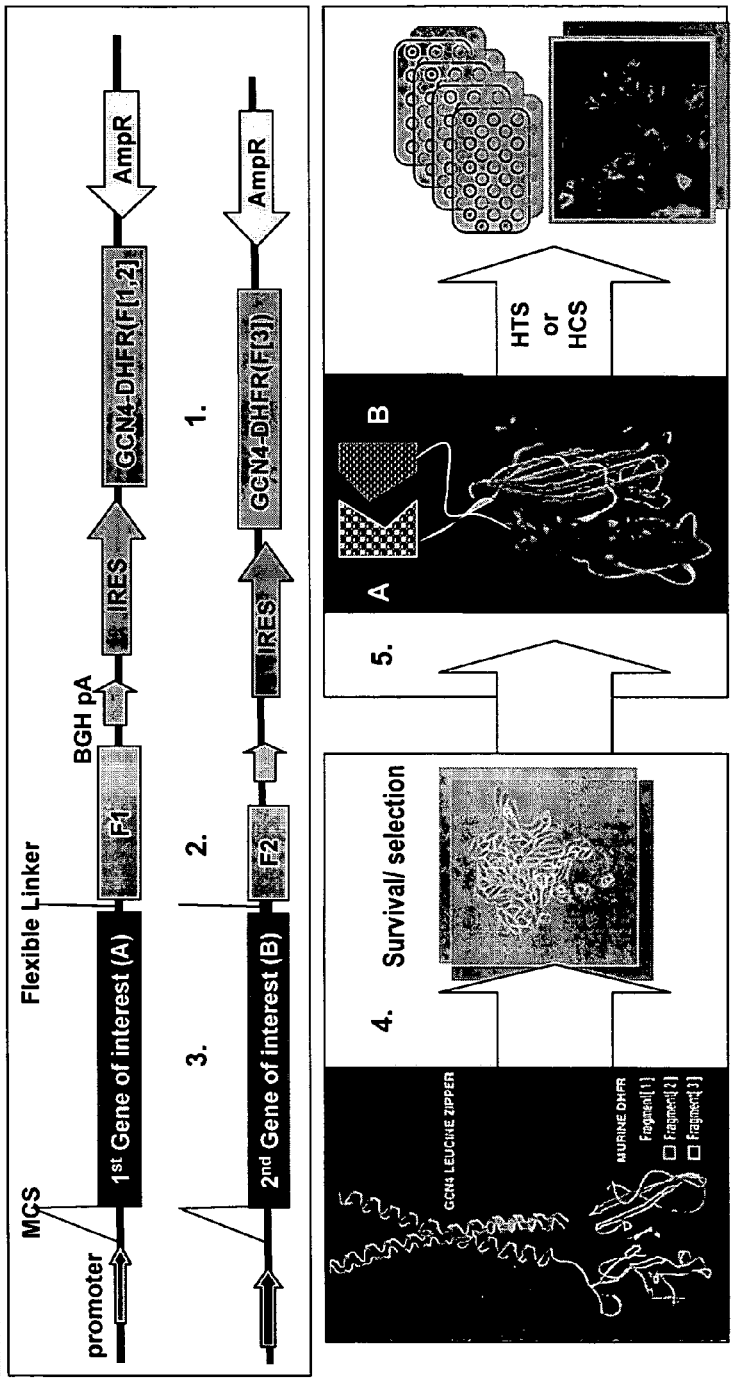

PROTEIN FRAGMENT COMPLEMENTATION ASSAYS FOR HIGH-THROUGHPUT AND HIGH-CONTENT SCREENING

This application claims the priority benefit under 35 U.S.C. section 119 of U.S. Provisional Patent Application No. 60/445,225 entitled "Protein fragment complementation assays for high-throughput and high-content screening", filed Feb. 6, 2003, which is in its entirety herein incorporated by reference. This Application is also a continuation-in-part of U.S. application Ser. No. 10/353,090 filed Jan. 29, 2003; which application is a continuation of pending U.S. application Ser. No. 10/154,758 filed May 24, 2002 now U.S. Pat. No. 6,929,916; which is a continuation of U.S. Ser. No. 09/499,464 filed Feb. 7, 2000; and now U.S. Pat. No. 6,428,951; which is a continuation of U.S. Ser. No. 09/017,412 filed Feb. 2, 1998; and now U.S. Pat. No. 6,270,964. The entire contents of all those patents and applications are incorporated by reference herein.

BACKGROUND OF THE INVENTION

Pharmaceutical company investment in new drug discovery and development has increased dramatically over the last ten years, yet the rate of new drug approvals has not kept pace. Expensive pre-clinical and clinical failures are responsible for much of the inefficiency of the current process. There is currently a need in drug discovery and development for rapid and robust methods for performing biologically relevant assays in high throughput. In particular, cell-based assays are critical for assessing the biological activity of chemical compounds and the mechanism-of-action of new biological targets.

In addition, there is a need to quickly and inexpensively screen large numbers of chemical compounds. This need has arisen in the pharmaceutical industry where it is common to test chemical compounds for activity against a variety of biochemical targets, for example, receptors, enzymes and signaling proteins. These chemical compounds are collected in large libraries, sometimes exceeding one million distinct compounds. The use of the term chemical compound is intended to be interpreted broadly so as to include, but not be limited to, simple organic and inorganic molecules, proteins, peptides, antibodies, nucleic acids and oligonucleotides, carbohydrates, lipids, or any chemical entity of biological interest. The use of the term chemical library is intended to be interpreted broadly so as to include, but not be limited to, collections of molecules.

Most screening of chemical libraries is performed with in vitro assays. Once developed, such assays are highly sensitive, reproducible, and inexpensive to perform. Techniques such as scintillation proximity, fluorescence polarization and time-resolved fluorescence resonance energy transfer (FRET) or surface plasmon resonance spectroscopy have enabled large-scale screening of diverse biochemical processes such as ligand-receptor binding and protein kinase activity. Although such assays are inexpensive to perform, they can take 6 months or longer to develop. A major problem is that the development of an in vitro assay requires specific reagents for every target of interest, including purified protein for the target against which the screen is to be run. Often it is difficult to express the protein of interest and/or to obtain a sufficient quantity of the protein in pure form. Moreover, although in vitro assays are the gold standard for pharmacology and studies of structure activity relationships, in vitro screening does not provide information about the biological availability or activity of the compound hit.

Cell-based HTS and HCS assays could represent the fastest approach to screening poorly characterized targets. The increased numbers of drug targets that are derived from genomics approaches has driven the development of multiple 'gene to screen' approaches to interrogate poorly defined targets, many of which rely on cellular assay systems. For example, cell-based screening approaches have been heavily employed for orphan receptors (those with no known ligand). These speculative targets are most easily screened in a format in which the target is expressed and regulated in the most physiologically relevant manner. These could include targets that regulate a biochemical pathway, targets that are themselves regulated by poorly understood partners implicated in such processes, or targets that require assembly of a transcriptional regulatory complex. It may be best to screen such targets in the biological context of a cell in which all of the necessary components are pre-assembled and regulated.

The present invention concerns the construction and applications of Protein-fragment Complementation assays (PCAs) for high-throughput and high-content screening. Specific and broad applications to drug discovery are presented; specifically: (1) Screening of chemical compounds and chemical libraries to identify chemicals that alter the function of specific biochemical pathways and (2) Screening of cDNA libraries to identify genes that serve a role in specific biochemical pathways We have previously described PCAs for in vivo interrogation of biochemical pathways. At the basic level, PCAs are methods to measure protein-protein interactions in intact, living cells. However they have specific and unique features that make them particularly important tools in drug discovery: (a) The PCA strategy is the first and only direct and quantitative functional assay technology that is applicable to any cell of interest including human cells, (b) Unlike yeast two-hybrid or transcription reporter approaches, PCA does not rely on additional cellular machinery (such as the yeast transcription apparatus), on de-convolution of signals, or on secondary and tertiary experiments, (c) Genes are expressed in the relevant cellular context and the resulting proteins reflect the native biological state including the correct post-translational modifications, (d) Protein and drug function can be assessed within the appropriate sub-cellular context, (e) Quantitative high-throughput and high-content assays can readily be constructed with PCA using fluorescent or luminescent readouts, (f) PCA fragments can be synthesized and/or genetically engineered to create assays with any required properties including signal intensity, stability, spectral properties, color and other properties, (g) Flexibility in expression vector design enables the user to select among various gene orientations, linker lengths, reporter types, constitutive or inducible promoters, and various selectable marker strategies depending on the assay demands and finally, (h) unlike fluorescent spectroscopic techniques or subunit complementation approaches, careful adjustment of protein pair expression levels does not need to be made.

Cell-based Reporters and Instrumentation

Cellular screening techniques can be broadly classified into two groups: semi-biochemical approaches that involve the analysis of cell lysates, or live cell assays. The present invention is largely focused on whole cell assays. Whole cell assay methodologies vary with respect to assay principle, but have largely in common a form of luminescence or fluorescence for detection. Luminescence is a phenomenon in which energy is specifically channeled to a molecule to produce an excited state. Luminescence includes fluorescence, phosphorescence, chemiluminescence and bioluminescence.

An ever-increasing list of fluorescent proteins include the widely-used GFP derived from *Aequorea Victoria* and spectral variants thereof. The list includes a variety of fluorescent proteins derived from other marine organisms; bacteria; fungi; algae; dinoflagellates; and certain terrestrial species (See table I). These reporters have the advantage of not requiring any exogenous substrates or co-factors for the generation of a signal but do require an external source of radiation for excitation of the intrinsic fluorophore. In addition, the increasing availability of genes encoding a broad spectrum of fluorescent reporter proteins enables the construction of assays tailored for specific applications, cell types, and detection systems.

Different classes of luminescent proteins—luciferases—have been have been discovered in bacteria and eukaryotes. Luciferases are proteins that catalyze the conversion of a natural substrate into a product that emits light in the visible spectrum and thus require no external radiation source. Several examples are listed in table I. Monomeric forms of luciferase have been cloned from firefly, Renilla, and other organisms. Firefly luciferase is the most common of the bioluminescent reporters and is a 61 kDa monomeric enzyme that catalyzes a two-step oxidation reaction to yield light. Renilla luciferase is a 31 kDa monomeric enzyme that catalyzes the oxidation of coelenterazine to yield coelenteramide and blue light of 480 nm. Substrates for luciferase are widely available from commercial suppliers such as Promega Corporation and Invitrogen Molecular Probes.

A variety of useful enzymatic reporters are enzymes that either generate a fluorescent signal or are capable of binding small molecules that can be tagged with a fluorescent moiety to serve as a fluorescent probe. For example, dihydrofolate reductase (DHFR) is capable of binding methotrexate with high affinity; a methotrexate-fluorophore conjugate can serve as a quantitative fluorescent reagent for the measurement of the amount of DHFR within a cell. By tagging methotrexate with any of a number of fluorescent molecules such as fluorescein, rhodamine, Texas Red, BODIPY and other commercially available molecules (such as those available from Molecular Probes/Invitrogen and other suppliers) a range variety of fluorescent readouts can be generated. The wide range of techniques of immunohistochemistry and immunocytochemistry can be applied to whole cells. For example, ligands and other probes can be tagged directly with fluorescein or another fluorophore for detection of binding to cellular proteins; or can be tagged with enzymes such as alkaline phosphatase or horseradish peroxidase to enable indirect detection and localization of signal.

Many other enzymes can be used to generate a fluorescent signal in live cells by using specific, cell-permeable substrate that either becomes fluorescent or shifts its fluorescence spectrum upon enzymatic cleavage. For example, substrates for beta-lactamase exist whose fluorescence emission properties change in a measurable way upon cleavage of a beta-lactam core moiety to which fluorophores are attached. Changes include, shifts in fluorophore absorption or emission wavelengths, or cleavage of a covalent assembly of emmision-absorption-mathched fluorophore pairs that in the covalently-assembled form sustain resonance energy transfer between the two fluorophores that is lost when the two are separated. Membrane-permeant, fluorescent BLA substrates such as the widely-used CCF2/AM allow the measurement of gene expression in live mammalian cells in the absence or presence of compounds from a biologically active chemical library.

Luminescent, fluorescent or bioluminescent signals are easily detected and quantified with any one of a variety of automated and/or high-throughput instrumentation systems including fluorescence multi-well plate readers, fluorescence activated cell sorters (FACS) and automated cell-based imaging systems that provide spatial resolution of the signal. A variety of instrumentation systems have been developed to automate HCS including the automated fluorescence imaging and automated microscopy systems developed by Cellomics, Amersham, TTP, Q3DM, Evotec, Universal Imaging and Zeiss. Fluorescence recovery after photobleaching (FRAP) and time lapse fluorescence microscopy have also been used to study protein mobility in living cells. Although the optical instrumentation and hardware have advanced to the point that any bioluminescent signal can be detected with high sensitivity and high throughput, the existing assay choices are limited either with respect to their range of application, format, biological relevance, or ease of use.

Transcriptional Reporter Assays

Cell-based reporters are often used to construct transcriptional reporter assays which allow monitoring of the cellular events associated with signal transduction and gene expression. Reporter gene assays couple the biological activity of a target to the expression of a readily detected enzyme or protein reporter. Based upon the fusion of transcriptional control elements to a variety of reporter genes, these systems "report" the effects of a cascade of signaling events on gene expression inside cells. Synthetic repeats of a particular response element can be inserted upstream of the reporter gene to regulate its expression in response to signaling molecules generated by activation of a specific pathway in a live cell. The variety of transcriptional reporter genes and their application is very broad and includes drug screening systems based on beta-galactosidase (beta-gal), luciferase, alkaline phosphatase (luminescent assay), GFP, aequorin, and a variety of newer bioluminescent or fluorescent reporters.

In general, transcription reporter assays have the capacity to provide information on the response of a pathway to natural or synthetic chemical agents on one or more biochemical pathways, however they only indirectly measure the effect of an agent on a pathway by measuring the consequence of pathway activation or inhibition, and not the site of action of the compound. For this reason, mammalian cell-based methods have been sought to directly quantitate protein-protein interactions that comprise the functional elements of cellular biochemical pathways and to develop assays for drug discovery based on these pathways.

Cellular Assays for Individual Proteins Tagged with Fluorophores or Luminophores Subcellular compartmentalization of signaling proteins is an important phenomenon not only in defining how a biochemical pathway is activated but also in influencing the desired physiological consequence of pathway activation. This aspect of drug discovery has seen a major advance as a result of the cloning and availability of a variety of intrinsically fluorescent proteins with distinct molecular properties. High-content (also known as high-context) screening (HCS) is a live cell assay approach that relies upon image-based analysis of cells to detect the subcellular location and redistribution of proteins in response to stimuli or inhibitors of cellular processes. Fluorescent probes can be used in HCS; for example, receptor internalization can be measured using a fluorescently-labeled ligand that binds to the transferrin receptor. Often, individual proteins are either expressed as fusion proteins—where the protein of interest is fused to a detectable moiety such as GFP—or are detected by immunocytochemistry after fixation, such as by the use of an antibody conjugated to Cy3 or another suitable dye. In this way, the subcellular location of a protein can be imaged and tracked in real time. One of the largest areas of development is in applications of GFP color-shifted mutants and other more recently isolated new fluorescent proteins, which allow the development of increasingly advanced live cell assays such as multi-color assays. A range of GFP assays have been developed to analyze key intracellular signaling pathways by following the redistribution of GFP fusion proteins in live cells. For drug screening by HCS the objective is to identify therapeutic compounds that block disease pathways by inhibiting the movement of key signaling proteins to their site of action within the cell.

Tagging a protein with a fluorophore or a luminophore enables tracking of that particular protein in response to cell stimuli or inhibitors. For example, the activation of cell signaling by TNF can be detected by expressing the p65 subunit of the NFkB transcription complex as a GFP fusion and then following the redistribution of fluorescence from the cytosolic compartment to the nuclear compartment of the cell within minutes after TNF stimulation of live cells (JA Schmid et al., 2000, Dynamics of NFkB and IkBa studied with green fluorescent protein (GFP) fusion proteins, J. Biol. Chem. 275: 17035–17042). What has been unique about these approaches is the ability to allow monitoring of the dynamics of individual protein movements in living cells, thus addressing both the spatial and temporal aspects of signaling.

Measuring Protein-Protein Interactions

In contrast to monitoring a single protein, a protein-protein interaction assay is capable of measuring the existence and quantity of complexes between two proteins.

The classical yeast two-hybrid (Y2H) system has been a widely example of such assays, and has been adapted to mammalian two-hybrid systems. These assays have particularly been used in screening cDNA libraries to identify proteins that interact with some known protein. By virtue of being shown to interact with a known "bait" protein, a cDNA product can be inferred to potentially participate in the biochemical process in which the known protein participates. Although bait-versus-library screening with Y2H has been carried out in high throughput, several features of Y2H limit its utility for functional protein target validation and for screening of chemical libraries. First, Y2H often requires the expression of the proteins of interest within the nucleus of a cell such as the yeast cell, which is an unnatural context for most human proteins and cannot be used at all for human membrane proteins such as receptors. Second, yeast do not contain the human biochemical pathways that are of interest for drug discovery, which obviates pathway-based discovery and validation of novel, potential drug target proteins. Third, except for chemicals that directly disrupt protein-protein interactions, Y2H is not of use in identifying pharmacologically active molecules that disrupt mammalian biochemical pathways.

In principle, cell based protein-protein interaction assays can be used to monitor the dynamic association and dissociation of proteins, both to monitor the activity of a biochemical pathway in the living cell and to directly study the effects of chemicals on the pathways. Unlike transcriptional reporter assays, the information obtained by monitoring a protein-protein interaction is what is happening specifically in a particular branch or node of a cell signaling pathway, not its endpoint.

The most widespread fluorescent, cell-based protein-protein interaction assay is based on the phenomenon of fluorescence resonance energy transfer (FRET) or bioluminescence resonance energy transfer (BRET). In a FRET assay the genes for two different fluorescent reporters, capable of undergoing FRET are separately fused to genes encoding of interest, and the fusion proteins are co-expressed in live cells. When a protein complex forms between the proteins of interest, the fluorophores are brought into proximity if the two proteins possess overlapping emission and excitation, emission of photons by a first, "donor" fluorophore, results in the efficient absorption of the emitted photons by the second, "acceptor" fluorophore. The FRET pair fluoresces with a unique combination of excitation and emission wavelengths that can be distinguished from those of either fluorophore alone in living cells. As specific examples, a variety of GFP mutants have been used in FRET assays, including cyan, citrine, enhanced green and enhanced blue fluorescent proteins. With BRET, a luminescent protein, for example the enzyme Renilla luciferase (RLuc) is used as a donor and a green fluorescent protein (GFP) is used as an acceptor molecule. Upon addition of a compound that serves as the substrate for Rluc, the FRET signal is measured by comparing the amount of blue light emitted by Rluc to the amount of green light emitted by GFP. The ratio of green to blue increases as the two proteins are brought into proximity. Quantifying FRET or BRET—can be technically challenging and use in imaging protein-protein interactions is very limited due to the very weak FRET signal. FRET often does not produce a very bright signal because the acceptor fluorophore is excited only indirectly, through excitation of the donor. The fluorescence wavelengths of the donor and acceptor must be quite close for FRET to work, because FRET requires overlap of the donor emission and acceptor excitation. Newer methods are in development to enable deconvolution of FRET from bleedthrough and from autofluorescence. In addition, fluorescence lifetime imaging microscopy (FLIM) eliminates many of the artifacts associates with quantifying simple FRET intensity. However, at the present time FRET and BRET are not easily amenable to high-throughput screening of either cDNA libraries or chemical libraries as we describe below.

A variety of assays have been constructed based either on activity of wild-type beta-galactosidase or on the phenomenon of alpha- or omega-complementation. Beta-gal is a multimeric enzyme which forms tetramers and octomeric complexes of up to 1 million Daltons. beta-gal subunits undergo self-oligomerization which leads to activity. This naturally-occurring phenomenon has been used to develop a variety of in vitro, homogeneous assays that are the subject of over 30 patents. Alpha- or omega-complementation of beta-gal, which was first reported in 1965, has been utilized to develop assays for the detection of antibody-antigen, drug-protein, protein-protein, and other bio-molecular interactions. However, the adaptation of beta-gal complementation to live cell assays has been limited because the phenomenon occurs naturally, resulting in significant background activity. The background activity problem has been overcome in part by the development of low-affinity, mutant subunits with a diminished or negligible ability to complement naturally, enabling various assays including for example the detection of ligand-dependent activation of the EGF receptor in live cells. On the other hand, beta-gal is not suitable for high-content assays because the product of the beta-gal reaction diffuses throughout the cell.

Protein-protein interaction assays based on protein-fragment complementation (PCA). PCA represents an alternative to FRET and BRET for measurements of the association, dissociation or localization of protein-protein complexes within the cell. PCA enables the determination and quantitation of the amount and subcellular location of protein-protein complexes in living cells. With PCA, proteins are expressed as fusions to engineered polypeptide fragments, where the polypeptide fragments themselves (a) are not fluorescent or luminescent moieties; (b) are not naturally-occurring; and (c) are generated by fragmentation of a reporter.

Michnick et al. (U.S. Pat. No. 6,270,964) taught that any reporter protein of interest can be used in PCA, including any of the reporters described above. Thus, reporters suitable for PCA include, but are not limited to, any of a number of enzymes and fluorescent, luminescent, or phosphorescent proteins. Small monomeric proteins are preferred for PCA, including monomeric enzymes and monomeric fluorescent proteins, resulting in small (~150 amino acid) fragments. Since any reporter protein can be fragmented using the principles established by Michnick et al., assays can be tailored to the particular demands of the cell type, target, signaling process, and instrumentation of choice. Finally, the ability to choose among a wide range of reporter fragments enables the construction of fluorescent, luminescent, phosphorescent, or otherwise detectable signals; and the choice of high-content or high-throughput assay formats.

As we have shown previously and in the present invention, the fragments engineered for PCA are not individually fluorescent or luminescent. This feature of PCA distinguishes it from other inventions that involve tagging proteins with fluorescent molecules or luminophores, such as U.S. Pat. No. 6,518,021 (Thastrup et al.) in which proteins are tagged with GFP or other luminophores. A PCA fragment is not a luminophore and does not enable monitoring of the redistribution of an individual protein. In contrast, what is measured with PCA is the formation of a complex between two proteins.

Finally, PCAs can be used in conjunction with a variety of existing, automated systems for drug discovery, including existing high-content instrumentation and software such as that described in U.S. Pat. No. 5,989,835.

OBJECTS AND ADVANTAGES OF THE INVENTION

It is an object of the present invention to provide a method for drug discovery on a large scale in the biological context of the living cell.

More specifically, it is an object of the present invention to provide methods for rapidly constructing cell-based assays for any biochemical pathway or gene of interest, in order to accelerate the identification of potential therapeutic compounds for a variety of human conditions.

It is another object of the invention to allow the identification of novel biochemical pathways and the immediate and immediate construction of high-throughput screening assays for those pathways.

It is an additional object of the invention to provide high-throughput or high-content assays that can be broadly applied to a variety of existing instrumentation platforms, not requiring custom instrumentation for the performance of the assay.

Still, a further object of this invention is to teach methods for the construction of such assays based on any number of useful reporters that generate signals that can be detected in live cells.

Accordingly, an object of the invention is to demonstrate that any reporter protein can be fragmented and used to generate a signal in live cells and to provide numerous reporters suitable for high-throughput and high-content assays.

Another object of this invention is to enable the construction of both high-throughput assays and high-content assays to accelerate drug discovery for a variety of targets that may be difficult to screen by conventional methods.

An additional object of the invention is to demonstrate that the invention can be applied to detecting the effects of agonists, antagonists and inhibitors of biochemical pathways of therapeutic relevance.

A further object of the invention is to provide vector constructions and elements useful in high-content screening and high-throughput screening.

A still further object of the invention is to provide assays based on particular pathways, target classes, and target proteins useful for drug discovery.

The invention has the advantage of being broadly applicable to any pathway, gene, gene library, target class, reporter protein, detection mode, chemical library, automated format, automated instrumentation, vector design and cell type of interest.

SUMMARY OF THE INVENTION

The present invention seeks to provide the above-mentioned needs for drug discovery. The present invention provides a general strategy for carrying out drug discovery based on protein-fragment complementation assays. The present invention teaches how these assays can be applied to screening compounds and chemical libraries in order to identify natural products, organic molecules, ligands, antibodies or other pharmacologically active agents that can inhibit or activate specific biochemical or disease pathways in live cells.

Methods and compositions are provided both for high-throughput screens (HTS) and for high-content/high-context screens (HCS) for the screening of chemical libraries for compounds of potential therapeutic value. Both types of assays utilize readouts that are optically detectable in live cell, fixed cell or lysed cell assays, such as fluorescence, bioluminescence, chemiluminescence or phosphorescence. Both types of assays are fully compatible with state-of-the-art instrumentation, data capture, software and automation.

In the case of high-throughput screening, the bulk fluorescent or luminescent signal is detected, such as with fluorescence spectroscopy on a fluorescence microtiter plate reader, with a FACS analyzer, with a luminometer, or similar devices. In the case of high-content screening, individual cells are imaged and the PCA signal, and its sub-cellular location, is detected. The methods and assays provided herein may be performed in multiwell formats, in microtiter plates, in multispot formats, or in arrays, allowing flexibility in assay formatting and miniaturization.

The choice of HTS or HCS formats is determined by the biology of the process and the functions of the proteins being screened. It should be noted that in either case the assays do not require special instrumentation. It will be understood by a person skilled in the art that the HTS and HCS assays that are the subject of the present invention can be read with any instrument that is suitable for detection of the signal that is generated by the chosen reporter. Many such instrument systems are commercially available.

The present application also teaches methods for selecting an interacting protein pair in a pathway to be screened. Methods for identifying an interacting protein pair are provided in the present invention, and include cDNA library screening, gene-by-gene interaction mapping, and prior knowledge of a pathway or a protein-protein interaction. Examples of each of these methods are provided herein, as are specific pathways, target classes and individual proteins suitable for use in drug discovery according to the present invention.

The present application also explains the rationale for selecting a particular reporter in a PCA. Reporters suitable for HTS and HCS with PCA are shown in Table I and their characteristics, and a variety of methods for fragmentation, have already been described by Michnick et al. (U.S. Pat. No. 6,270,964). Examples of PCAs based on six such reporters are provided herein, including green fluorescent protein (GFP) and two variants thereof (YFP and IFP), dihydrofolate reductase (DHFR), beta-lactamase, and Renilla luciferase (RLuc). It will be understood by a person skilled in the art that the present invention is not limited to the particular PCAs presented, or the context in which they have been used in the examples presented herein. The present invention teaches that any reporter generating a detectable signal can be utilized to create a protein-fragment complementation assay for a particular need in drug discovery.

TABLE I

EXAMPLES of PCA REPORTERS FOR THE PRESENT INVENTION

| Protein | Nature of Signal | Reference |
|---|---|---|
| Aequorin monomeric calcium activated photoprotein | Luminescence, requires cell permeable coelenterazine luciferin and calcium | An automated aequorin luminescence-based functional calcium assay for G-protein-coupled receptors M. D. Ungrin et. al., Anal Biochem., 1999, 272, 34–42; Rapid changes of mitochondrial calcium revealed by specifically targeted recombinant aequorin, Rizzuto et. al., Nature, 1992, 358 (6384), 325–327 |
| AsFP499 and related fluorescent proteins from the sea anemone Anemonia sulcata | Fluorescence | Cracks in the □-can: fluorescent proteins from anemonia Sulcata. j. Weidenmann et al., Proc. Natl. Acad. Sci. 2000, 97 (26), 14091–14096 |
| Beta-lactamase | Fluorescence | S. W. Michnick et. al., Nature Biotechnology, 2002, 20, 619–622 |
| Blue fluorescent proteins, BFPs | Fluorescence | Mutant Aequorea victorea fluorescent proteins having increased cellular fluorescence, G. N. Pavlakis et. al., U.S. Pat. No. 6,027,881, Feb. 22, 2000 |
| "Citrine" a novel engineered version of YFP | Fluorescence | Reducing the environmental sensitivity of yellow fluorescent protein, O. Griesbeck et. al., J Biol Chem., 2001, 31, 29188–29194 |
| Cyan fluorescent protein: ECFP and enhanced GFP and YFP: EGFP, EYFP | Fluorescence | Creating new fluorescent probes for cell biology, J. Zhang et. al., Nature Reviews Mol. Cell Biology, 2002, 3, 906–918; R. Y. Tsien, Annu. Rev. Biochem., 1998, 67, 509–544. |
| Dihydrofolate reductase (DHFR) | Fluorescence, binding of fluorophore-methotrexate to reconstituted DHFR | Remy, I. and Michnick, S. W. (2001). Visualization of Biochemical Networks in Living Cells. Proc Natl Acad Sci USA, 98: 7678–7683. |
| DsRed a tetrameric red fluorescent protein from discosoma coral | Fluorescence | Fluorescent proteins from nonbioluminescent anthozoa species. M. V. Matz et. al., Nature Biotechnology, 1999, 17 (10), 969–973 |
| EqFP611 a red fluorescent protein from the sea anemone Entacmaea quadricolor | Fluorescence | A far-red fluorescent protein with fast maturation and reduced oligomerization tendency from Entacmaea quadricolor. J. Wiedenmann et al., Proc. Natl. Acad. Sci. USA 2002, 99(18): 11646–11651 |
| Firefly luciferase | Luminescence, requires D luciferin | Involvement of MAP kinase in insulin signaling revealed by non-invasive imaging of luciferase gene expression in living cells, Rutter et. al., Current Biology, 1995, 5 (8), 890–899; De Wet et. al., Proc. Natl. Acad. Sci., USA 1985, 82, 7870–7873, de Wet et. al., Methods in Enzymology, 1986, 133, 3; U.S. Pat. No. 4,968,613. |
| Gaussia Luciferase, a luciferase isolated from the copepod Gaussia Princeps | Luminescence | Luciferases, fluorescent proteins, nucleic acids encoding the luciferases and fluorescent proteins and the use thereof in diagnostics, high throughput screening and novelty items. U.S. Pat. No. 6,436,682 B1, Aug. 20, 2002 assigned to Prolume, Ltd. |
| GFP | Fluorescence | Protein interactions and library screening with protein Fragment complementation strategies, Remy, J N Pelletier, A. Galarneau, S. W. Michnick, in: Protein-protein interactions: a molecular cloning manual. Cold Spring Harbor Laboratory Press. Chapter 25, 449–475; and U.S. Pat. No. 6,270,964 (Michnick et al.), Protein Fragment complementation assays for the detection of biological or drug interactions. |
| "Kaede" a new fluorescent protein isolated from coral | Fluorescence; green to red photoconversion | An optical marker based on the uv-induced green-red photoconversion of a fluorescent protein, R. |

TABLE I-continued

EXAMPLES of PCA REPORTERS
FOR THE PRESENT INVENTION

| Protein | Nature of Signal | Reference |
|---|---|---|
| m-RFP monomeric red fluorescent protein derived by engineering DsRed. | Fluorescence | Ando et. al., Proc. Natl. Acad. Sci. USA, 2002, 99 (20). 12651–12656 A monomeric red fluorescent protein, R. E. Campbell et. al., Proc. Natl. Acad. Sci. USA, 2002, 99 (12), 7877–7882 |
| Obelin a 22 kd monomeric calcium activated photoprotein | Calcium activated photoprotein also requires coelenterazine luciferin | Formation of the calcium activated photoprotein obelin from apo-obelin and mRNA in human neutrophils, Campbell et. al., Biochem J., 1988, 252 (1), 143–149 |
| PA-GFP a new mutant of YFP | Fluorescence; photoactivatable | A photoactivatable GFP for selective labeling of proteins and cells, G. H,. Patterson et. al., Science, 2002, 297, 1873–1877. |
| Recombinant monomeric glucuroni-dases/glycosi dases | Fluorescence | Such enzymes can produced either by protein engineering of the subunit interface of existing symmetrical multimeric enzymes or suitable naturally occurring monomeric glycosyl hydrolases and detected using cell permeable fluorescent substrates such as e.g. the lipophilic substrate: ImaGene Green C12 FDGlcU available from Molecular Probes; Catalog number I-2908 |
| Reef coral Anthozoan derived GFPs | Fluorescence | Diversity and evolution of the green fluorescent protein family, Y. A. Labas et. al., Proc. Natl. Acad. Sci., USA, 2002, 99(7), 4256–4262,; Fluorescent proteins from nonbioluminescent anthozoa species. M. V. Matz et. al., Nature Biotechnology, 1999, 17 (10), 969–973. |
| Renilla and Ptilosarcus Green fluorescent proteins | Fluorescence | Luciferases, fluorescent proteins, nucleic acids encoding the luciferases and fluorescent proteins and the use thereof in diagnostics, high throughput screening and novelty items. U.S. Pat. No. 6,436,682 B1, Aug. 20, 2002 assigned to Prolume, Ltd. |
| Renilla luciferase. monomeric luminescent photoprotein and Firefly luciferase | Luminescence, renilla luc. requires cell-permeable coelenterazine luciferin. Firefly luc requires D-luciferin. | Optical imaging of renilla luciferase reporter gene expression in living mice, S. Baumik and S. S. Gambhir, Proc. Natl. Acad. Sci., USA 2002, 99 (1), 377–382. This paper also describes use of firefly luc. In vivo. Isolation and expression of a cDNA encoding renilla reniformis luciferase, Lorenz et. al., Proc. Natl. Acad. Sci., USA, 1991, 88, 4438–4442. |
| Renilla luciferase engineered mutant protein (C152A) | Mutant form of Renilla reni-formis luciferase in which the cysteine at position 152 is mutated to alanine, showing a marked increase in bioluminescence due in part to enhanced stability of the mutant enzyme | Improved assay sensitivity of an engineered secreted Renilla luciferase, J. Liu and A. Escher, Gene, 1999, 237: 153–159 |
| SEAP (Secreted alkaline phosphatase) | Fluorescence or luminescence | Secreted placental alkaline phosphatase: a powerful new quantitative indicator of gene expression in eukaryotic cells. Gene, 1988, 66: 1–10 |
| "Venus" a novel engineered of YFP | Fluorescence | A variant of yellow fluorescent protein with fast and efficient maturation for cell-biological applications, T. Nagai et. al., Nature Biotechnology, 2002, 20, 87–90 |
| Renilla mulleri, Gaussia and Pleuromma luciferases | Luminescence | Luciferases, fluorescent proteins, nucleic acids encoding the luciferases and fluorescent proteins and the use thereof in diagnostics, high throughput screening and novelty items. U.S. Pat. No. 6,436,682 B1, Aug. 20, 2002 |
| Oplophorus luciferase | Secreted luciferase from the decapod shrimp Oplophorus | Properties and reaction mechanism of the bioluminescence system of the deep-sea shrimp Oplophorus gracilorostris, O. Shimomura et al., Biochemistry, 1978, 17: 994–998. |
| Vargula Hilgendorfii luciferase | Secreted luciferase from the marine ostracod Vargula Hilgendorfii | Real time imaging of transcriptional activity in live mouse preimplantation embryos using a secreted luciferase. Proc. Natl. Acad. Sci. USA, 1995, 92: 1317–1321. |

The present invention is also directed to a method for drug discovery, said method comprising: (A) constructing one or more protein-fragment complementation assays; (B) testing the effects of chemical compounds on the activity of said assay(s); (C) using the results of said assay(s) to identify chemical compounds with desired activities.

The invention is also directed to a method of screening chemical compounds, said method comprising: (A) constructing protein-fragment complementation assays for one or more steps in a cellular pathway; (B) testing the effects of said compounds on the activity of said assay(s); (C) using the results of said screen to identify compounds that activate or inhibit the cellular pathway(s) of interest.

The present invention is further directed to a method of screening chemical compounds, said method comprising: (A) selecting a chemical library; (B) constructing one or more protein-fragment complementation assay(s); (C) testing the effects of chemical compounds from said library on said assay(s); (C) using the results of said screen to identify specific compounds that increase or decrease the signal generated in said assay(s).

The invention further provides a method of screening chemical compounds, said method comprising: (A) selecting a chemical library; (B) constructing one or more protein-fragment complementation assay(s); (C) testing the effects of chemical compounds from said library on said assay(s); (C) using the results of said screen to identify specific compounds which alter the subcellular location of the signal generated in said assay(s).

The invention is also directed to a method for constructing an assay, said method comprising:
(a) selecting genes encoding proteins that interact;
(b) selecting an appropriate reporter molecule;
(c) effecting fragmentation of said reporter molecule such that said fragmentation results in reversible loss of reporter function;
(d) fusing or attaching fragments of said reporter molecule separately to other molecules;
(e) reassociating said reporter fragments through interactions of the molecules that are fused or attached to said fragments; and
(f) measuring the activity of said reporter molecule with automated instrumentation.

The invention further provides protein fragment complementation assays for drug discovery comprising a reassembly of separate fragments of a reporter molecule wherein reassembly of the reporter fragments generates an optically detectable signal. Additionally, the invention provides protein fragment complementation assays for drug discovery wherein the assay signal is detected with automated instrumentation.

The inventors also provide assay compositions for drug discovery comprising complementary fragments of a first reporter molecule, said complementary fragments exhibiting a detectable activity when associated, wherein each fragment is fused to a separate molecule.

The invention is also directed to an assay composition for drug discovery comprising a product selected from the group consisting of:
(a) a first fusion product comprising:
1) a first fragment of a first reporter molecule whose fragments exhibit a detectable activity when associated and
2) a second molecule that is fused to said first fragment;
(b) a second fusion product comprising
1) a second fragment of said first reporter molecule and
2) a third molecule that is fused to said second fragment; and
c) both (a) and (b).

The present invention is further directed to an assay composition for drug discovery comprising a product selected from the group consisting of:
(a) a first fusion product comprising:
1) a first fragment of a first reporter molecule whose fragments exhibit a detectable activity when associated and
2) a second molecule that is fused to said first fragment;
(b) a second fusion product comprising
1) a second fragment of said first reporter molecule and
2) a third molecule that is fused to said second fragment; and
c) both (a) and (b).

The invention also provides an assay composition for drug discovery comprising a nucleic acid molecule coding for a reporter fragment fusion product, which molecule comprises sequences coding for a product selected from the group consisting of:
(a) a first reporter fusion product comprising:
1) fragments of a first reporter molecule whose fragments can exhibit a detectable activity when associated and
2) a second molecule fused to the fragment of the first molecule;
(b) a second fusion product comprising
1) a second fragment of said first reporter molecule and
2) a second or third molecule; and
(c) both (a) and (b).

In addition, the invention provides an assay composition for drug discovery comprising a product selected from the group consisting of:
(a) a first fusion product comprising:
1) a first fragment of a first reporter molecule whose fragments exhibit a detectable activity when associated and
2) a second molecule that is fused to said first fragment;
(b) a second fusion product comprising
1) a second fragment of said first reporter molecule and
2) a third molecule that is fused to said second fragment; and
(c) a third fusion product comprising:
1) a first fragment of a second reporter molecule whose fragments exhibit a detectable activity when associated and
2) a fourth molecule that is fused to said first fragment;
(d) a fourth fusion product comprising
1) a second fragment of said second reporter molecule and
2) a fifth molecule that is fused to said second fragment; and
e) the combination of (a), (b), (c) and (d).

In a further embodiment, the invention provides an assay composition for drug discovery comprising a nucleic acid molecule coding for a reporter fragment fusion product, which molecule comprises sequences coding for a product selected from the group consisting of:
(a) a first reporter fusion product comprising:
1) fragments of a first reporter molecule whose fragments can exhibit a detectable activity when associated and
2) a second molecule fused to the fragment of the first molecule;
(b) a second fusion product comprising
1) fragments of a second reporter molecule whose fragments can exhibit a detectable activity when associated and
2) a third molecule fused to the fragment of the second molecule; and
(c) both (a) and (b).

Lastly, the invention provides an assay composition for drug discovery comprising an expression vector containing at least one molecule of interest operably linked to a reporter fragment; and an assay composition for drug discovery comprising an expression vector containing (a) an inducible promoter and (b) a gene of interest operably linked to a reporter fragment.

The invention is broadly enabling for drug discovery as it provides a large range of compositions, reporters, formats and assay properties suitable for high-throughput and high-content screening. These assays are straightforward to construct and perform and are cost-effective as well as being biologically relevant. None of these assays require purification of individual proteins, since the proteins of interest are simply expressed in a cell of interest in order to generate an assay. A wide range of the assays provided herein can be constructed by simply subcloning the genes of interest into acceptor sites in suitable expression vectors. Transient assays can be constructed in as little as 24–28 hours from the time of transfection, and renewable, stable cell lines can be created by including selectable markers in the vector cassettes. In sum, the methods, assays and compositions provided herein provide for drug discovery on an unprecedented scale in the biological context of the living cell.

BRIEF DESCRIPTION OF THE DRAWINGS

FIG. 2 shows the DNA damage response pathway and shows high-throughput assays based on beta-lactamase PCA (BLA PCA) and high-content assays based on GFP (GFP PCA) for the Chk1/p53 and p53/p53 interactions. CPT=camptothecin.

FIG. 3(A) shows a luminescent PCA for HTS based on Renilla luciferase (RLuc PCA).

FIG. 3(B) shows induction of the p53/p53 interaction by camptothecin in the RLuc PCA.

FIG. 4 shows a fluorescent, high-content assay based on IFP PCA. Cell images show the inhibitory effect of Geldanamycin and the potentiating effect of Trichostatin A on the p53/p53 interaction in the absence and presence of CPT. The bar graph shows the effects of various known agents on the mean fluorescence in the cell nucleus. Legend to bar graph: 1=vehicle (DMSO); 2=Camptothecin (500 nM CPT); 3=Genistein (12.5 micromolar); 4=Trichostatin A (0.5 micromolar); 5=MS-275 (10 micromolar); 6=LY294002 (25 micromolar); 7=SB 203580 (25 micromolar); 8=HA 14-1 (2 micromolar); 9=Geldanamycin (2.5 micromolar).

FIG. 5(A) depicts the organization of the PI-3-kinase and PKA/PKC-mediated pathways, including a novel interaction between PKB and hFt1 that was identified by cDNA library screening using GFP PCA.

FIG. 5(B) illustrates the effects of activators and inhibitors on the quantity and subcellular locations of the PKB/hFt1 and hFt1/PDK1 complexes in living cells, as detected by a GFP PCA with fluorescence spectrometric detection. 1=COS-1 cells; 2=Jurkat cells; 3=images of COS-1 cells with PCA inside. The dimerization of GCN4/GCN4 leucine zippers was used as a control.

FIG. 6 illustrates (A) the cellular pathway leading to FRAP (FKBP-Rapamycin-Associated Protein); (B) a YFP PCA, enabling visualization of the effects of the drug rapamycin on the interaction of FKBP and mTOR (mTOR is the murine equivalent of FRAP); (C) A dose-response curve for rapamycin in the high-throughput assay.

FIG. 7(A,B) shows the quantitative results of a 96-well plate assay in which gene-by-gene interaction mapping with YFP PCA was performed to identify protein-protein interactions. Assays were read by fluorescence spectrometry.

FIG. 7(C,D) shows scanned images of wells from the high throughput interaction mapping assays of FIG. 7(A,B), including magnified images of the positive PCA control; negative PCA control; and a novel interaction. The subcellular locations of protein-protein complexes can be seen. Images were acquired by automated microscopy.

FIG. 8 illustrates the organization of the pathway leading from the TNF receptor to the cell nucleus, including the IKK (I-kappa-B-Kinase) complex; the NF-kappa-B (NFkB) transcription factor complex (p65/p50), which relocalizes to the nucleus upon TNF stimulation; the cytoplasmic I-kappa-B-alpha (IkBa)/NFkB complex; and the inhibition of NFkB signaling by proteasome inhibitors such as ALLN.

FIG. 9 shows fluorescent PCAs for numerous protein-protein complexes in the TNF pathway, demonstrating correct subcellular localization and showing that multi-color PCAs can be constructed for any protein. Membrane, cytosolic and nuclear complexes are shown from the receptor to the nucleus, and the ubiquitination of proteins is demonstrated.

FIG. 10 shows the results of a high-content PCA for NFkappaB (NFkB, p65/p50) in transiently-transfected cells, demonstrating redistribution of the protein-protein complex in response to TNF and inhibition of the TNF response by the proteasome inhibitor ALLN.

FIG. 11 shows two different stable cell lines with 'PCA inside'.

Figure 1:
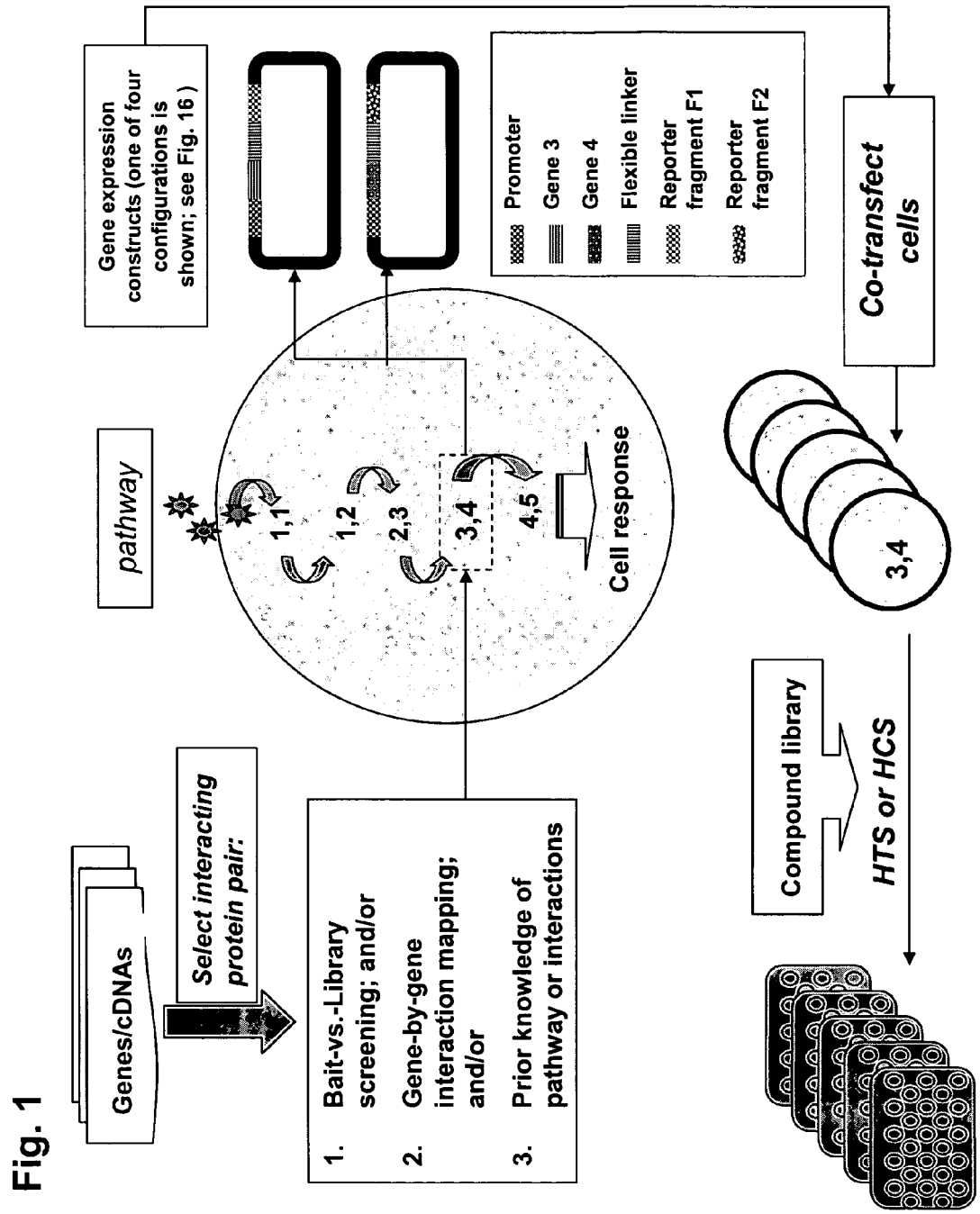
FIG. 1 illustrates the construction of a high-throughput or high-content assay using PCA.

A,B: Induction of nuclear translocation of p65/p50 by TNF;

C,D: No effect of TNF on the control (MEK/ERK) cell line;

E,F: Lack of signal with an individual PCA construct (p65-F[2]), showing that individual PCA fragments are not fluorescent.

FIG. 12(A) shows the TNF dose-response curve and the time course of induction of nuclear translocation of NFkB (p65/p50) in the stable PCA cell line shown in FIG. 11.

FIG. 12(B) shows inhibition of the TNF response by the proteasome inhibitor ALLN in the stable PCA cell line shown in FIG. 11.

FIG. 12(C) shows the further use of the stable PCA cell line from FIG. 11 for high-content screening of a chemical library.

FIG. 12(D) shows a quantitative dose-response curve for a 'hit' from the chemical library screen depicted in FIG. 12(C).

FIG. 13(A) shows another high-content PCA for NFkB translocation in live cells, generating a red fluorescent signal based on DHFR PCA.

FIG. 13(B) shows that the DHFR PCA can also be used to detect inhibition of the nuclear translocation of NFkB by the proteasome inhibitor, ALLN.

FIG. 14 shows a quantitative, fluorescent, high-throughput PCA in a stable cell line for another sentinel in the TNF signaling pathway (IkBa/p65). Images show a reduction in signal in response to TNF, an effect that is blocked by the proteasome inhibitor, ALLN. Panel A shows the TNF dose-response for the IkBa/p65 PCA; Panel B shownns the time-course for the TNF effect on the IkBa/p65 PCA.

FIG. 15 shows the detection and quantitation of ubiquitin-protein complexes with PCA, showing that the proteasome inhibitor ALLN increases the accumulation of ubiquitin-IkBa complexes in the presence of TNF.

FIG. 16 provides an outline of vector construction for examples of PCA vectors suitable for the present invention.

FIG. 17 provides "dual PCAs" in which the construction of an HTS or HCS assay is linked to the generation of a stable cell line. Complementary bicistronic vectors are used to generate a stable cell line, such as with a leucine zipper-directed DHFR PCA, wherein the cell line also contains a fluorescent or luminescent PCA, where the fluorescent or luminescent signal is driven by the interaction of two proteins of interest.

DETAILED DESCRIPTION OF THE INVENTION

Construction of an HTS or HCS assay An overview of the process of constructing an assay for HTS or HCS is shown in FIG. 1. The genes to be used in the HTS or HCS assay may code either for known or for novel interacting proteins. The interacting proteins can be selected by one or methods that include bait-versus-library screening; pairwise (gene by gene) interaction mapping; and/or prior knowledge of a pathway or an interacting protein pair. In the diagram, proteins numbered 3 and 4 are known (or can be shown) to participate in a receptor-mediated cell signaling pathway and can be chosen to construct an HTS or HCS screen to identify compounds that block the pathway. It should be noted that not all protein-protein complexes will be responsive to agonists, antagonists, activators or inhibitors of pathways. Some interactions will be constitutive. It is an advantage of the present invention that PCA can be used to identify protein-protein pairs that serve as 'sentinels' capable of reporting out the activity of a pathway. In either case, once the genes of interest are identified, the assays are constructed according to the following scheme: A reporter fragment pair F1/F2 is generated (a partial list of reporters is in Table 1). Using for example two genes of interest encoding the protein-protein pair denoted as (3,4) in FIG. 1, two expression constructs are made, one comprising gene '3' fused in frame to a flexible linker and to the F1 reporter fragment, and the other comprising gene '4' fused in frame to a flexible linker and to the F2 reporter fragment, in such a way that the gene of interest, linker and reporter fragment are in frame and are operably linked to a promoter. (Polycistronic vectors can also be used. A complete description of vector options is given in Example 12). In FIG. 1 the genes are fused at the 5' end and the encoded proteins of interest will be at the N-terminus of the fusions; other combinations, and details of vector construction and vector elements, are shown in FIG. 16. Cells are co-transfected with complementary F1, F2 gene constructs such that proteins are expressed. Transient assays can be performed; also, stable cell lines can be constructed with "PCA Inside" by using selectable markers or by using a survival selection PCA to generate the stable cell line. The resulting cells or stable cell lines are used for HTS or HCS in conjunction with chemical libraries of interest.

To exemplify these aspect of the present invention, we provide examples for several different cellular pathways including the DNA damage response pathway (Chk1/p53 and p53/p53 as sentinels); the rapamycin-dependent pathway (FKBP/TOR as a sentinel); and the TNF/NFkB signaling pathway (p65/p50, IkB/p65, and IkBa/Ubiquitin as sentinels). We also provide methods and examples of identifying interacting proteins—and determining if they function as constitutive or inducible interactions—by bait-vs.-library screening and/or gene-by-gene interaction mapping. In addition we provide methods and compositions for quantitative, high-content and/or high-throughput assays using a wide range of different PCAs generating fluorescent or luminescent readouts, and we provide specific examples for a GFP PCA and two variants thereof (YFP PCA and IFP PCA); a beta-lactamase PCA (BLA PCA); a luciferase PCA (RLuc PCA); and a dihydrofolate reductase PCA (DHFR PCA). Further, we demonstrate the ability to construct a high-content and/or high-throughput assays and screens for any step in a pathway, and we show examples of the utility of such assays in screening small-molecule and drug libraries to identify compounds that activate or inhibit cellular processes. Finally, we also provide examples of single color assays; multicolor assays; a variety of choices of expression vectors and elements for PCA; and fragment compositions.

Selection of an Appropriate Reporter for PCA

It will be appreciated by a person skilled in the art that the ability to select from among a wide variety of reporters makes the invention particularly useful for drug discovery on a large scale. The principle of PCA makes this possible by enabling the fragmentation of any reporter, including reporters that exist in nature as single (monomeric) proteins. Thus, reporters can be selected that emit light of a specific wavelength and intensity that may be suitable for a range of protein expression levels, cell types, and detection modes. The flexibility is an important feature of the invention because of the wide range of biological processes and biochemical targets of interest for drug discovery. For some proteins, activation of a pathway—for example, by a receptor agonist or a drug—leads to an increase or decrease in the formation of protein-protein complexes without a change in the subcellular location of the complexes. An increase or decrease in the number of protein-protein complexes formed by the proteins leads to an increase or decrease, respectively, in the signal generated by the PCA. In that case, a high-throughput assay format can be used to measure the bulk fluorescent signal that reflects the amount of the complex of interest. Examples are shown herein for three different pathways in which the selected pathway sentinels were Chk1/p53, p53/p53, PKB/hFt1, PDK1/hFt1, FKBP/TOR (FRAP), IkBa/p65, and IkBa/Ubiquitin. For other proteins, such as NFkB (p50/p65), activation of a pathway leads to the change in the amount of a protein-protein complex from one subcellular compartment versus another (membrane vs. cytosol, cytosol vs. nucleus, etc). In the latter case, a high-content assay format can be used to localize the fluorescent signal generated by the reassembled reporter at the site of the protein-protein complex within the cell.

In several embodiments of the present invention, monomeric enzymes are used to construct PCAs. DHFR was used to construct a fluorescence assay based on the high-affinity binding of methotrexate (MTX) to the reassembled DHFR. When fluorophore-conjugated methotrexate is used and the excess unbound MTX is washed out of the cells, the amount and subcellular location of protein-protein complexes can be determined. Different spectral properties can be achieved by varying the flurophore attached to the MTX. In the present invention the DHFR PCA was used to construct a high-content assay for NFkB translocation in order to identify agents that block the TNF pathway.

In another example of the present invention, the reporter used to construct a high-throughput assay is beta-lactamase (BLA). The BLA PCA has been described previously and in the present invention it was used, in conjunction with a novel cephalosporin substrate, to construct a fluorescent high-throughput assay for inhibitors of the DNA damage response pathway acting on p53 and its upstream elements.

In another embodiment of the present invention, the reporter used to construct a high throughput assay is luciferase. The use of luciferase in PCA was first described by Michnick et al. (U.S. Pat. No. 6,270,964). In the present invention Renilla luciferase (RLuc) PCA was chosen to construct a high-throughput assay for inhibitors of the DNA damage response pathway, generating an assay with a robust signal that can be read in minutes with high throughput instrumentation. Mutant RLuc fragments are also provided for improved stability.

In another embodiment of the present invention, intrinsically fluorescent proteins such as GFP are used to construct PCAs. A GFP PCA was first described by Michnick et al. (U.S. Pat. No. 6,270,964). PCAs based on GFP or variants thereof are particularly suitable for HCS since the signal is located at the site of fragment complementation. The fluorescent proteins, including GFP, YFP, CFP and other variants as well as the newer reporters listed in Table 1 are particularly useful for the present invention, because no additional cofactors or substrates are needed for signal generation. PCAs based on these proteins are particularly useful for high-content assays, since the signal is localized at the site of the protein-protein complex. Examples are shown for PCAs based on GFP and two mutants thereof (YFP and 'IFP'). These assays can be read either with high-content instrumentation such as automated fluorescence microscopes or automated confocal imaging systems; or, in some cases where a particular assay pair results in an overall increase or decrease in fluorescence intensity, the change in bulk fluorescence can be read with high-throughput instrumentation as shown in FIG. 6.

Reporters generating a high quantum yield are often preferable for reasons of sensitivity; for example, the YFP PCA gives a brighter signal than the GFP PCA in the same way as the full-length YFP protein gives a brighter signal than the full-length GFP protein, and the mutant (IFP) fragments produce a brighter signal than the corresponding YFP fragments. For any reporter of interest various useful PCA fragments can be created using the methods taught in U.S. Pat. No. 6,270,964 (Michnick et al.), and the fragments can be further engineered to generate a brighter signal upon fragment reassembly. In the present application, protein fragments were generated either by PCR or were generated synthetically (by oligonucleotide synthesis) to create fragments with the desired assay properties. PCA fragments that reconstitute enzymes can be used in conjunction with various substrates or probes to generate assays with different spectral properties. In the present invention, a beta-lactamase PCA is used in conjunction with a cephalosporin substrate to generate a blue fluorescent product that can be read on a microtiter plate reader. Similarly, a DHFR PCA is used in conjunction with a Texas Red-MTX probe to generate a red fluorescent signal that can be detected by automated microscopy. Mutant versions of luciferase such as C152A (Table 1) have been described and can be used in conjunction with the present invention. It will be obvious to one skilled in the art that standard techniques of genetic engineering can be applied to create useful variants of any reporter fragments for PCA.

Multicolor PCAs allow the monitoring of more than one cellular process or pathway simultaneously, for example to determine if a compound of interest is affecting more than one pathway in the same cell or simply to multiplex assays for reasons of efficiency and cost savings. The ability to perform multicolor measurements enables the use of internal assay controls, for example where the controls give a red fluorescent signal while the proteins of interest give a yellow fluorescent signal. In the present invention, a multicolor PCA is demonstrated in which a DHFR PCA (red fluorescence) is combined in the same cells with a YFP PCA (yellow fluorescence) allowing the visualization of distinct protein-protein complexes with different subcellular locations. The wide range of forms of GFP, including the yellow, cyan, citrine, SEYFP, Venus, and red homologues of GFP, are all suitable for PCA and can be further engineered to improve the signal intensity of the fragments used in the present invention. The numbers and kinds of assay readouts are limited only by the ability of the instrumentation to resolve different wavelengths of emitted light. Many other multicolor assays can be constructed using the principles and methods taught in the present invention.

Other reporters suitable for PCA are described in Table 1 and in Michnick et al. (U.S. Pat. No. 6,270,964) and include monomeric enzymes and fluorescent, luminescent or phosphorescent proteins. Also, PCAs based on fragments of antigens or antibodies can be created and used in conjunction with simple detection schemes. For example, PCAs based on fragments of a non-native antigen could be constructed such that a protein-protein interaction results in reconstitution of an epitope that can be detected with an antigen conjugated to a detectable moiety such as biotin or fluorescein. Similarly, PCAs based on fragments of an antibody could be constructed such that a molecular interaction results in reconstitution of a functional antibody that binds to an antigen conjugated to a detectable moiety such a fluorophore. Any of these and similar reporters can be used, and modifications thereof, in conjunction with the present invention.

EXAMPLE 1

Fluorescent and Luminescent Assays for HTS and HCS

In the first example of the present invention, we sought to demonstrate the construction of a wide range of useful assays based on fluorescent and luminescent PCAs and to demonstrate their use for high-throughput and high-content assays in conjunction with standard HTS and HCS instrumentation. We used elements of the DNA damage response pathway.

FIG. 2 shows a scheme of the pathway and the results for an HTS assay based on a beta-lactamase PCA (BLA PCA) and a HCS assay based on a GFP PCA. FIG. 3 shows an HTS assay based on Renilla luciferase (RLuc PCA). FIG. 4 shows a high-content assay based on an IFP PCA (IFP is a variant of GFP). In these examples, the proteins assayed are interacting pairs in the DNA damage response pathway, specifically, the checkpoint kinase Chk1 which interacts with the tumor suppressor p53 (Chk1/p53 PCA), or p53 itself which forms homodimers (p53/p53 PCA).

For the BLA PCA, the genes of interest—which were known to be involved in DNA damage response pathways—were fused to BLA reporter fragments, and co-transfected in pairs (in 6 replicates) into HEK293E cells. Specifically, interactions between two key proteins, p53 and the checkpoint kinase, Chk1, were evaluated for their response to the DNA damaging agent camptothecin (CPT) and various known drugs or compounds. Full length cDNAs (sequence verified) encoding p53 [NM_000546] and Chk1 [NM_001274] were amplified by PCR and the resulting fragments fused in-frame to the 3'-end of BLA[1] or BLA[2] through a flexible 10 amino acid linker. The resulting BLA[1]-p53, BLA[2]-p53, and BLA[2]-Chk1 constructs contained an EBNA-1 origin for episomal replication in HEK293E cells, but no selectable markers for long term maintenance in cell culture. All constructs were sequenced to confirm the integrity of the reporter-gene fusion prior to use in assays. Approximately 36–40 hours after transfection, HEK293E cells co-transfected with 250 ng DNA (total) of BLA[1]-p53 and BLA[2]-Chk1 fusions (or with BLA[1]-p53 and BLA [2]-p53) were treated for two hours with 300 nM camptothecin, followed by treatment with or without known inhibitors of the catalytic activity of Chk1 (e.g. 10 micromolar DBH and 50 micromolar Go6976), or an inhibitor of the upstream ATR kinase (2 mM caffeine). After two hours (or up to 6 hours) the drugs were removed and a beta-lactamase substrate was added (FIG. 2B). The substrate was a derivative of a previously-described cephalosporin (Quante et al.; see References). Hydrolysis of the beta-lactam ring by reconstituted BLA releases free coumarin which has a blue fluorescence. After drug treatment, cells were washed with 200 microliters of PBS (plus calcium and magnesium), then covered with 25 microliters of PBS without calcium or magnesium. Freshly diluted BLA substrate was added to each well to a final concentration of 20 micromolar in 2% DMSO (in a final volume of 50 microliters). For each protein pair, the rate of hydrolysis of the substrate was determined immediately after addition of substrate by a kinetic assay on a Molecular Devices Gemini XS plate reader. Accumulated fluorescent substrate was excited at 345 nm and detected at 440 nm every 10 minutes for a 90 minute period. Data plotted in the bar graph in FIG. 2(A) represent the mean rate of hydrolysis for each condition, with error bars depicting 95% confidence intervals for the mean measurement. As can be seen in FIG. 2(A), significant effects of the two Chk1 inhibitors, DBH and Go6976, can be detected for the interaction between Chk1 and p53.

Assays Using GFP for PCA

In order to confirm the interactions quantified with BLA PCA and to assess their subcellular localization, the same DNA damage response elements were used to construct a GFP PCA, and the subcellular locations of the complexes were imaged by fluorescence microscopy (FIG. 2A, left panels). The full-length cDNAs encoding p53 and Chk1 were amplified by PCR. The fusion genes were subcloned into pCDNA3.1 expression vectors (Invitrogen) with Zeocin selectable marker for GFP[1]-p53 and hygromycin marker for GFP[2]-Chk1 and GFP[2]-p53. A flexible 10-amino acid linker consisting of (GGGGS)$_2$ (SEQ ID No.1) separated the genes of interest and the YFP fragments. The use of a flexible linker between the gene of interest and the reporter fragment assures that the orientation and arrangement of the fusions is optimal to bring the protein fragments into close proximity (J. N. Pelletier, F.-X. C.-Valois & S. W. Michnick, 1998, Proc Natl Acad Sci USA 95: 12141–12146). GFP[1] corresponds to amino acids 1 to 158 and GFP[2] corresponds to amino acids 159 to 239 of GFP and was amplified by PCR from pCMS-EGFP (Clontech).

Twenty-four hours prior to transfection, HEK293T cells were seeded at 10,000 cells/well in a 48-well cell culture dish (Costar). Cells were transfected with 150 ng total DNA comprised of GFP[1]-p53 and GFP[2]-Chk1, or GFP[1]-p53 and GFP[2]-p53 using FuGene (Roche) as per the manufacturer's recommendations. After approximately 48 hours of expression, cells were rinsed once in PBS, then overlaid with 75 microliters of PBS (with no counterstain) for fluorescence microscopy. Live cells were imaged on an SP Nikon fluorescence microscope using a Chroma FITC filter (excitation: 460–500 nm; emission: 505–560 nm; dichroic mirror: 505LP).

Luminescent PCAs for HTS

We also sought to demonstrate the use of a luminescent assay based on protein-fragment complementation (PCA). Fragments of Renilla luciferase (RLuc) were designed using methods as described by Michnick et al. (U.S. Pat. No. 6,270,964). We chose to create synthetic oligonucleotides corresponding to fragmentation of the intact RLuc at glutamic acid residue 160 (E160). It should be noted that alternative fragmentation sites could also be used; hence, the present invention is not limited to the particular fragments used herein. Codons engineered into fragments to create start/stop codons are underlined. It should be noted that if the protein fragment is at the 5' end of the construct, it will be preceded by an initiating methionine (atg codon), whereas if the fragment is at the 3' end of the construct, the gene of interest will be preceded by the initiating methionine (atg codon)). Therefore, the present invention covers not only F1 fragments that have a naturally occurring initiating methionine, but also the same F1 fragments that have been modified to remove the initiating methionine when the F1 fragment is to be at the 3' end of the construct. Similarly, the invention covers F2 fragments that naturally do not begin with an initiating methionine, but also those same F2 fragments that have been modified to include an initiating methionine when the F2 fragment is to be at the 5' end of the construct.

We created two different RLuc PCAs. The first RLuc PCA was based on wild-type Renilla luciferase and the fragments had the following sequences:

RLuc fragment 1 nucleotide sequence (SEQ ID No. 2)
atggcttccaaggtgtacgaccccgagcaacgcaaacgcatgatcactggg cctcagtggtgggctcgctgcaagcaaatgaacgtgctggactccttcatc aactactatgattccgagaagcacgccgagaacgccgtgattttctgcat ggtaacgctgcctccagctacctgtggaggcacgtcgtgcctcacatcgag cccgtggctagatgcatcatccctgatctgatcggaatgggtaagtccggc aagagcgggaatggctcatatcgcctcctggatcactacaagtacctcacc gcttggttcgagctgctgaaccttccaaagaaaatcatctttgtgggccac gactgggggcttgtctggcctttcactactcctacgagcaccaagacaag atcaaggccatcgtccatgctgagagtgtcgtggacgtgatcgagtcctgg gacgagtggcctgacatcgag<u>taa</u>

RLuc fragment 1 translation (amino acid sequence)

(SEQ ID No. 3)
MASKVYDPEQRKRMITGPQWWARCKQMNVLDSFINYYDSEKHAENAVIFL

HGNAASSYLWRHVVPHIEPVARCIIPDLIGMGKSGKSGNGSYRLLDHYKY

LTAWFELLNLPKKIIFVGHDWGACLAFHYSYEHQDKIKAIVHAESVVDVI

ESWDEWPDIE*

RLuc fragment 1 nucleotide sequence, without initiating "atg"

(SEQ ID No. 4)
gcttccaaggtgtacgaccccgagcaacgcaaacgcatgatcactgggcct cagtggtgggctcgctgcaagcaaatgaacgtgctggactccttcatcaac tactatgattccgagaagcacgccgagaacgccgtgattttctgcatggt aacgctgcctccagctacctgtggaggcacgtcgtgcctcacatcgagccc gtggctagatgcatcatccctgatctgatcggaatgggtaagtccggcaag agcgggaatggctcatatcgcctcctggatcactacaagtacctcaccgct -continued
tggttcgagctgctgaaccttccaaagaaaatcatctttgtgggccacgac tgggggcttgtctggcctttcactactcctacgagcaccaagacaagatc aaggccatcgtccatgctgagagtgtcgtggacgtgatcgagtcctgggac gagtggcctgacatcgag<u>taa</u>

RLuc fragment 1 translation (amino acid sequence)
without initiating M (SEQ ID No. 5)
ASKVYDPEQRKRMITGPQWWARCKQMNVLDSFINYYDSEKHAENAVIFLHG

NAASSYLWRHVVPHIEPVARCIIPDLIGMGKSGKSGNGSYRLLDHYKYLTA

WFELLNLPKKIIFVGHDWGACLAFHYSYEHQDKIKAIVHAESVVDVIESWD

EWPDIE*

RLuc fragment 2 nucleotide sequence (SEQ ID No. 6)
<u>atg</u>gaggatatcgccctgatcaagagcgaagagggcgagaaaatggtgctt gagaataacttcttcgtcgagaccatgctcccaagcaagatcatgcggaaa ctggagcctgaggagttcgctgcctacctggagccattcaaggagaagggc gaggttagacggcctacccctctcctggcctcgcgagatccctctcgttaag ggaggcaagcccgacgtcgtccagattgtccgcaactacaacgcctacctt cgggccagcgacgatctgcctaagatgttcatcgagtccgaccctgggttc ttttccaacgctattgtcgagggagctaagaagttccctaacaccgagttc gtgaaggtgaagggcctccacttcagccaggaggacgctccagatgaaatg ggtaagtacatcaagagcttcgtggagcgcgtgctgaagaacgagcagtaa RLuc fragment 2 translation (amino acid sequence)

(SEQ ID No. 7)
<u>M</u>EDIALIKSEEGEKMVLENNFFVETMLPSKIMRKLEPEEFAAYLEPFKEKG

EVRRPTLSWPREIPLVKGGKPDVVQIVRNYNAYLRASDDLPKMFIESDPGF

FSNAIVEGAKKFPNTEFVKVKGLHFSQEDAPDEMGKYIKSFVERVLKNEQ*

RLuc fragment 2 nucleotide sequence without
initiating "atg"

(SEQ ID No. 8)
gaggatatcgccctgatcaagagcgaagagggcgagaaaatggtgcttgag aataacttcttcgtcgagaccatgctcccaagcaagatcatgcggaaactg gagcctgaggagttcgctgcctacctggagccattcaaggagaagggcgag gttagacggcctacccctctcctggcctcgcgagatccctctcgttaaggga ggcaagcccgacgtcgtccagattgtccgcaactacaacgcctaccttcgg gccagcgacgatctgcctaagatgttcatcgagtccgaccctgggttctttt ccaacgctattgtcgagggagctaagaagttccctaacaccgagttcgtg aaggtgaagggcctccacttcagccaggaggacgctccagatgaaatgggt aagtacatcaagagcttcgtggagcgcgtgctgaagaacgagcagtaa RLuc fragment 2 translation (amino acid sequence)
without initiating M (SEQ ID No. 9)
EDIALIKSEEGEKMVLENNFFVETMLPSKIMRKLEPEEFAAYLEPFKEKG

EVRRPTLSWPREIPLVKGGKPDVVQIVRNYNAYLRASDDLPKMFIESDPGF

FSNAIVEGAKKFPNTEFVKVKGLHFSQEDAPDEMGKYIKSFVERVLKNEQ*

Additionally, we created a mutant RLuc PCA having a single mutation (C124A) in the F1 fragment. Liu and Escher (Gene 237 (1999) pp 153–159) described a secreted mutant form of RLuc in which a C152A (SRUC3) mutant showed enhanced activity. In our RLuc there is no signal sequence at the N terminus, therefore the C152A mutation corresponds to C124A assuming numbering from a translated start codon. Liu and Escher showed that this mutation in the secreted protein greatly enhanced the signal intensity making it particularly useful for HTS. Thus, in the present invention we also present a novel F1 fragment for PCA (RL1[C124A]) having the following sequence:

RLuc(C124A) fragment 1 nucleotide sequence (SEQ ID No. 10)
atggcttccaaggtgtacgaccccgagcaacgcaaacgcatgatcactggg cctcagtggtgggctcgctgcaagcaaatgaacgtgctggactccttcatc aactactatgattccgagaagcacgccgagaacgccgtgatttttctgcat ggtaacgctgcctccagctacctgtggaggcacgtcgtgcctcacatcgag cccgtggctagatgcatcatccctgatctgatcggaatgggtaagtccggc aagagcgggaatggctcatatcgcctcctggatcactacaagtacctcacc gcttggttcgagctgctgaaccttccaaagaaaatcatctttgtgggccac gactgggggct<u>gct</u>ggcctttcactactcctacgagcaccaaga caagatcaaggccatcgtccatgctgagagtgtcgtggacgtgatcgagtc ctgggacgagtggcctgacatcgag<u>taa</u>

RLuc(C124A) fragment 1 translation (amino acid
sequence)

(SEQ ID No. 11)
MASKVYDPEQRKRMITGPQWWARCKQMNVLDSFINYYDSEKHAENAVIFL

HGNAASSYLWRHVVPHIEPVARCIIPDLIGMGKSGKSGNGSYRLLDHYKY

LTAWFELLNLPKKIIFVGHDWGA<u>A</u>LAFHYSYEHQDKIKAIVHAESVVDVI

ESWDEWPDIE*

RLuc(C124A) fragment 1 nucleotide sequence without
initiating "atg"

(SEQ ID No. 12)
gcttccaaggtgtacgaccccgagcaacgcaaacgcatgatcactgggcct cagtggtgggctcgctgcaagcaaatgaacgtgctggactccttcatcaac tactatgattccgagaagcacgccgagaacgccgtgatttttctgcatggt aacgctgcctccagctacctgtggaggcacgtcgtgcctcacatcgagccc gtggctagatgcatcatccctgatctgatcggaatgggtaagtccggcaag -continued

```
agcgggaatggctcatatcgcctcctggatcactacaagtacctcaccgct tggttcgagctgctgaaccttccaaagaaatcatctttgtgggccacgac tgggggctgctctggcctttcactactcctacgagcaccaagacaagatc aaggccatcgtccatgctgagagtgtcgtggacgtgatcgagtcctgggac gagtggcctgacatcgagtaa
```

RLuc(C124A) fragment 1 translation (amino acid sequence) without initiating M (SEQ ID No. 13)
ASKVYDPEQRKRMITGPQWWARCKQMNVLDSFINYYDSEKHAENAVIFLHG

NAASSYLWRHVVPHIEPVARCIIPDLIGMGKSGKSGNGSYRLLDHYKYLTA

WFELLNLPKKIIFVGHDWGAALAFHYSYEHQDKIKAIVHAESVVDVIES

WDEWPDIE*

Either the wild type RLuc F1 or the mutant RLuc F1(C124A) can be used in combination with the RLuc F2 fragment provided above to generate luminescent PCAs. The following examples below show the results obtained with the wild-type RLuc fragments. The F1 and F2 fragments described above were created by oligonucleotide synthesis (Blue Heron Biotechnology, Bothell, Wash.) and were designated RL[1] (aa 1–160) and RL[2] (aa 161–311). The synthetic fragments were amplified by PCR to incorporate restriction sites and a linker sequence encoding a flexible 10 amino acid peptide linker in configurations that would allow fusion of a gene of interest to either the 5'- or 3'-end of each reporter fragment sequence. The amplified fragments of RL[1] and RL[2] were then subcloned into a mammalian expression vector (pcDNA3.1Z, Invitrogen), creating 4 independent vectors (an N-terminal, and C-terminal fusion vector for each reporter fragment) as shown in FIG. 16.

STAT1/PDK2 served as a negative control PCA. The full coding sequences for p53, STAT1 and PDK2 were amplified by PCR from sequence verified full-length cDNAs. The resulting PCR products were desalted, digested with appropriate restriction enzymes to allow directional cloning, and fused in-frame to either the 5' or 3'-end of RL[1], RL[2], RL[3] or RL[4] through a linker encoding a flexible 10 amino acid peptide (GGGGS)$_2$ (SEQ ID No.1) to assure that the orientation/arrangement of the fusions in space is optimal to bring the fluorescent protein fragments into close proximity. DNAs from recombinant constructs were isolated using Qiagen Turbo BioRobot Prep kits (Qiagen, Chatsworth, Calif.) on a Beckman FX robotic workstation (Beckman Coulter, Fullerton, Calif.). Isolated DNAs were quantitated and then normalized to a concentration of 50 ng/microliter.

The luciferase PCA was constructed to quantify the homo-dimerization of p53 (p53/p53 PCA) and compared to a negative control RLuc PCA (Pdk2/STAT1). The latter proteins do not interact. Twenty-four hours prior to transfection, HEK293T cells were plated (10,000 cells per well for 24 hr assay, 15,000 cells per well for 48 hr assay) in 96-well plates coated with poly-lysine. Cells were transfected with 0.1 microgram of total DNA (50 ng of each reporter construct) using Fugene transfection reagent (Roche Diagnostics, Indianapolis, Ind.), as per the manufacturer's recommendations. Following 24 or 48 hrs of expression, cells were washed once with PBS, then lysed with 20 microliters of Renilla Luciferase Assay Lysis Buffer (Promega, Cat # E2810). Each lysate was added to a well of a 96-well plate, and 100 µl of Renilla Luciferase Assay buffer containing a proprietary formulation of the Renilla luciferase substrate coelenterazine (Promega, Cat # E2810) was added by injector in a Thermo Lab Systems Luminoskan Ascent luminometer. For each sample, the luminescence released was captured over 10 seconds, with a 2 second delay after addition of substrate to the sample. Data are reported as relative luminescence units (RLU), and have not been normalized to protein content.

FIG. 3(A) shows the luminescence generated from whole cell lysates of HEK293T cells expressing p53/p53 or Pdk2/STAT1 fused to fragments of Renilla luciferase after 24 and 48 hours of expression. The figure legend identifies the orientation of the encoded proteins relative to each reporter fragment. The results demonstrate that fragmentation of Renilla luciferase at E160 results in an efficient PCA; all four possible fusion pairs produced detectable luminescence at 24 and 48 hrs of expression. The signal was higher 48 hours after transfection than at 24 hours after transfection.

It is important to note that the Pdk2/STAT1 PCA produced a negligible signal. This is a key point because it demonstrates that the PCA signal in the assay is absolutely dependent upon the presence of two interacting proteins fused to the complementary PCA fragments; the fragments themselves are incapable of reassembling into an active enzyme unless the complementation is assisted by the proteins fused to the complementary fragments. This key feature highlights the distinction between the present invention and alternative protein-protein interaction technologies such as FRET or BRET, where proteins of interest are expressed as fusions to active, full-length fluorescent or luminescent proteins. In addition this feature highlights the distinction between the present invention and high-content assays based on single-protein tagging with a luminophore such as GFP. In the latter cases, individual proteins generate a signal, even in the absence of a protein-protein interaction.

As shown in FIG. 3, the p53/p53 complex produced a signal ranging from 20 RLU to over 200 RLU, depending on the gene-fragment orientations, resulting in a signal-to-background as high as 200:1 in the RLuc PCA. To demonstrate the effect of camptothecin in the assay, twenty-four hours prior to transfection, HEK293T cells were plated (15,000 cells per well) in a 96-well plate coated with poly-lysine. For each condition tested, cells were transfected in quadruplicate with 0.1 microgram of total DNA (50 ng each of RL[1]-p53 and RL[2]-p53) using Fugene transfection reagent as above. Four wells were mock transfected (with transfection reagent, but no PCA constructs) to serve as a control for background contributed by coelenterazine autofluorescence. After 30 hours of expression, for each PCA, quadruplicate wells were treated with 0.1% DMSO or 500 nM camptothecin (CPT: Calbiochem) for 18 hours. Drug was removed by washing two times with PBS, and cell lysates were prepared as described above prior to performing a Renilla Luciferase luminescence detection assay (Promega). In FIG. 3(B), each bar represents the mean of four independent samples, with error bars representing the standard deviation for those measurements. A statistically significant increase (27%) in luminescence was observed for the CPT-treated p53:p53 PCA, relative to the same PCA treated with vehicle alone (0.1% DMSO). The same treatment had no effect on the negative control (Pdk2:STAT1).

The results demonstrate that the luciferase PCA represents a sensitive, high-throughput assay. The RLuc PCA can be applied to HTS for a large number of proteins and therapeutic targets in whole cell assays or cell lysates. Luciferase PCAs can be constructed in high-throughput and ultra-high-throughput formats due to the exquisite sensitivity of the assay. These assays can be scaled up to 1536-well formats or even higher, and an entire plate can be read within minutes. In addition, mutant versions of luciferase PCAs can be created, taking advantage of genetic engineering to introduce mutations such as C152A which has been shown to increase the luminescent output of the Renilla luciferase holoenzyme (see Table 1 for references).

As we showed previously with a DHFR PCA and as for the RLuc PCA described above, site-directed mutagenesis, random mutagenesis methods, and/or combinatorial synthetic methods can be used to generate novel PCA fragments for any suitable reporter, using methods that are well known to one skilled in the art. A further example of this aspect of the present invention is provided below.

Construction of a YFP PCA and an IFP PCA

In order to obtain high-content assays with brighter signals than with the GFP PCA, we generated two different mutant versions of GFP fragments, both resulting in yellow fluorescence. The sequence of the first fragment pair corresponded to a full-length EYFP. Full-length EYFP has been shown to have improved spectral properties relative to full length GFP (Tavare et al. 2001, Journal of Endocrinology 170: 297–306). The PCAs described here were first created by introducing the EYFP-specific mutations S65G, S72A and T203Y (24) into existing oligonucleotide fragments of EGFP, resulting in fragments designated YFP[1] and YFP[2] corresponding to amino acids 1–158 and 159–239 of the full-length EYFP (21, 25). Subsequently, assays were constructed by starting directly with synthetic oligonucleotides corresponding to YFP[1] and YFP[2] (Blue Heron). Fragments YFP[1] and YFP[2] had the following compositions:

YFP[1] nucleotide sequence (SEQ ID No.14)
atggtgagcaagggcgaggagctgttcaccggggtggtgcccatcctggtc gagctggacggcgacgtaaacggccacaagttcagcgtgtccggcgagggc gagggcgatgccacctacggcaagctgaccctgaagttcatctgcaccacc ggcaagctgcccgtgccctggcccaccctcgtgaccaccttcggctacggc ctgcagtgcttcgcccgctaccccgaccacatgaagcagcacgacttcttc aagtccgccatgcccgaaggctacgtccaggagcgcaccatcttcttcaag gacgacggcaactacaagacccgcgccgaggtgaagttcgagggcgacacc ctggtgaaccgcatcgagctgaagggcatcgacttcaaggaggacggcaac atcctggggcacaagctggagtacaactacaacagccacaacgtctatatc atggccgacaagcagtaa YFP fragment 1 translation (amino acid sequence)

(SEQ ID No. 15)
MVSKGEELFTGVVPILVELDGDVNGHKFSVSGEGEGDA

TYGKLTLKFICTTGKLPVPWPTLVTTFGYGLQCFARYPDHMKQHDFFKSA

MPEGYVQERTIFFKDDGNYKTRAEVKFEGDTLVNRIELKGIDFKEDGNIL

GHKLEYNYNSHNVYIMADKQ

YFP[1] nucleotide sequence without initiating "atg"

(SEQ ID No.16)
Gtgagcaagggcgaggagctgttcaccggggtggtgcccatcctggtcgag ctggacggcgacgtaaacggccacaagttcagcgtgtccggcgagggcgag ggcgatgccacctacggcaagctgaccctgaagttcatctgcaccaccggc aagctgcccgtgccctggcccaccctcgtgaccaccttcggctacggcctg cagtgcttcgcccgctaccccgaccacatgaagcagcacgacttcttcaag tccgccatgcccgaaggctacgtccaggagcgcaccatcttcttcaaggac gacggcaactacaagacccgcgccgaggtgaagttcgagggcgacaccctg gtgaaccgcatcgagctgaagggcatcgacttcaaggaggacggcaacatc ctggggcacaagctggagtacaactacaacagccacaacgtctatatcatg gccgacaagcagtaa YFP fragment 1 translation (amino acid sequence) without initiating M (SEQ ID No. 17)
VSKGEELFTGVVPILVELDGDVNGHKFSVSGEGEGDATYGKLTLKFICTTG

KLPVPWPTLVTTFGYGLQCFARYPDHMKQHDFFKSAMPEGYVQERTIFFKD

DGNYKTRAEVKFEGDTLVNRIELKGIDFKEDGNILGHKLEYNYNSHNVYIM

ADKQ

YFP fragment 2 nucleotide sequence (SEQ ID No.18)
atgaagaacggcatcaaggtgaacttcaagatccgccacaacatcgaggac ggcagcgtgcagctcgccgaccactaccagcagaacacccccatcggcgac ggccccgtgctgctgcccgacaaccactacctgagctaccagtccgccctg agcaaagaccccaacgagaagcgcgatcacatggtcctgctggagttcgtg accgccgccgggatcactctcggcatggacgagctgtacaagtaa YFP fragment 2 translation (amino acid sequence)

(SEQ ID No. 19)
MKNGIKVNFKIRHNIEDGSVQLADHYQQNTPIGDGPVLLPDNHYLSYQSAL

SKDPNEKRDHMVLLEFVTAAGITLGMDELYK

YFP fragment 2 nucleotide sequence without initiating "atg"

(SEQ ID No.20)
aagaacggcatcaaggtgaacttcaagatccgccacaacatcgaggacggc agcgtgcagctcgccgaccactaccagcagaacacccccatcggcgacggc cccgtgctgctgcccgacaaccactacctgagctaccagtccgccctgagc aaagaccccaacgagaagcgcgatcacatggtcctgctggagttcgtgacc gccgccgggatcactctcggcatggacgagctgtacaagtaa YFP fragment 2 translation (amino acid sequence) without initiating M (SEQ ID No. 21)
KNGIKVNFKIRHNIEDGSVQLADHYQQNTPIGDGPVLLPDNHYLSYQSAL

SKDPNEKRDHMVLLEFVTAAGITLGMDELYK

These fragments were further mutated for additional experiments, to create an even more intense PCA "IFP PCA". Mutations were selected based on the YFP variant designated SEYFP-F46L (Venus). These mutations have been shown to accelerate the maturation of the fluorescent signal in the intact protein (T. Nagai et al., 2002, "A variant of yellow fluorescent protein with fast and efficient maturation for cell-biological applications", Nature Biotech. 20: 87–90). PCR mutagenesis was employed to incorporate the additional mutations F46L into SEYFP[1], and V163A and S175G into YFP[2], resulting in novel fragments we designated IFP[1] and IFP[2].

IFP fragment 1 nucleotide sequence (SEQ ID No.22)
atggtgagcaagggcgaggagctgttcaccggggtggtgcccatcctggtc gagctggacggcgacgtaaacggccacaagttcagcgtgtccggcgagggc gagggcgatgccacctacggcaagctgaccctgaagttGatctgcaccacc ggcaagctgcccgtgccctggcccaccctcgtgaccaccCtcggctacggc ctgcagtgcttcgcccgctaccccgaccacatgaagcagcacgacttcttc aagtccgccatgcccgaaggctacgtccaggagcgcaccatcttcttcaag gacgacggcaactacaagacccgcgccgaggtgaagttcgagggcgacacc ctggtgaaccgcatcgagctgaagggcatcgacttcaaggaggacggcaac atcctggggcacaagctggagtacaactacaacagccacaacgtctatatc aCggccgacaagcagtaa IFP fragment 1 translation (amino acid sequence)

(SEQ ID No.23)
MVSKGEELFTGVVPILVELDGDVNGHKFSVSGEGEGDATYGKLTLKLICT

TGKLPVPWPTLVTTLGYGLQCFARYPDHMKQHDFFKSAMPEGYVQERTIF

FKDDGNYKTRAEVKFEGDTLVNRIELKGIDFKEDGNILGHKLEYNYNSHN

VYITADKQ

IFP fragment 1 nucleotide sequence without initiating "atg"

(SEQ ID No.24)
gtgagcaagggcgaggagctgttcaccggggtggtgcccatcctggtcgag ctggacggcgacgtaaacggccacaagttcagcgtgtccggcgagggcgag ggcgatgccacctacggcaagctgaccctgaagttGatctgcaccaccgg caagctgcccgtgccctggcccaccctcgtgaccaccCtcggctacggcc tgcagtgcttcgcccgctaccccgaccacatgaagcagcacgacttcttca agtccgccatgcccgaaggctacgtccaggagcgcaccatcttcttcaagg acgacggcaactacaagacccgcgccgaggtgaagttcgagggcgacaccc tggtgaaccgcatcgagctgaagggcatcgacttcaaggaggacggcaaca tcctggggcacaagctggagtacaactacaacagccacaacgtctatatca Cggccgacaagcagtaa IFP fragment 1 translation (amino acid sequence) without initiating M (SEQ ID No.25)
VSKGEELFTGVVPILVELDGDVNGHKFSVSGEGEGDATYGKLTLKLICT

TGKLPVPWPTLVTTLGYGLQCFARYPDHMKQHDFFKSAMPEGYVQERTIF

FKDDGNYKTRAEVKFEGDTLVNRIELKGIDFKEDGNILGHKLEYNYNSHN

VYITADKQ

IFP fragment 2 nucleotide sequence (SEQ ID No.26)
atgaagaacggcatcaaggCgaacttcaagatccgccac aacatcgaggacggcGgcgtgcagctcgccgaccactaccagcagaacacc cccatcggcgacggccccgtgctgctgcccgacaaccactacctgagctac cagtccgccctgagcaaagaccccaacgagaagcgcgatcacatggtcctg ctggagttcgtgaccgccgcgggatcactctcggcatggacgagctgtac aagtaa IFP fragment 2 translation (amino acid sequence)

(SEQ ID No.27)
MKNGIKANFKIRHNIEDGGVQLADHYQQNTPIGDGPVLLPDNHYLSYQSAL

SKDPNEKRDHMVLLEFVTAAGITLGMDELYK*

IFP fragment 2 nucleotide sequence without initiating "atg"

(SEQ ID No.28)
aagaacggcatcaaggCgaacttcaagatccgccacaacatcgaggacggc

Ggcgtgcagctcgccgaccactaccagcagaacacccccatcggcgacggc cccgtgctgctgcccgacaaccactacctgagctaccagtccgccctgagc aaagaccccaacgagaagcgcgatcacatggtcctgctggagttcgtgacc gccgcgggatcactctcggcatggacgagctgtacaagtaa IFP fragment 2 translation (amino acid sequence) without initiating M (SEQ ID No.29)
KNGIKANFKIRHNIEDGGVQLADHYQQNTPIGDGPVLLPDNHYLSYQSAL

SKDPNEKRDHMVLLEFVTAAGITLGMDELYK*

Open reading frames of full-length human p53 were fused in-frame to the 5'-end of IFP[1] and the 3'-end of IFP[2] to generate the following constructs in a pcDNA3.1 (Invitrogen) backbone: p53-IFP[1] and IFP[2]-p53. The final p53-IFP[1] construct contained a Zeocin selectable marker, while the IFP[2]-p53 construct contained a hygromycin selectable marker. All fusions were through a flexible linker encoding a 10-amino acid peptide (GlyGlyGlyGlyGlySer)$_2$, also referred to throughout as (GGGGS)$_2$ (SEQ ID No.1). DNAs from recombinant constructs were isolated on a Beckman FX robotic workstation (Beckman Coulter, Fullerton, Calif.) using Qiagen Turbo BioRobot Prep kits or manually using Qiagen Midi Prep kits. Isolated DNAs were quantitated and then normalized to a concentration of 50 ng/microliter.

Approximately 24 hours prior to transfection cells were seeded into 96 well poly-D-Lysine coated plates (Greiner) using a Multidrop 384 peristaltic pump system (Thermo Electron Corp., Waltham, Mass.) at a density of 7,500 cells per well. A total of 100 ng of DNA (p53–IFP[1] and IFP[2]-p53) was co-transfected using Fugene 6 (Roche) according to the manufacturer's protocol. Cells expressing the PCA pair in the absence of stimulation were incubated with medium containing drugs for 30 minutes, 90 minutes, and 8 hours. Alternatively, cells stimulated with camptothecin (CPT) were pre-treated with drugs for 2 hours, then incubated with 500 nM CPT for an additional 16 hours in the presence of the following test compounds that were known or suspected to affect the p53 pathway: CPT, genistein, Trichostatin A, MS-275, LY294002, SB203580, HA14-1, or Geldanamycin, at the concentrations indicated in the Legend to FIG. 4. Following drug treatment cells were simultaneously stained with 33 µg/ml Hoechst 33342 (Molecular Probes) and 15 µg/ml TexasRed-conjugated Wheat Germ Agglutinin (TxR-WGA; Molecular Probes), and fixed with 2% formaldehyde (Ted Pella) for 10 minutes. Cells were subsequently rinsed with HBSS (Invitrogen) and kept in the same buffer during image acquisition. Fluorescence resulting from IFP PCA was captured using the Discovery-1automated fluorescence imager (Molecular Devices, Inc.) equipped with a robot arm (CRS Catalyst Express; Thermo Electron Corp., Waltham, Mass.). Images were acquired for YFP fluorescence (excitation filter: 480/40 nm; emission filter 535/50 nm), Hoechst fluorescence (excitation filter: 360/40 nm; emission filter 465/30 nm), and Texas Red fluorescence (excitation filter: 560/50 nm; emission filter 650/40 nm). Within each well four unique populations of cells were imaged to yield a total of 8 images of each fluorochrome per treatment condition.

Representative images of drug effects on the p53:p53 PCA are shown in FIG. 4. The left panel of three images corresponds to effects of geldanamycin or Trichostatin A on the PCA in the absence of CPT, while the right panel shows effects of the same drugs in the presence of 500 nM camptothecin. DMSO (top images) is the vehicle used to resuspend the drugs.

Geldanamycin is a known inhibitor of Hsp90, a chaperone protein for a number of cellular proteins, including wild type and mutant p53 (King et al. 2001). The expected effect of this drug would be to decrease the stability of p53, therefore decreasing the signal, as we observed. The results demonstrate that Hsp90 inhibitors can be detected by constructing a PCA in which at least one member of the PCA pair is an Hsp90 client protein. These assays will enable large-scale screening for additional Hsp90 client proteins, for example by constructing PCAs for a large number of protein-protein complexes and testing the PCA in the absence and presence of geldanamycin to identify proteins that are sensitive to Hsp90 inhibition. Moreover, such assays can be used immediately in HTS to identify small-molecule inhibitors of Hsp90 activity. Since geldanamycin and its derivative, 17-AAG, have potent anti-tumor activity, the ability to construct assays that are sensitive to Hsp90 inhibition enables a new area of anti-cancer drug discovery.

Trichostatin A is an inhibitor of histone deacetylase I (HDAC1). Inhibition of deacetylation in the presence of camptothecin should induce acetylation of p53, therefore stabilizing the protein and increasing its transcriptional activity. Using PCA, we observed a dramatic increase in p53:p53 PCA signal in the presence of camptothecin which was greater with this 16-hour CPT pretreatment than with the shorter CPT pretreatments shown in FIGS. 2 and 3, respectively. Therefore, these assays can be used to screen for novel inhibitors of HDACs, a further important area of cancer biology.

Automated image analysis was performed using Image J freeware to quantitate the level of fluorescence contributed by the PCA in each image. For the p53:p53 PCA, background contributed by cellular auto-fluorescence was subtracted from each image, then the mean pixel fluorescence intensity was determined within the nucleus of each cell. In FIG. 4, the derived value, nuclear mean (Y-axis), is plotted for each drug treatment (X-axis). Quantitative values for the unstimulated PCA are shown in mauve, with data from the CPT-stimulated assay shown in blue. Consistent with the images in FIG. 4, the HDAC inhibitors Trichostatin A and MS-275 significantly stimulated the p53/p53 interacton above the control in the presence of CPT. A similar effect was seen with the BCL-2 inhibitor, HA14-1. The kinase inhibitors LY 294002 (PI3K) and SB 203580 (p38 MAPK) caused an increased association in both assays. Geldanamycin significantly inhibited both assays, as shown in the images and the associated histogram. These assays will be useful in screening chemical libraries for novel agents that modulate the DNA damage response.

EXAMPLE 2

Identifying Novel Protein-protein Interactions and Constructing Quantitative Assays The PCA strategy described in the invention and depicted in FIG. 1 was next used to identify novel protein-protein interactions in the PI-3-kinase and PKA/PKC-mediated pathways and then to carry out quantitative screens based on the novel interactions. First, cDNA library screening was performed with the GFP PCA in order to identify proteins interacting with PKB. A novel interaction between PKB and Ft1 was identified by the GFP PCA screen. Subsequently, the GFP PCA was used to construct fluorescent assays for PKB/Ft1 and PDK1/Ft1. The organization of the pathways and the position of the PKB/hFt1 interaction is shown in FIG. 5(A). Methods for library screening with PCA and for assay construction are provided below.

DNA Constructs. The full-length cDNAs encoding PKB, PDK1, PKCalpha, the catalytic subunit of PKA (PKAc), GSK3beta, BAD, Caspase 9 and FKHRL1 were amplified by PCR and subcloned into the eukaryotic expression vector pMT3 [Kaufman, 1989 #23], 5' of the F[2] fragment of GFP. GFP[1] corresponds to amino acids 1 to 158 and GFP[2] to amino acids 159 to 239 of GFP and was amplified by PCR from pCMS-EGFP (Clontech). The PKB-GFP[2] fusion was also inserted in a pMT3 vector where the ampicillin resistance gene has been replaced by a chloramphenicol resistance gene (pMT3-chloramphenicol) for the purpose of the cDNA library screen. In all cases, a 10 amino acid flexible linker consisting of (GGGGS)$_2$ (SEQ ID No.1) was inserted between the cDNA and the GFP fragments to assure that the orientation/arrangement of the fusions in space is optimal to bring the protein fragments into close proximity. The GFP [1]-GCN4 and GCN4-GFP[2] constructs consist of fusions with GCN4 leucine zipper-forming sequences and are used as controls. For the GFP PCA-based cDNA library screen, a human brain cDNA library was excised from the vector pEXP1 (ClonCapture cDNA library, Clontech) using SfiI restriction sites and inserted into the pMT3 vector, 3' of the F[1] fragment of GFP and a 10 amino acids flexible linker. The PCA-cDNA library fusion expression vectors were divided into several pools (according to the size of the inserted cDNAs—from 0.5 to 4.6 kb) and amplified at 30° C. in liquid medium.

Cell Lines

COS-1 cells were grown in DMEM (Life Technologies) supplemented with 10% fetal bovine serum (FBS, Hyclone). The human Tag-Jurkat T cell line expresses the SV40 large T antigen and harbor an integrated β-galactosidase reporter plasmid where three tandem copies of the NF-AT binding site directs transcription of the lacZ gene. They were grown in RPMI-1640 (Life Technologies) supplemented with 10% FBS, 1 mM sodium pyruvate and 10 mM Hepes.

cDNA Library Screening with PCA to Identify Novel Protein-protein Interactions. COS-1 cells were plated in 150-mm dishes 24 h before transfection. Cells were transfected (10 μg DNA total/dish) using Lipofectamine reagent (Life Technologies), at around 60% confluence, with pMT3 vector harboring the human brain cDNA library fused to the F[1] fragment of GFP (GFP[1]-cDNA library) and pMT3-chloramphenicol vector containing the full-length PKB fused to the F[2] fragment of GFP (PKB-GFP[2]). The GFP[1]-cDNA library fusions were transfected in several pools, according to their size. 48 h after transfection, positive clones (reconstitution of GFP from its fragments) were collected on a fluorescence-activated cell sorter (FACS) analyzer (FACScalibur, Becton Dickinson). The total DNA from each pool of positive cells was extracted (DNeasy tissue kit, Qiagen), transformed in DH5-alpha bacterial cells and plated on LB-agar containing 100 μg/ml ampicillin (no propagation of the chloramphenicol-resistant vector harboring the PKB-F[2] fusion). DNA plasmids containing the F[1]-cDNA fusions were extracted from individual clones and retransfected separately with PKB-GFP[2] or GFP[2] alone (negative control) to discard negative clones that enter the pool during the cell sorting. After this second round of selection, the DNA plasmids corresponding to the positive clones were submitted to sequence analysis.

COS-1 cells were split in 12-well plates 24 h before transfection. Cells were transfected, at around 60% confluence, with different combinations of the pMT3 plasmid harboring the various DNA constructs (1 microgram total DNA/well), using Lipofectamine reagent (Life Technologies) according to the manufacturer's instructions. Tag-Jurkat T cells were transfected at 1×10$^6$ cells/well (2 micrograms total DNA/well) using DMRIE-C reagent (Life Technologies). The amounts of DNA transfected in each experiment were kept constant by adding empty vector. For Tag-Jurkat T cells, the next day, 1 microgram/ml PHA and 50 ng/ml PMA were added to the growth medium to enhance promoter activity and gene expression. 48 h after transfection, COS-1 cells were washed one time with PBS, gently trypsinized and resuspended in 200 microliters of PBS. Tag-Jurkat T cells were directly harvested and resuspended in 200 microliters of PBS. The relative amount of reconstituted GFP, a measure of the interaction between the fused protein partners, was detected by fluorometric analysis. The total cell suspensions were transferred to 96-well black microtiter plates (Dynex, VWR Scientific) and subjected to fluorometric analysis (Spectra MAX GEMINI XS, Molecular Devices). Cells co-expressing GFP[1]-hFt1 and PKB-GFP[2] or GFP[1]-hFt1 and PDK1-GFP[2] fusions were treated with agonists, antagonists and inhibitors as follows. 48 hours after transfection, COS-1 cells were washed two times with PBS, incubated for 5 h in serum-free medium and untreated or treated with 300 nM wortmannin or 50 micromolar LY294002 (Calbiochem) for the last hour. Afterward, cells were stimulated for 30 min with 10% serum or 20 μg/ml insulin (Roche Diagnostics). Tag-Jurkat T cells were treated for 90 min with 300 nM wortmannin or 30 min with 5 μg/ml anti-CD3 antibody or 5 μg/ml phytohemagglutinin (PHA) or 1 micromolar ionomycin or 10 micromolar forskolin or/and 500 nM phorbol-12-myristate-13-acetate (PMA) (all from Calbiochem) prior to fluorometric analysis. Afterward, the data were normalized to total protein concentration in cell lysates (Bio-Rad protein assay). The constitutive dimerization of GCN4 leucine zipper was used as a positive control. The background fluorescence intensity corresponding to non-transfected cells was subtracted from the fluorescence intensities of all of the samples. The subcellular location of the hFt1/PKB and hFt1/PDK1 protein-protein complexes was also determined by fluorescence microscopy in live cells. For fluorescence microscopy, COS-1 cells were grown on 18-mm glass cover slips prior to transfection. Cells were washed two times with PBS and mounted on glass slides. Fluorescence microscopy was performed on live cells with a Zeiss Axiophot microscope (objective lens Zeiss Plan Neofluar 100×/1.30).

Panel 1 of FIG. 5(B) shows the quantitative fluorescence results obtained with the PCAs in COS cells and panel 2 shows the results obtained in Jurkat cells. Panel 3 of FIG. 5(B) shows the images of protein-protein complexes and their subcellular locations. Agents that stimulated the pathway caused an increase in fluorescence, whereas compounds that inhibit the pathway caused a decrease in fluorescence of the protein-protein complexes in the pathway. For example, in COS cells, serum and insulin caused an increase in the amount of the PKB/hFt1 and PDK1/hfT1 complexes and a redistribution of the protein-protein complexes from the cytosol to the membrane, effects that could be blocked by the PI3-kinase inhibitors wortmannin and LY294002. These results demonstrate that the PKB/hFT1 and PDK1/hFt1 are sentinels of pathway activity and that PCA can be used to construct quantitative assays suitable for detection by standard fluorescence instrumentation and microscopy. Moreover, these assays will be useful in the identification of novel compounds that activate or inhibit the insulin- and serum-mediated pathways.

EXAMPLE 3

High-throughput Assays with YFP PCA

We next sought to demonstrate that PCAs can be used as quantitative assays providing relevant pharmacological information. For the example we used the well-characterized interaction of FKBP (the FK506 binding protein) and its cognate partner, FRAP (FKBP-Rapamycin-Associated-Protein), an interaction that occurs only at a low level in untreated cells but which is markedly induced by the immunosuppressant drug, rapamycin. The organization of the human growth pathway, showing the 'sentinel' FKBP/FRAP interaction, is depicted in FIG. 6A.

For these studies, we used a YFP PCA. HEK 293E Cells were seeded into a 96 well plates at a cell density of 13,000 per well. Cell media is MEM-alpha Growth medium. Total volume was 100 microliters. Cells were allowed to grow 20–24 hours prior to transfection—cells were 70–80% confluent at time of transfection. Cells were maintained at 37C, 5% CO2. Cells were transfected with a total of 0.1 micrograms of DNA per well using Fugene (Roche). HEK 293 cells expressing FKBP-YFP[1] and mTOR-YFP[2] were treated with increasing doses of rapamycin as follows. At 24 hours post-transfection, 100 microliters of fresh media was added to each well and incubated an additional 20–24 hours prior to rapamycin induction at 37° C., 5% CO2. 100 µl of media containing the appropriate dilution of rapamycin was added to each well. The plate was then incubated for 2.5 hours in a tissue culture incubator (37° C., 5% CO2). Each well was then rinsed with 200 microliters HBSS (pre-warmed to 37° C.) and 100 microliters of HBSS was added per well. The plate was returned to the tissue culture incubator for 1 hour prior to reading on the platereader at an excitation of 485 nm and emission at 527 nm.

FIG. 6 shows the results of the assay, demonstrating effects of rapamycin on the interaction of FKBP and mTOR (mTOR is the murine equivalent of the human protein FKBP-rapamycin associated protein, FRAP). Rapamycin induced the formation of complex between FKBP and mTOR which could be seen by microscopy (FIG. 6B) and quantitated by fluorescence spectroscopy (FIG. 6C) in 96 well plates using excitation and emission wavelengths of 485 and 527 nm, respectively. Such assays can be used in combination with a variety of small-molecule, natural product, combinatorial, peptide or siRNA libraries to identify molecules that activate or inhibit the protein-protein complex, either by acting directly on the protein-protein interaction, or by acting upstream of the PCA sentinel.

EXAMPLE 4

Gene-by-gene Interaction Mapping with PCA

FIG. 1 shows that protein-protein interactions can be identified by various methods, including gene-by-gene interaction mapping. To further demonstrate that aspect of the present invention, and to show that PCA can be applied systematically to identify interacting proteins in high throughput, a gene-by-gene interaction map was performed to identify novel protein-protein interactions. Gene-by-gene interaction mapping provides an alternative to bait-vs.-library screening in cases where it is desirable to test defined sets of genes against each other, or for purposes of assay optimization. In addition, gene-by-gene interaction mapping enables testing of full-length proteins for interactions with other full-length proteins. To demonstrate this principle, randomly-selected full-length cDNAs in YFP PCA constructs designed according to FIG. 16 were pooled robotically as YFP[1]/YFP[2] pairs in in 96-well format plates, and 50 ng of each DNA pool was transfected into HEK293T cells using FuGene transfection reagent. Each 96-well microtiter plate of cells contained 28 PCAs representing different protein-protein pairings, as wells as four sets of controls (one positive and 3 negative controls), all run in triplicate. Forty-eight hours after transfection, cells were incubated briefly with Hoescht 33342 to obtain a cell count for each well for normalization purposes. Fluorescence intensity measurements are obtained on a Molecular Devices plate reader using separate settings appropriate for YFP or Hoechst. Data are exported for statistical analyses and stored in a relational database. Interactions that are statistically different from the negative control are sorted by significance level (as determined by the Student's t-test) and mean fluorescence units.

Out of 641 assays analyzed, there was an 88.8% concordance rate between the data acquired by the platereader assay, and image data acquired on a microscope. FIG. 7(A,B) shows the results of two plates from the screen. Each plate contains 28 different PCAs representing different gene pairings, in addition to four sets of controls (one positive and three negative controls), all assayed in triplicate (represented on the x-axis). The y-axis shows the mean fluorescence intensity measurement for each PCA, with error measurements plotted as 95% confidence intervals. The positive control was p65/p50 and the negative control was PDK1/PDK1. For each plate, the negative controls are highlighted in red and the positive control in yellow. Interactions that are statistically different from the negative control are color-coded as in the legend, indicating the level of statistical significance associated with each measurement, as determined by the Student t-test of the mean fluorescence. Note that the y-axes in panels A and B are different, displaying the range of signal intensities that can be obtained in this assay relative to the positive control. The assay can be used to identify protein-protein complexes within pathways of interest for drug discovery in HTS or HCS formats or to optimize gene pair orientations for assay development.

FIG. 7(C) shows the images of cells in individual wells as acquired by automated microscopy. After quantifying the fluorescence intensity of YFP PCAs on the plate reader as for FIG. 7A and 7B, images were acquired from the same 96-well plates on the Discovery-1 imaging system (Universal Imaging). The Hoechst-stained cells of a control well (cells stained blue in FIG. 7D) were used to establish the appropriate focal plane for image acquisition across the entire plate. Images were then acquired at two sites in each well, using a 10× objective at wavelengths appropriate for Hoechst and YFP, respectively. The merged view across an entire plate is visible in panel C. Examples of positive and negative controls, as well as a 'novel' positive are shown in panel D. Information can be obtained regarding subcellular localization patterns, as can be seen with the predominantly cytoplasmic localization of a 'novel' protein-protein interaction in panel D. It should be noted that the interaction mapping shown in FIG. 7 was performed with "universal vectors" having the same linker lengths, promoters, and reporter fragments. This enables semi-automated subcloning of the full-length cDNAs and eliminates the need for custom vector construction for each assay. DNAs showing a positive signal could be further characterized, for example, by the addition of pathway activators and inhibitors as was shown for the novel hFt1/PKB interaction in the example of FIG. 5. The advantage of the present invention is therefore the ability to rapidly map protein-protein interactions and to simultaneously characterize the interactions in living cells in high-throughput and/or high-content assays; and subsequently, to use the same PCA constructs to develop robust, stable high-throughput screens for molecules that activate or inhibit the pathways for which the protein complexes represented in the PCAs.

Mapping, Characterizing and Screening a Series of Targets within a Signaling Pathway We therefore sought to apply PCA to the construction of assays for a large number of individual steps in a well-characterized cellular signaling pathway and to carry these assays into screening of chemical libraries. FIG. 8 illustrates the organization of the pathway leading from the TNF receptor to the nucleus, including the role of the NFkB transcription factor complex (p65/p50). Binding of TNF to its receptor leads to activation of the IKK complex, resulting in the phosphorylation and degradation of IkBa by the proteasome. Degradation of IkBa frees the NFkB transcription factor complex (p65/p50) to translocate from the cytoplasm into the nucleus, where it can turn on the transcription of pro-inflammatory genes. Proteasome inhibitors, such as ALLN and epoxomicin (and the current anti-cancer drug, Velcade®) block the degradation of IkBa, resulting in the retention of NFkB in the cytosol.

Anti-TNF and anti-proteasome strategies have proven therapeutic efficacy in the treatment of inflammation and cancer, respectively. As a result, there is considerable interest in identifying novel small-molecule inhibitors of the TNF pathway that could serve as the basis for novel orally available drugs. We used this prototypical pathway to demonstrate the following aspects of the present invention: (1) the use of the invention to map protein components of signaling pathways and construct 'sentinel' assays that report pathway activity; (2) the use of the invention for high-content and/or high-throughput assays for a sequence of events in a signaling cascade, regardless of protein function or subcellular context; (3) the use of the invention either for transient assays or to generate stable cell lines with 'PCA Inside'; (4) the use of the invention with different reporters and readouts for assay construction, including single- and multi-color assays; (5) the use of the invention in detecting and quantifying pathway activation and inhibition; and (6) the use of the invention in screening small-molecule libraries to identify inhibitors with potential therapeutic properties.

EXAMPLE 5

Visualizing Individual Protein-protein Complexes within Living Cells

Following the general scheme shown in FIG. 1, a series of PCAs were constructed with full-length cDNAs encoding known elements of the TNF pathway and using a DHFR PCA (red fluorescence) and/or the YFP PCA (yellow/green fluorescence) (FIG. 9). For the PCA constructs, open reading frames of p65, p50, CBP, CBPnt, TNFRI, TRAF2 and a single coding unit of Ubiquitin were PCR amplified, fused in-frame to complementary fragments of DHFR or YFP, and subcloned into pCDNA3.1zeo. The REFSEQ or GENBANK identifiers for the genes used are: NM009045 (p65/RelA), NM003998 (NFkB1/p50), AY033600, NM004380 (CBP), NM003824 (FADD), NM003789 (TRADD), BC033810 (TRAF2), XM032491 (IKKbeta), BC000299 (IKKgamma), and Ubiquitin C (BC039193). CBPnt [(S66385 (1.2313)] corresponds to the amino terminal 771 amino acids of CBP. Ubiquitin C corresponds to the 76 kDa ubiquitin monomer.

Methods of assay construction were as follows. The DHFR fragments, F[1,2] and F[3], correspond to murine DHFR residues 1 to 105 and 106–186, respectively (Pelletier, Campbell-Valois et al. 1998). For the DHFR PCAs, the DNAs encoding the proteins of interest were ligated to either the 5' or 3' end of DHFR-F[1,2] and DHFR-F[3] to generate N or C terminal fusions, respectively. A flexible linker consisting of $(GGGGS)_3$ (SEQ ID No.30) separated the genes of interest and the DHFR fragments. For transient expression of DHFR PCA constructs, 8×10e4 CHO DUKXB11 (DHFR-deficient) cells were seeded into 12 well plates and co-transfected 24 hours later with 1 microgram of DNA per well comprising a 1:1 molar ratio of the complementary pairs of fusion constructs, using Fugene (Boehringer Mannheim) according to the manufacturer's instructions. Forty-eight hours post-transfection, the cells were incubated with 4 micromolar Texas Red-Methotrexate (Molecular Probes/Invitrogen) for two hours at 37C in growth medium (alpha-MEM, 10% fetal bovine serum). When two proteins of interest interact, TxR-MTX binds to reconstituted DHFR. Unbound TxR-MTX was removed by rinsing followed by a 30-minute incubation in fresh medium. Cells were viewed and images acquired using a Nikon Eclipse TE1000 fluorescence microscope at excitation and emission wavelengths of 580 nm and 625 nm, respectively.

For the YFP PCAs, the open reading frames of the selected cDNAs were fused in-frame to complementary YFP fragments separated by a 10-amino acid flexible linker as described above. HEK293T cells (Invitrogen) were seeded into poly-L-lysine coated 96-well plates at a density of 1.5×10e4 cells/well and transfected 24 hours later with 100 ng DNA per well comprising a 1:1 molar ratio of the complementary pairs of fusion constructs. Forty-eight hours post-transfection, cells were rinsed with PBS and viewed using a Discovery-1 automated microscope (Universal Imaging/Molecular Devices) at excitation and emission wavelengths of 485 nm and 527 nm, respectively.

A number of proteins known to participate in the TNF signaling pathway formed protein-protein complexes in live cells that were readily detectable by PCA; some of these are shown in FIG. 9. Fluorescent signals shown in yellow/green represent YFP PCAs whereas signals shown in red represent DHFR PCAs. Robust fluorescent signals and correct subcellular localization of selected protein-protein complexes could be detected by PCA in the transiently-transfected cells. Complexes observed by PCA include all previously established interactions, including TNFRI/TNFRI, TNFRI/FADD, TRADD/FADD, TRADD/TRAF2, FADD/TRAF2; IKK complex subunits IKKbeta/IKKgamma, various IKK proteins with the adaptors TRADD, FADD and TRAF2; IKKgamma/TNFRI, IKKbeta/IkappaBalpha, IKKgamma/IkBalpha, IkBa/p65, IkBa/p50, and NFkB subunits p65 and p50 as homo- and hetero-dimeric complexes; and ubiquitin complexes such as IkBa/Ubiquitin (Ub). In addition, we observed previously unreported interactions between p50, p65 and IkBa with upstream adaptor molecules TRADD, FADD, and TRAF2. These adaptor proteins are recruited to the TNF receptor upon ligand-mediated receptor trimerization. Their interaction with the transcription factors suggests the existence of a multi-subunit complex that consists of proteins involved in distal steps of the signaling cascade. Subcellular locations of complexes were consistent with their known functions in the cell. For example, the TNF receptor is comprised of three identical subunits that self-associate to form complexes which are clearly located at the plasma membrane (TNFR1/TNFR1). The predominantly cytoplasmic protein complexes TRAF2/IkBa, TRAF2/p65, IkBa/p65, IKKbeta/IKKgamma and p65/p50; and the predominantly nuclear CBP/CBP and CBP/p65 complexes were clearly observed by PCA. In addition, we were able to directly observe ubiquitination by constructing a PCA with the DNA encoding the Ubiquitin monomer fused to one fragment of YFP and the full length cDNA for IkBa fused to a complementary fragment of YFP. This represents the first direct visualization of ubiquitinated proteins in living cells and, to our knowledge, no other technology enables direct detection of ubiquitin-protein complexes.

EXAMPLE 6

Multicolor Assays

The ability to construct PCAs with different reporters, each generating a distinct fluorescent signal, also enables multicolor assay construction. As a proof of this principle, /p65 complexes were visualized with YFP PCA (yellow/green) in cells simultaneously expressing CBP/p65 complexes (red) as detected by the DHFR PCA. CHO cells were concurrently transfected with DHFR reporter fusions DHFR-F[1,2]-CBPnt and p65-DHFR-F[3], and YFP reporter fusions IkBa-YFP[1] and YFP[2]-p65 as described above. 48 hours after transfection, cells were stained with TxR-MTX and visualized by microscopy as described for the DHFR PCA and the YFP PCA, respectively. As shown in FIG. 9, the signal generated by the IkBa/p65 complex is localized in the cytosol (yellow/green signal produced by YFP PCA) whereas the signal generated by the CBP/p65 is clearly localized in the nucleus (red signal produced by DHFR PCA with Texas Red).

This example highlights the distinction between the present invention and previous studies of p65, that rely upon tagging p65 with an intact GFP (e.g. J A Schmid et al., 2000, Dynamics of NFkB and IkBa studied with green fluorescent protein (GFP) fusion proteins, J. Biol. Chem. 275 (22): 17035–17042). In the latter case, what is studied is the subcellular compartmentation of p65 alone. With PCA, as shown in FIG. 9, what is studied is the interaction of p65 with different proteins (IkBa and CBP) in different subcellular compartments (cytosol and nucleus, respectively). Because p65 interacts with distinct proteins at sequential steps of the TNF signaling cascade, the use of PCA enables high-fidelity detection of TNF induced signal transduction. In addition, the ability to construct multi-color, multiparametric analyses with PCA provides a flexible approach enabling a wide range of basic research in cell biology, biochemistry and signal transduction; as well as an extraordinary degree of flexibility and efficiency in assay design and development.

Constructing high-content and high-throughput assays in living cells. Three of the assays in the TNF pathway (p50/p65, p65/ and IkBa/Ubiquitin) were used to demonstrate that PCA enables the detection of dynamic pathway activation and inhibition in living cells. As depicted in FIG. 1, the principle of these assays is that a pathway is actually a series of steps involving the physical association, dissociation or movement of proteins within complexes. These events occur in real time and within specific subcellular compartments in the living cell. The present invention enables the construction of assays to measure these dynamic events for any protein within any pathway. We demonstrate this aspect of the present invention by constructing assays for three different sentinels and showing that the readout is a sensitive indicator of pathway activity. In the case of the IkBa/p65 complex, activation of the TNF pathway results in the degradation of IkBa by the proteasome. As a result, the total fluorescence resulting from the IkBa/p65 complexes decreases upon TNF treatment, an effect that can be blocked by proteasome inhibitor. In the case of the NFkB (p65/p50) transcription complex, activation of the TNF pathway results in the release of p65 from inhibition by IkBa. Consequently, the p65/p50 complex redistributes from the cytosol into the nucleus. Pretreatment with proteasome inhibitor blocks the degradation of IkBa such that the NFkB complex is retained in the cytosol. The latter assays can be read in high-content mode using PCAs capable of detecting the subcellular location of the complexes. In the case of IkBa/Ubiquitin, proteasome inhibitors which block the degradation of IkBa lead to an accumulation of IkBa/Ubiquitin complexes. The latter assays can be read in high-content (automated microscopy or automated imaging) or high-throughput (bulk fluorescence) formats.

Any or all of these assays will be useful in screening for inhibitors of TNF signaling. A screening campaign based on a high-content assay for p50/p65 is described in detail below. In particular these assays will be useful in identifying agents with anti-inflammatory activity and/or with anti-cancer activity. The three 'sentinel' PCAs studied in further detail all were sensitive detectors of proteasome inhibitors such as ALLN. Finally, the ability to detect ubiquitination of proteins enables large-scale screening for proteins that are degraded by ubiquitination. Sensitive and specific assays for such compounds are of particular interest in the pharmaceutical industry since the marketed drug Velcade®, which is a proteasome inhibitor, has potent anti-tumor activity.

EXAMPLE 7

High-content Assays for NFkB Translocation

To demonstrate that PCA can be used to detect pathway activation and inhibition in living cells, we first constructed a transient high-content assay to measure the nuclear translocation of the p65/p50 complex in response to TNF-alpha and to assess inhibition by ALLN. Fusion genes were subcloned into pCDNA3.1 expression vectors (Invitrogen) with a Zeocin selectable marker for YFP[1]-p50, and a hygromycin marker for YFP[2]-p65. A linker consisting of $(GGGGS)_2$ (SEQ ID No.1) separated the genes of interest and the YFP fragments. CHO DUKXB11 cells were seeded into 96 well plates at a density of 8×10e3 cells/well and transfected 24 hours later with YFP[1] and YFP[2] fusion genes at a 1:1 molar ratio using Fugene (Boehringer Mannheim) according to manufacturer's directions. A total of 20 ng DNA per well was used for each sample. Thirty-six hours post-transfection, cells were serum starved by incubation in 0.25% FBS-supplemented aMEM for an additional 16–18 hours. For cytokine induction, certain cells were treated with 25 ng/ml mTNF (Boehringer Mannheim) for 30 min. To examine the effect of proteasome inhibition on NFkB nuclear translocation, the serum-starved cells were treated with 40 micrograms/ml ALLN (Calbiochem) for 1 hour prior to and during the mTNF alpha induction period. The cells were rinsed with PBS and the subcellular location of NFkB complexes was visualized and images acquired using a Nikon Eclipse TE2000 fluorescence microscope at excitation and emission wavelengths of 485 nm and 527 nm, respectively. Quantitative analysis of fluorescence intensities was performed using Metamorph software (Universal Imaging, Molecular Devices, Inc.)

FIG. 10 shows results of a transient assay for NFkB (p65/p50) cytoplasmic-to-nuclear translocation in CHO cells based on YFP PCA. In the absence of TNF the p65/p50 complexes were evenly distributed between the cytosol and nucleus. In TNF-treated cells the ratio of nuclear:cytoplasmic fluourescence increased by an average of two-fold and the p65/p50 complexes could be visualized in the nucleus of live cells by fluorescence microscopy. We sought to demonstrate inhibition of the nuclear translocation of NFkB by the well-characterized proteasome inhibitor, ALLN. CHO cells transiently co-expressing complementary YFP fragment fusions of p50 and p65 were incubated in the absence or presence of TNF. Where indicated, cells were pre-treated with the proteasome inhibitor ALLN. Mean fluorescence intensities in the nucleus and cytoplasm of each cell were measured and expressed as a ratio. ALLN inhibited the TNF-induced cytoplasmic-to-nuclear translocation of NFkB complexes in the YFP PCA assay. While the effects of cytokine and inhibitor were readily apparent from the analysis of individual cells, the transient transfections resulted in significant cell-to-cell heterogeneity. Therefore we sought to establish stable cell lines with 'PCA inside' for use in screening diverse small-molecule, known drug, and natural product libraries.

EXAMPLE 8

Stable, Responsive Cell Lines with PCA Inside

Stable cell lines represent the gold standard for HTS since the assays can be reconstructed at any time from frozen stocks of cells. To demonstrate the construction of a robust stable cell line with PCA inside, HEK293T cells were grown in MEM alpha medium (Invitrogen) supplemented with 10% FBS (Gemini Bio-Products), 1% penicillin, and 1% streptomycin and maintained in a 37° C. incubator at 5% $CO_2$. First, cells were co-transfected with YFP[2]-p65 encoding vectors, and stable cell lines were selected using 100 micrograms/ml of Hygromycin B (Invitrogen). Selected cell lines were then transfected with YFP[1]-p50. Stable cell lines expressing YFP[1]-p50/YFP[2]-p65 were isolated following double antibiotic selection with 50 μg/ml Hygromycin B and 500 μg/ml Zeocin. Cell clones stably expressing the fusion genes were identified by immunoblot analysis and fluorescence microscopy. A single cell line of each transfectant was selected for further characterization. Fluorescence of these lines is stable over at least 25 passages (data not shown). A stable, MEK/ERK cell line—constructed as described below—was used as a control for TNF effects. Fugene 6 (Roche) was used for all the transfections according to manufacturer's directions. Cells stably expressing YFP[1]-p50/YFP[2]-p65 were seeded at 20,000 cells/well in black-walled poly-lysine coated 96 well plate (Greiner). Twenty-four hours later, the cells were incubated with human TNF-alpha (Roche) for 30 min. Nuclei were stained with Hoechst 33342 (Molecular Probes) at 10 micrograms/ml for 10 min. Cells were rinsed with HBSS (Invitrogen) and kept in the same buffer. Fluorescence was visualized and images were acquired using a Discovery-1 automated fluorescence imager (Molecular Devices, Inc.) equipped with excitation and emission filters 470/35 and 535/60, respectively. Where indicated, cells were treated with 25 micromolar ALLN (Calbiochem) for 60 min and induced with TNF in the continued presence of the inhibitor. For the high throughput screening campaign described below, cells were pretreated with compounds (10 micromolar) for 60 minutes and then stimulated with TNFalpha for 30 minutes in the presence of drugs. Cells were then fixed with 2% formaldehyde in HBSS and subsequently stained with Hoechst 33342. All liquid handling was done using a Biomek FX (Beckman) instrument and images were acquired as described above. Images were analyzed using Image J. Translocation is assessed by calculating the nuclear/cytoplasmic ratio of the mean fluorescence intensity for a population of cells (denoted as n) over several images for a given condition.

As shown in FIG. 11, in the stable cell line the p50/p65 complexes were located predominantly in the cytoplasm in the absence of TNF treatment (panel A). TNF treatment resulted in the translocation of p50/p65 complexes into the nucleus (panel B). A stable MEK/ERK PCA cell line was used as a control, with MEK/ERK complexes located in the cytosol (Panel C). In contrast to the results with p53/p65, TNF had no effect on the stable MEK/ERK PCA cell line (Panels D). These results show that, even under conditions where PCA constructs were expressed at relatively low levels, robust fluorescent signals were observed. We also found that these engineered cell lines demonstrate stable fluorescence over at least 20 passages (data not shown).

Previous methods for high-content analyses of NFkB signaling have relied either upon immunocytochemistry, using an anti-p65 antibody, or upon expressing p65 fused to an intact fluorescent protein. FIG. 11 again illustrates an important distinction of PCA, which is that the fragments themselves do not generate a signal. As shown in FIG. 11 (E and F), the stable cell line with the single PCA fusion (p65-YFP[2]) produced no fluorescent signal. With PCA, generation of a signal is dependent upon fragment complementation through the productive interaction of two molecules to which the complementary fragments are fused. Therefore the present invention is clearly distinct from other technologies that involve monitoring individual protein movements within cells.

We further characterized the stable p50/p65 cell line by quantitative image analysis (FIG. 12[A]). The mean fluorescence of the nucleus and cytoplasm of individual cells was quantified, and the N:C fluorescence ratio was calculated. Treatment of the p50/p65 cell line with increasing doses of TNF resulted in an 3-fold increase in the N:C ratio, from 0.47 to 1.42, with a half-maximal response at 10 ng/ml TNF. Analysis of the time course of the TNF response revealed that p50/p65 translocation into the nucleus occurred with a $t_{1/2}$ of 5 min. The maximal response was observed at 15 min., followed by a decrease at 60 min., consistent with feedback recovery of NFkB activation. Across the population of cells, the change in the N:C ratio of p50/p65 was highly statistically significant (p<0.0001). Analysis of 4 independent experiments demonstrated that the PCA response to TNF was consistent (inter-assay CV=5.9; data not shown). This assay functionally re-capitulates with high fidelity the response of the endogenous transcription factors to pathway stimulation, and is a sensitive indicator of the TNF signaling pathway.

To determine if these stable cell lines were suitable for identification of novel inhibitors of TNF/NFkB-dependent pathways, we first tested the effects of the proteasome inhibitor ALLN with the p50/p65 PCA (FIG. 12[b]). ALLN treatment for 4 hr blocked TNF-induced increases in the N:C ratio of p50/p65 complexes by 76%. These results demonstrated that the NFkB complexes visualized by PCA are regulated by TNF signaling through ubiquitin/proteasome mediated events, and further suggested that this would be a sensitive assay for identification of novel therapeutics in an HTS setting.

EXAMPLE 9

High-throughput Screening of a Chemical Library with PCA

To demonstrate the use of PCA in high throughput screening, the Genesis Plus collection of compounds (Microsource Discovery Systems) was assayed in the cells engineered to express the p50/p65 PCA (FIG. 12[C]). Genesis Plus is a collection of 960 diverse compounds, and includes compounds with known toxicity or fluorescent properties. Inclusion of compounds with such properties is important in HTS assay validation, as they might complicate analysis. The final concentration of compounds in wells was 10 micromolar, and all wells contained 0.5% DMSO concentration. Cells were treated with compound (or vehicle) for 90 minutes, and then treated with 25 ng/ml TNF for 30 minutes. Following fixation and staining of nuclei, fluorescence was analyzed on the automated fluorescent microscopy platform (Discovery 1; Universal Imaging/Molecular Devices Corp.).

The average NC ratio was derived by automated image analysis as described above, and compound-treated wells were compared to unstimulated and TNF-stimulated control wells. Results from this focused library screen and the plate-to-plate variability in TNF response is shown in FIG. 12(C). The Z factor, a commonly used metric for assay robustness, is not applicable for this subset of compounds due to the large number of known actives and fluorescent compounds. We utilized the Z' factor, which measures the same statistical parameter across control wells to calculate assay quality. The Z' values averaged 0.627, with a median value of 0.67 across the 12 assay plates. Fluorescent and toxic compounds were readily identified in the automated analysis of NC ratio, demonstrating that compounds with these properties can be identified as false positives in screening campaigns (data not shown). Two compounds in this set known to affect the NFkB pathway, rotenone and 3-methylxanthine, were called as hits in the assay.

In addition to the known inhibitors of this pathway in this compound set, we identified novel NFkB pathway inhibitors. For example, hit confirmation and 8-point dose-response analysis indicates that a compound we denoted as ODC0000160 inhibits the p50/65 PCA assay with an $IC_{50}$ of 1.1 micromolar; relatively potent for a screening hit in a cell-based assay (FIG. 12[D]). This compound has been used in human clinical trials, but has not been linked previously to the NFkB pathway. Clearly, its activity in this assay may have mechanistic significance, a concept supported by the fact that ODC0000160 can elicit apoptosis of human tumor cells (data not shown). The simultaneous exclusion of toxic compounds, enabled by the analysis of cell number and nuclear morphology via Hoechst staining in the standard protocol, provides added confidence to hits obtained in these assays.

EXAMPLE 10

Universality of PCA Strategy

To further demonstrate the ability to use any reporter in conjunction with PCA, we also constructed assays for the TNF pathway based on DHFR PCA (FIG. 13). Coding regions of NFkB subunits p65 and p50 (corresponding to N-terminal 436 amino acids) were PCR amplified from mouse and human cDNAs, respectively, and ligated in-frame downstream of a 15 amino acid flexible linker $(GGGGS)_3$ (SEQ ID No.30) followed by DHFR fragment F[1,2] or F[3] in pCDNA3.1zeo (Invitrogen). IkBa was subcloned separately into pCDNA3.1. For transient expression of these genes, 8×10e4 DHFR-deficient CHO DXB11 cells were seeded into 12 well plates and transfected 24 hours later with [F1,2]-p65, [F3]-p50, and IkBa at the molar ratio of 1:1:1 for each fusion construct using Fugene (Boehringer Mannheim) according to manufacturer's instructions. For controls, where indicated, empty pCDNA3.1 was used in place of IkBa. A total of 1 microgram of DNA was used per well.

Forty-eight hours post-transfection, complexes of F[1,2]-p65 and [F3]-p50 were detected by fluorescence microscopy. Transiently-transfected cells were incubated with 4 microM TxR-MTX (Molecular Probes) for 2 hours at 37C in growth medium (alpha-MEM, 10% FBS). TxR-MTX bound to the DHFR assembled from complementary fragments fused to p65 and p50. Unbound TxR-MTX was washed away by rinsing followed by a 30 minute incubation in fresh medium. For cytokine induction, transiently transfected cells were incubated with 25 ng/ml mTNFalpha (Boehringer Mannheim) during the 30 min wash.

FIG. 13 shows the results of the DHFR PCA. CHO DUKXB11 cells transiently co-expressing DHFR-F(1,2)/p65 with DHFR-F(3)/p50 were co-transfected with I☐B and incubated for 30 minutes with or without mTNFalpha as indicated in the bar graph. Co-transfection of the gene encoding IkBa induced the retention of p65/p50 complexes in the cytosol in the absence of TNF; treatment with TNF induced the translocation of the p65/p50 complex from the cytoplasm into the nucleus. The upper photomicrograph in FIG. 13 shows representative fluorescence images from samples co-expressing IkBa in which the NFkB complexes are located predominantly in the cytoplasm. The lower photomicrograph in FIG. 13 shows representative fluorescence images from samples co-expressing IkBa and induced with TNF, in which the NFkB complexes are located predominantly in the nucleus. We observed marked effects of DNA concentration on sub-cellular localization in transiently transfected cells. NFkB is actively retained in the cytoplasm of unstimulated cells by IkBa. A high level of p50/p65 expression in this experiment perturbed the balance between the transcription factor and its modulator. Excess p50/p65 complexes not bound to IkBa freely translocated to the nucleus of these cells, a phenomenon that could be corrected by co-transfection of IkBa, rendering the assay sensitive to TNF stimulation. In contrast, co-transfection of IkBa was not necessary with the brighter, YFP PCAs described above because the high intensity of the YFP signal allowed the use of very low levels of exogenous expression of the YFP PCA constructs.

To examine the effect of proteasome inhibition on NFkB nuclear translocation, the transiently transfected cells expressing the DHFR PCA were treated with 40 micrograms/ml ALLN (Calbiochem) for 1 hr prior to TxR-MTX labeling and for the subsequent duration of the experiment. The cells were rinsed with PBS and the subcellular location of NFkB complexes were visualized using a Nikon Eclipse TE2000 fluorescence microscope at excitation and emission wavelengths of 580 nm and 625 nm, respectively. Average fluorescence intensities in the nuclei and cytoplasm of cells were quantitated using NIH Image and/or OpenLab (Improvision). FIG. 13(B) shows that the proteasome inhibitor ALLN inhibits the TNF-induced cytoplasmic-to-nuclear translocation of NFkB complexes in the DHFR PCA assay. In the presence of ALLN, the p50/p65 complexes are retained in the cytosol.

The cell-to-cell variability in these transient assays is high, as would be expected, compared with that in a stable cell line. Therefore, although transient assays are useful for interaction mapping and assay validation, stable cell lines are preferred for robust HTS and HCS assays. Stable cell lines can be generated using a variety of methods known to those skilled in the art. With any PCA, stable cell lines can be generated using selectable markers, such as antibiotic resistance markers as described herein or any number of selectable markers that are known to those skilled in the art. With the DHFR PCA, stable cell lines can intrinsically be generated using survival-selection as previously described by Michnick et al. in DHFR-cells; alternatively, MTX selective pressure can be used with cells containing endogenous DHFR, such that only the cells expressing the DHFR PCA are capable of surviving under selective pressure.

These results emphasize a feature of PCA which is the ability to engineer desired properties into fragments in order to improve assay performance. It is an advantage of the present invention that any reporter can be selected for PCA depending on the exact conditions of the assay, the desired detection method, the requisite signal to background, and the biology of the process and target under investigation.

EXAMPLE 11

Assays with Changes in Fluorescence Intensity: IkBa/p65

TNF-induced degradation of IkBa, which is a consequence of ubiquitination and proteasomal degradation, frees bound NFkB and results in translocation of that transcription factor into the nucleus. Thus, disassembly of the IkBa-NFkB complex is a key step in NFkB-mediated gene regulation. To visualize regulation of the NFkB pathway at this level, we engineered a stable cell line expressing an IkBa/p65 PCA (FIG. 14). ERK1/MEK1 was used as a control. ERK1 was ligated to the 5' end of YFP[1] while IkBa and MEK1 were appended to YFP[2] in N-terminal fusions. The fusion genes were subcloned into pCDNA3.1 expression vectors (Invitrogen) with Zeocin selectable marker for YFP[1]-p50, IkBa-YFP[1] and ERK1-YFP[1] and hygromycin marker for YFP[2]-p65 and ERK1-YFP[2]. A linker consisting of $(GGGGS)_2$ (SEQ ID No.1) separated the genes of interest and the YFP fragments.

Cells expressing IkBa-YFP[1]/YFP[2]-p65 or the controls, MEK-YFP[2]/ERK1-YFP[1], were seeded at 20,000 cells/well in black-walled poly-lysine coated 96 well plate (Greiner). Twenty-four hours later, the cells were incubated with human TNF (Roche) for 30 min. Nuclei were stained with Hoechst 33342 (Molecular Probes) at 33 micrograms/ml for 10 min. Cells were rinsed with HBSS (Invitrogen) and kept in the same buffer. Fluorescence was visualized and images were acquired using a Discovery-1 automated fluorescence imager (Molecular Devices, Inc.) equipped with excitation and emission filters 470/35 and 535/60, respectively. The proteasome inhibitor ALLN was tested with the IkBa/p65 PCA. Cells were treated with 25 micromolar ALLN (Calbiochem) for 60 min and induced with TNF in the continued presence of the inhibitor.

Images were analyzed using Image J. Total mean fluorescence intensity for all cells was assessed by adding weighted mean fluorescence intensities for the nucleus and cytoplasm for individual cells in the population for a given condition +/– standard error. Fluorescent imaging revealed that IkBa/p65 complexes were located predominantly in the cytoplasm and treatment of the cells with TNF resulted in a significant decrease in fluorescence (FIG. 14), consistent with cytokine-induced proteolysis of IkBa and disassembly of IkBa/p65 PCA complexes. ALLN treatment for 4 hr inhibited the TNF-induced reduction of IkBa/p65 complexes by 98%, an effect that was apparent in the microscopic images. Quantitative image analysis showed a TNFalpha dose-dependent decrease in mean fluorescence intensities of IkBa/p65 complexes cells but not of the control (MEK/ERK) complexes. This suggests that TNF specifically induced the disassembly of IkBa/p65 complexes. The maximal response was observed at a TNF concentration of 10 ng/ml, where the mean cell fluorescence intensity of IkBa/p65 complexes was approximately 40% that of the unstimulated cells. Studies of the time course of the TNF response showed a $t_{1/2}$ of 4 minutes, with a maximal response at 20 minutes. There was no effect of TNF treatment on the fluorescence intensity of the control (MEK/ERK) PCA. These results demonstrate that PCA is well suited to assessing dynamic regulation of signaling complexes in living cells.

EXAMPLE 12

Assays for Ubiquitination of Proteins and their Utility in Identifying Proteasome Inhibitors The selective degradation of many proteins starts with the ubiquitin system, a series of steps by which proteins are targeted for degradation by covalent ligation to ubiquitin. Ubiquitin is a highly conserved 76-amino acid polypeptide. Since its discovery in the mid-1970s, ubiquitin has been associated with cellular house-keeping functions such as eliminating damaged proteins. It has recently become clear that ubiquitin is involved in a variety of other vital processes at different subcellular locations ranging from the plasma membrane to the nucleus, including cell-cycle progression, signal transduction, transcriptional regulation, receptor down-regulation, and endocytosis.

Ubiquitin is covalently attached to proteins through an isopeptide bond between its carboxy-terminal glycine and the epsilon-amino group of lysines in the target protein. This attachment is catalyzed by enzymes that activate and ultimately conjugate the ubiquitin moiety to a lysine residue in the substrate. This can be followed by further additions of ubiquitin to specific lysine residues within the linked ubiquitin itself, resulting in a poly-ubiquitin chain. This covalent modification can be reversed by unique proteases specific for the iso-peptide linkage. Although ubiquitin is the best-characterized polypeptide modifier, other polypeptides (often referred to as Ubiquitin-like, or Ubl) are also conjugated to targets in analogous reactions. These 'alternative' modifiers, which differ from ubiquitin in sequence similarity but which are structurally similar to ubiquitin, include SUMO; Nedd8; Hub1, ISG15 or UCRP; and Apg 12.

Ubiquitinated proteins are recognized by the 19S regulatory subunit of the proteasome, which removes the ubiquitin chain for recycling and denatures the doomed protein. The denatured protein is then fed into the core of the proteasome and reduced to short peptides (less than 22 residues). A number of proteins that are ubiquitinated have already been identified. These include cyclins and related proteins (cyclins A, B, D, E and cyclin-dependent kinase inhibitors); tumor suppressors, including p53; oncogenes, including c-fos, c-jun, c-myc and N-myc; inhibitory proteins, including IkappaBalpha and p130; and enzymes, including cdc25 phosphatase, tyrosine aminotransferase, and topoisomerases (I and IIalpha). Copies of two protein motifs—the F-box and the Ring finger, which are believed to identify targets for protein turnover—number in the hundreds in the eukaryotic genome suggesting a large number of proteins whose turnover is regulated by the ubiquitin system.

In addition to the proteasome machinery itself, the regulatory events upstream of the proteasome (that is, phosphorylation and ubiquitination of proteasome substrates and their regulators) are being actively explored for drug discovery. The selectivity of protein degradation is determined mainly at the stage of ligation to ubiquitin. Briefly, ubiquitin-protein ligation requires the sequential action of three enzymes. Ubiquitin must first become attached to a member of the family of E2 ubiquitin-conjugating enzymes (an E1 ubiquitin-activating enzyme provides the initial ATP-dependent activation). Subsequently, the E2 enzyme itself, or, more typically, an E3 ligase, provides the specificity for the transfer of ubiquitin onto the targeted protein (ligase substrate). Usually there is a single E1, but there are many species of E2s and multiple families of E3s or E3 multiprotein complexes. Specific E3s appear to be responsible mainly for the selectivity of ubiquitin-protein ligation (and thus, of protein degradation). They do so by binding specific protein substrates that contain specific recognition signals. In some cases, binding of the substrate protein to an E3 is indirect, via an adaptor protein. The identification of the E3 ubiquitin ligases as proteins containing protein-protein interaction domains that couple to the ubiquitin-charged E2 (ubiquitin-conjugating) enzyme provided the link between substrate recognition and the catalytic steps for ubiquitin chain formation.

Signal-induced activation of NF-κB involves phosphorylation-dependent ubiquitination of IkBa (IkappaBalpha), which targets the protein for rapid degradation by the proteasome and releases NFκB for translocation to the nucleus. TNF-induced ubiquitination of IkBa is essential for its proteolysis and subsequent activation of NFkB. Therefore, we sought to demonstrate the utility of PCA in identifying ubiquitinated proteins and inhibitors of the proteasome.

IkBa-YFP[1] and YFP[2]-ubiquitin were constructed as described above and transiently expressed in HEK293T cells. FIG. 15 shows that mean fluorescence intensity was significantly increased in TNF induced cells treated with the proteasome inhibitor ALLN compared with control, vehicle treated cells. These results show that PCA captures the dynamic, signal induced conjugation of ubiquitin to substrate proteins and demonstrates its application in identification of inhibitors of the ubiquitin-proteasome pathway. The present invention can be applied to the large-scale identification of proteins modified by ubiquitin and ubiquitin-like polypeptides; for example, using library screening as in Example 2 of the present invention where the 'bait' is ubiquitin or a ubiquitin-like molecule, or by using interaction mapping as in Example 4 where ubiquitin or a ubiquitin-like molecule is tested against individual cDNAs to identify ubiquitin-protein complexes. In addition, by constructing ubiquitin PCAs for specific protein targets, the assays that are the subject of the present invention can immediately be applied to high-throughput screening for novel therapeutic agents.

EXAMPLE 13

Vectors and Vector Elements

It will be apparent to one skilled in the art that a large number of different vectors can be used in conjunction with the present invention. The elements of useful vectors can be varied as needed depending on the cell of interest, desired promoter, reporter choice, linker length, and cloning sites. The present invention is not limited to the vector sequence, its elements, or the way in which the genes are expressed. Plasmid, retroviral and adenoviral vectors are all compatible with the present invention. Several examples highlighting vector design and features specific to PCA are given below. These examples are not intended to be limiting for the applications of the present invention.

Choice of linker length. The use of a flexible linker between genes of interest and complementary fragments facilitates PCA. Linker lengths ranging from 5 amino acids to 30 amino acids have been used for PCA. The linker length can be varied as desired in order to control the intermolecular distance between interacting molecules required for complementation. For example, Remy and Michnick showed that shortening the length of the flexible linker between the gene of interest and the PCA fragment allowed the precise detection of allosteric changes in erythropoietin receptor subunits upon ligand binding (see References). Assisted complementation—for example, between proteins that are indirectly associating as a result of their mutual binding to a third molecule or that are constitutively associated at a greater intermolecular distance—can also be investigated in detail by using longer linkers.

For many applications, a semi-standard linker of 10 to 15 amino acids—for example, as repeats of the 5-amino acid (GGGGS) (SEQ ID No.31) sequence used herein—facilitates fragment complementation and—as we have demonstrated in the present invention—is suitable for many applications of PCA. As a consequence, standard vectors can be constructed in which a fixed linker length is used and into which genes can be rapidly subcloned for assay construction as in FIG. 1 and FIG. 16.

Choice and design of selectable marker. A wide variety of choices of selectable markers is presented here, and their application to the present invention will be readily understood by one skilled in the art.

In the case of PCAs based on survival-selection assays—for example, using fragments of enzymes that act as drug resistance markers themselves, such as aminoglycoside kinase (AK PCA) or hygromycin phosphotransferase (HPT PCA), or where the PCA complements a metabolic pathway, such as DHFR PCA—no additional drug resistance genes need be incorporated in the expression plasmids. In those cases, reconstitution of the selectable marker upon fragment complementation allows cell survival under selective pressure.

If the PCA is based on a protein that produces an optically detectable signal, an additional drug resistance or survival gene can be expressed to enable selection of cells expressing the proteins of interest. For example, in the vectors shown in FIG. 16 and used in the construction of stable cell lines in the present invention (FIG. 11 and FIG. 14), different antibiotic resistance markers (hygromycin and zeocin) were used on the YFP[1] and YFP[2] plasmids to facilitate the generation of stable cell lines expressing the YFP PCA. The fluorescent or luminescent signal of the PCA can itself be used to select the stably expressing cells, for example by using FACS or bead-based selection methods to sort cells that have positive signals. FACS or similar methods can also be used in conjunction with antibodies to cell-surface PCAs, e.g. where the PCA reconstitutes a non-native cell surface marker that can be detected with a fluorescently tagged antibody.

As an alternative to antibiotic resistance genes or metabolic survival genes such as DHFR, antigens or antibodies can also be used as selectable markers or detection probes in conjunction with PCA. For example, antigens can be fragmented for PCA, such that the fragments reconstitute a protein that can be detected by a fluorescently-tagged antibody. If the reconstituted antigen represents a foreign protein in the transfected cells, there will be no background activity in the absence of a protein-protein interaction that reconstitutes the antigen. Alternatively, antigens (or antibodies) can be included as separate, non-operably-linked elements within vectors containing gene-fragment fusions. In that case the co-expression of the gene-fragment fusions of interest can be detected by antibody-based cell selection using an antibody specific for the antigen element. Selection can be achieved by single-color or multi-color FACS sorting of antigen-expressing cells or by binding of antibodies linked to beads or a solid support.

EXAMPLE 14

Dual PCAs Combining a Fluorescent or Luminescent PCA with a Survival-selection PCA, Enabling the Rapid Selection of Cell Lines for HTS and HCS Although PCAs can be assembled on separate plasmids, as in the present invention, one or more polycistronic vectors can also be used in conjunction with PCA as shown in FIG. 17. With this example we provide "dual PCAs" in which the construction of an HTS or HCS assay is linked to the generation of a stable cell line. Complementary bicistronic vectors are used to generate a stable cell line, such as with a leucine zipper-directed DHFR PCA, wherein the cell line also contains a fluorescent or luminescent PCA, where the fluorescent or luminescent signal is driven by the interaction of two proteins of interest.

Bicistronic vectors contain an IRES (internal ribosomal entry sequence) that provides the ability to link the expression of one polypeptide to that of another, such as a selectable marker. The creation of bicistronic vectors has made it possible to express a gene encoding a single polypeptide and the DHFR gene as a single mRNA, which is then translated into the two separate proteins (Davies M V, Kaufman R J. 1992. The sequence context of the initiation codon in the encephalomyocarditis virus leader modulates efficiency of internal translation initiation. J Virol 66:1924–1932.) Expression of the DHFR gene and the recombinant gene as a single mRNA enriches for methotrexate amplification of both genes, and greatly enhances production of the molecule of interest.

As shown in FIG. 17, we have combined two bicistronic vectors to create a dual PCA which allows construction of an HTS or HCS assay with rapid, intrinsic selection of stable cell lines. Two complementary bicistronic vectors are constructed, each with one half of a fluorescent or luminescent PCA and with one half of a survival-selection PCA. In the example shown, we combined a fluorescent or luminescent PCA based on the present invention with the previously-described DHFR PCA, which enables rapid selection of stable cell lines through leucine zipper-directed reassembly of active DHFR (Pelletier, J. N., C.-Valois, F.-X. and Michnick, S. W., 1998, Oligomerization domain-directed reassembly of active dihydrofolate reductase from rationally-designed fragments *Proc Natl Acad Sci USA*, 95: 12141–12146; Remy, I. and Michnick, S. W., 2001, Visualization of Biochemical Networks in Living Cells, *Proc Natl Acad Sci USA*, 98: 7678–7683). The expression of each half of an HTS- or HCS-compatible PCA is linked to the expression of one half of a survival-selection PCA such that, if cells survive under selective pressure, the resulting cell line will be positive for the PCA pair comprising the HTS or HCS assay.

As depicted in FIG. 17, a promoter drives the expression of the first PCA pair, comprising the genes of interest operably linked to the respective F1 and F2 fragments of an optically detectable reporter; while the IRES of each of the two vectors encodes the two halves of the second PCA, the latter comprising two oligomerization domains (such as the constitutively dimerizing GCN4 leucine zippers used in Example 2 of the present invention) operably linked to the respective F1 and F2 fragments of a selectable marker (such as the fragments of DHFR used in Example 9 of the present invention). The two bicistronic vectors are co-transfected into cells and subjected to selective pressure as previously described for the DHFR PCA such that co-expression of the second PCA pair enables the selection of cells that also co-express the first PCA pair. Cells are grown under conditions, described by us previously, in which the cells only survive if both fragments are expressed and DHFR is reconstituted though leucine zipper-directed complementation. Thus, stable cell lines can automatically be generated with PCA inside for use in HTS or HCS. The dual PCA provides an efficient means for generating a stable cell line without the need for antibiotic selection, and will speed the establishment of stable cell lines for a large number of screening applications.

Choice of promoter. A constitutive promoter may be used in the present invention, such as the CMV promoter used in several examples provided herein. However, alternative vector and promoter schemes are suitable for use with the present invention and will be described here with particular reference to the use of pathway-specific and/or cell-specific promoters.

Individual complementary fragment-fusion pairs can be put under the control of inducible promoters. In such a system the two complementary fragment fusions can be turned on and expression levels controlled by dose dependent expression with the inducer. Commercially-available inducible promoters (e.g. the Tet or Ecdysone-responsive elements) can be used.

The present invention also provides for the novel use of cis-acting elements in conjunction with PCA. Combining inducible promoters with PCA provides a system in which the PCA response is enhanced or attenuated by the effect of a drug on a signaling pathway. In this embodiment of the present invention, full-length human genes operably linked to PCA fragment coding sequences are cloned into eukaryotic expression vectors. The fusion protein expression is controlled by the transcription regulatory elements of the human gene encoded by the fusion, or by another cis-acting regulatory element. These assays simultaneously capture protein activity (via the PCA component) and protein concentrations regulated at the transcriptional level (the transcriptional control element).

Details of this aspect of the present invention are as follows. Many signaling events (and the constituent drug targets) are controlled at multiple steps, including transcriptional control of the protein coding message, translational control, protein activity (including phosphorylation, dephosphorylation, acetylation, and allosteric regulation) and protein stability and half-life. Expressing PCAs under the control of regulated promoters combines the predictive, pathway-mapping capabilities of PCA assays and the ability to quantify gene regulation characterized by more traditional transcription reporter gene assays. The simultaneous capture of both types of information facilitates a comprehensive, real-time assessment of cellular activity.

Examples of transcriptional regulatory elements include cell cycle-regulated proteins such as cyclin D1 and other cyclins, kinases and phosphatases regulated during cell cycle progression such as polo-like kinases (PLKs). Transcription factors such as c-Fos, c-Myc, EGR-1, c-Jun, JunB, ATF-2, CREB, etc. are regulated in part at the transcriptional level. Other examples include cytokine and growth factor-induced proteins (such as matrix metalloproteinases, EGF and TGF-beta and their receptors), stress- or toxicity-induced proteins (e.g. heat shock proteins, ATF-3), and acute phase proteins (e.g. beta2-macroglobulin and transferrin). In each case the full-length promoter and enhancer sequence from the gene may be used to direct the expression of the PCA fusion protein. Promoter and enhancer cis-acting elements have been shown to be composed of multiple sequential and overlapping binding sites for the trans-acting transcription factors. The activity of these sites in directing the transcription of their cognate mRNA is generally considered to be independent of binding site orientation and distance from the start site of transcription. A large body of work has demonstrated that these cis-acting elements can be dissected such that individual transcription factor-binding sites are identified. Further, these sites can be engineered into gene expression vectors such that the activity of the expressed gene is dependent on the amount and activity of transcription factors bound to the isolated site. Finally, these individual transcription factor binding sites can be multimerized to increase the transcriptional induction of the expressed gene in response to specific stimuli. Examples of the engineering of single and multimerized transcriptional response elements to optimize the response to specific stimuli or pathway activation are provided in (Westwick et al., 1997, and references therein). Partial or full-length promoter enhancer sequences, or discrete cis-acting elements may be utilized, either singly or multimerized, to direct the expression of PCA fusions.

An example of the use of inducible promoters for the TNF pathway is as follows. The IkBa gene is fused in-frame to a PCA reporter fragment-coding sequence. The IkBa fusion protein is expressed under the control of an IkBa promoter, which is controlled primarily by NFkB-dependent signals. This construct (or a cognate engineered cell line) is co-transfected with a vector encoding a binding partner of IkBa, such as the transcription factor p65. Cell stimulation resulting in NFkB pathway activation will result in an increase in IkBa-PCA fusion protein expression due to transcriptional induction of the fusion. In addition, post-translational regulation of both the IkBa and p65 PCA fusions can be assessed by the intensity and sub-cellular localization of the PCA signal. As shown in FIGS. 11–14, NFkB pathway activation eventually leads to degradation of IkBa (FIG. 14) and nuclear translocation of the p65 component of this complex (FIGS. 11–13). The interplay of transcriptional and post-transcriptional regulation of this pathway has previously been shown to result in cycles of IkBa protein levels (and activity) in the cell. Therefore, inducible promoter-PCA assays can be used to assess the complex biology of the TNF pathway and similar complex biological systems.

Alternatively, gene-fragment fusions under the control of any inducible promoter(s) can be constructed, wherein the interacting pair of the PCA assay generates a constitutive activity (e.g. fluorescence or luminescence) when expressed. PCA will only occur if both promoters are active. This will constitute a sensitive, live cell, real-time assay for transcriptional activity of one or two gene-regulating cis-acting elements. By fusing each PCA elements to a different promoter, an assay will yield a positive signal only in the instance that both promoters are active in the cell of interest.

"Universal" vectors. Once an expression vector, linker length, reporter fragments and promoter have been selected, vectors can be constructed for speed and ease in subcloning genes or libraries of interest for PCA. Briefly, for any given reporter, four universal vectors can be generated, encoding the reporter fragment of interest (shown as F1 and F2) fused in-frame to a flexible linker comprised of glycine and serine residues. A gene of interest is then fused to the reporter fragments, for example via a unique restriction site in the linker, either at the 5'- or 3'-end of the gene, to generate four possible fusion proteins, as shown in FIG. 1a and FIG. 16. Alternatively, homologous recombination sites can be used in conjunction with recombination-based cloning methods. Construction of vectors suitable for the present invention can be accomplished with any suitable recombination method, for example, the Gateway system sold by Invitrogen Corp. and alternative rapid cloning systems are compatible with the present invention.

REFERENCES

The entire contents including the cited references of the following patents and publications are incorporated by reference.

| | |
|---|---|
| 6,270,964 | Michnick, et al. |
| 6,294,330 | Michnick, et al. |
| 6,428,951 | Michnick, et al. |
| 5,989,835 | Dunlay, et al. |
| 6,518,021 | Thastrup, et al. |
| 5,583,217 | Quante, et al. |
| 5,516,902 | Quante, et al. |
| 5,514,561 | Quante, et al. |
| 5,338,843 | Quante, et al. |

Publications

Pelletier, J. N., Remy, I. and Michnick, S. W. (1998). Protein-Fragment Complementation Assays: a General Strategy for the in vivo Detection of Protein-Protein Interactions. *Journal of Biomolecular Techniques*, 10: 32–39.

Remy, I. and Michnick, S. W. (1999). Clonal Selection and In Vivo Quantitation of Protein Interactions with Protein Fragment Complementation Assays. *Proc Natl Acad Sci USA*, 96: 5394–5399.

Remy, I., Pelletier, J. N., Galarneau, A. and Michnick, S. W. (2002). Protein Interactions and Library Screening with Protein Fragment Complementation Strategies. *Protein-protein interactions: A molecular cloning manual*. E. A. Golemis, editor. Cold Spring Harbor Laboratory Press. Chapter 25, 449–475.

Remy, I., Wilson, I. A. and Michnick, S. W. (1999). Erythropoietin receptor activation by a ligand-induced conformation change. *Science*, 283: 990–993.

Galarneau, A., Primeau, M., Trudeau, L.-E. and Michnick, S. W. (2002). A Protein fragment Complementation Assay based on TEM1 β-lactamase for detection of protein-protein interactions. *Nat Biotechnol*, 20: 619–622.

Michnick, S. W., Remy, I., C.-Valois, F. X., Vallee-Belisle, A., Galarneau, A. and Pelletier, J. N. (2000) Detection of Protein-Protein Interactions by Protein Fragment Complementation Strategies, Parts A and B (John N. Abelson, Scott D Emr and Jeremy Thorner, editors) A Volume of *Methods in Enzymology*. 328, 208–230.

Remy, I. and Michnick, S. W. (2001). Visualization of Biochemical Networks in Living Cells. *Proc Natl Acad Sci USA*, 98: 7678–7683.

Schmid, J. A., et al. (2000) Dynamics of NFkappaB and IkappaBalpha studied with green fluorescent protein (GFP) fusion proteins. J. Biol. Chem. 275 (22): 17035–17042.

While the many forms of the invention herein disclosed constitute presently preferred embodiments, many others are possible and further details of the preferred embodiments and other possible embodiments are not to be construed as limitations. It is understood that the terms used herein are merely descriptive rather than limiting and that various changes and many equivalents may be made without departing from the spirit or scope of the claimed invention.

What is claimed is:

1. A method for drug discovery, said method comprising: (A) constructing one or more protein-fragment complementation assays (PCAs') wherein the molecules fused to the protein reporter fragments used in said PCAs' are identified by a method chosen from the group consisting of: (i) cDNA library screening; (ii) interaction mapping; and (iii) prior knowledge of the existence of an interaction between a pair of proteins; (B) testing the effects of chemical compounds on the activity of said assay(s); (C) using the results of said assay(s) to identify chemical compounds with desired activities with the proviso that said protein complementation assays do not utilize ubiquitin fragments and said assays are not two hybrid assays.

2. Protein fragment complementation assays for drug discovery comprising a reassembly of separate fragments of a protein reporter molecule wherein said protein reporter fragments are fused to molecules selected from the group consisting of a receptor, a tumor suppressor gene, a kinase, a kinase substrate, an oncogene, an adaptor protein, a ubiquitin-like molecule, and a transcription factor; wherein reassembly of the protein reporter fragments generates an optically detectable signal with the proviso that said protein fragments are not ubiquitin fragments and said assay is not a two hybrid assay.

3. An assay composition for drug discovery comprising complementary fragments of a first protein reporter molecule, said protein complementary fragments exhibiting a detectable activity when associated, wherein each fragment is fused to a separate molecule selected from the group consisting of a receptor, a tumor suppressor gene, a kinase, a kinase substrate, an oncogene, an adaptor protein, a ubiquitin-like molecule, and a transcription factor; with the proviso that said protein fragments are not ubiquitin fragments and said assay is not a two hybrid assay.

4. An assay composition for drug discovery comprising a product selected from the group consisting of: (a) a first fusion product comprising: 1) a first protein fragment of a first protein reporter molecule whose fragments exhibit a detectable activity when associated and 2) a second molecule that is fused to said first protein fragment; (b) a second fusion product comprising 1) a second protein fragment of said first protein reporter molecule and 2) a third molecule that is fused to said second protein fragment; and (c) a third fusion product comprising: 1) a first protein fragment of a second protein reporter molecule whose fragments exhibit a detectable activity when associated and 2) a fourth molecule that is fused to said first protein fragment; (d) a fourth fusion product comprising 1) a second protein fragment of said second protein reporter molecule and 2) a fifth molecule that is fused to said second protein fragment; and e) a combination of (a), (b), (c) and (d) with the proviso that said protein fragments are not ubiquitin fragments and wherein said fusion products (a) and (b) are not two hybrid constructs.

5. An assay composition for drug discovery comprising a nucleic acid molecule coding for a protein reporter fragment fusion product, which molecule comprises sequences coding for a product selected from the group consisting of: (a) a first protein reporter fusion product comprising: 1) a fragment of a first protein reporter molecule whose fragments can exhibit a detectable activity when associated and 2) a second molecule fused to the protein fragment of the first protein reporter molecule; (b) a second fusion product comprising 1) a fragment of a second protein reporter molecule whose fragments can exhibit a detectable activity when associated and 2) a third molecule fused to the protein fragment of the second protein reporter molecule; and (c) both (a) and (b) with the proviso that said protein fragments are not ubiquitin fragments and wherein said fusion products (a) and (b) are not two hybrid constructs.

6. A method for drug discovery, said method comprising: (A) constructing one or more protein-fragment complementation assays (PCAs') wherein the molecules fused to the protein reporter fragments used in said PCAs' are selected from the group consisting of a receptor, a tumor suppressor gene, a kinase, a kinase substrate, an oncogene, an adaptor protein, a ubiquitin-like molecule, and a transcription factor; (B) testing the effects of chemical compounds on the activity of said assay(s); (C) using the results of said assay(s) to identify chemical compounds with desired activities with the proviso that said protein complementation assays do not utilize ubiquitin fragments and said assays are not two hybrid assays.

7. A method for drug discovery, said method comprising: (A) constructing one or more protein-fragment complementation assays (PCAs') wherein the molecules fused to the protein reporter fragments used in said PCAs' are selected from the group consisting of p53, Chk1, ATR, ATM, Rad 51, PDK2, STAT1, FKBP, FRAP, p70S6Kinase, S6 protein, 4E-BP1, PPP2A, TNFR, TRADD, FADD, p65 subunit of NFkappaB, p50 subunit of NFkappaB, CBP, TRAF2, Ubiquitin, IKK-beta, IKK-gamma, IkappaBalpha, MEK, ERK, PI-3-Kinase, PKB, Ft1, GCN4, PDK1, GSK3, NF-AT, and Calcineurin; and domains, fragments or homologues thereof, (B) testing the effects of chemical compounds on the activity of said assay(s); (C) using the results of said assay(s) to identify chemical compounds with desired activities with the proviso that said protein complementation assays do not utilize ubiquitin fragments and said assays are not two hybrid assays.

8. Protein fragment complementation assays for drug discovery comprising a reassembly of separate fragments of a protein reporter molecule wherein said protein reporter fragments are fused to molecules selected from the group consisting of p53, Chk1, ATR, ATM, Rad 51, PDK2, STAT1, FKBP, FRAP, p70S6Kinase, S6 protein, 4E-BP1, PPP2A, TNFR, TRADD, FADD, p65 subunit of NFkappaB, p50 subunit of NFkappaB, CBP, TRAF2, Ubiquitin, IKK-beta, IKK-gamma, IkappaBalpha, MEK, ERK, PI-3-Kinase, PKB, Ft1, GCN4, PDK1, GSK3, NF-AT, and Calcineurin; and domains, fragments or homologues thereof; wherein reassembly of the protein reporter fragments generates an optically detectable signal with the proviso that said protein fragments are not ubiquitin fragments and said assay is not a two hybrid assay.

9. An assay composition for drug discovery comprising complementary fragments of a first protein reporter molecule, said protein complementary fragments exhibiting a detectable activity when associated, wherein each fragment is fused to a separate molecule selected from the group consisting of p53, Chk1, ATR, ATM, Rad 51, PDK2, STAT1, FKBP, FRAP, p70S6Kinase, S6 protein, 4E-BP1, PPP2A, TNFR, TRADD, FADD, p65 subunit of NFkappaB, p50 subunit of NFkappaB, CBP, TRAF2, Ubiquitin, IKK-beta, IKK-gamma, IkappaBalpha, MEK, ERK, PI-3-Kinase, PKB, Ft1, GCN4, PDK1, GSK3, NF-AT, and Calcineurin; and domains, fragments or homologues thereof; with the proviso that said protein fragments are not ubiquitin fragments and said assay is not a two hybrid assay.

10. A method for drug discovery, said method comprising: (A) constructing one or more protein-fragment complementation assays (PCAs'); (B) testing the effects of chemical compounds on the activity of said assay(s); (C) using the results of said assay(s) to identify chemical compounds with desired activities with the proviso that said protein complementation assays do not utilize ubiquitin fragments and said assays are not two hybrid assays and wherein said method is used to screen for a receptor agonist, a receptor antagonist, a kinase inhibitor, a phosphatase inhibitor, a cell cycle inhibitor, a heat shock protein inhibitor, an E3 ligase inhibitor, a transcription factor inhibitor, an inhibitor of a protein-protein interaction, or a proteasome inhibitor.

11. Protein fragment complementation assays for drug discovery comprising a reassembly of separate fragments of a protein reporter molecule, wherein reassembly of the protein reporter fragments generates an optically detectable signal with the proviso that said protein fragments are not ubiquitin fragments and said assay is not a two hybrid assay and wherein said assays are used to screen for a receptor agonist, a receptor antagonist, a kinase inhibitor, a phosphatase inhibitor, a cell cycle inhibitor, a heat shock protein inhibitor, an E3 ligase inhibitor, a transcription factor inhibitor, an inhibitor of a protein-protein interaction, or a proteasome inhibitor.

12. An assay composition for drug discovery comprising complementary fragments of a first protein reporter molecule, said protein complementary fragments exhibiting a detectable activity when associated, wherein each fragment is fused to a separate molecule; with the proviso that said protein fragments are not ubiquitin fragments and said assay is not a two hybrid assay and wherein said assay composition is used to screen for a receptor agonist, a receptor antagonist, a kinase inhibitor, a phosphatase inhibitor, a cell cycle inhibitor, a heat shock protein inhibitor, an E3 ligase inhibitor, a transcription factor inhibitor, an inhibitor of a protein-protein interaction, or a proteasome inhibitor.

* * * * *

SEQUENCE LISTING

<160> NUMBER OF SEQ ID NOS: 31

<210> SEQ ID NO 1
<211> LENGTH: 10
<212> TYPE: PRT
<213> ORGANISM: Artificial
<220> FEATURE:
<223> OTHER INFORMATION: synthetic construct, a flexible linker

<400> SEQUENCE: 1

Gly Gly Gly Gly Ser Gly Gly Gly Gly Ser
1               5                   10

<210> SEQ ID NO 2
<211> LENGTH: 483
<212> TYPE: DNA
<213> ORGANISM: Artificial
<220> FEATURE:
<223> OTHER INFORMATION: synthetic construct; RLuc(F1) with stop codon
      added at end
<220> FEATURE:
<221> NAME/KEY: CDS
<222> LOCATION: (1)..(483)
<223> OTHER INFORMATION: RLuc(F1) corresponds to a.a. residues 1-160 of
      wild-type R. Luciferase

<400> SEQUENCE: 2

| atg gct tcc aag gtg tac gac ccc gag caa cgc aaa cgc atg atc act | 48 |
| Met Ala Ser Lys Val Tyr Asp Pro Glu Gln Arg Lys Arg Met Ile Thr | |
| 1               5                   10                  15      | |

| ggg cct cag tgg tgg gct cgc tgc aag caa atg aac gtg ctg gac tcc | 96 |
| Gly Pro Gln Trp Trp Ala Arg Cys Lys Gln Met Asn Val Leu Asp Ser | |
|         20                  25                  30              | |

| ttc atc aac tac tat gat tcc gag aag cac gcc gag aac gcc gtg att | 144 |
| Phe Ile Asn Tyr Tyr Asp Ser Glu Lys His Ala Glu Asn Ala Val Ile | |
|     35                  40                  45                  | |

| ttt ctg cat ggt aac gct gcc tcc agc tac ctg tgg agg cac gtc gtg | 192 |
| Phe Leu His Gly Asn Ala Ala Ser Ser Tyr Leu Trp Arg His Val Val | |
| 50                  55                  60                      | |

| cct cac atc gag ccc gtg gct aga tgc atc atc cct gat ctg atc gga | 240 |
| Pro His Ile Glu Pro Val Ala Arg Cys Ile Ile Pro Asp Leu Ile Gly | |
| 65                  70                  75                  80  | |

| atg ggt aag tcc ggc aag agc ggg aat ggc tca tat cgc ctc ctg gat | 288 |
| Met Gly Lys Ser Gly Lys Ser Gly Asn Gly Ser Tyr Arg Leu Leu Asp | |
|                 85                  90                  95      | |

| cac tac aag tac ctc acc gct tgg ttc gag ctg ctg aac ctt cca aag | 336 |
| His Tyr Lys Tyr Leu Thr Ala Trp Phe Glu Leu Leu Asn Leu Pro Lys | |
|             100                 105                 110         | |

| aaa atc atc ttt gtg ggc cac gac tgg ggg gct tgt ctg gcc ttt cac | 384 |
| Lys Ile Ile Phe Val Gly His Asp Trp Gly Ala Cys Leu Ala Phe His | |
|         115                 120                 125             | |

| tac tcc tac gag cac caa gac aag atc aag gcc atc gtc cat gct gag | 432 |
| Tyr Ser Tyr Glu His Gln Asp Lys Ile Lys Ala Ile Val His Ala Glu | |
|     130                 135                 140                 | |

| agt gtc gtg gac gtg atc gag tcc tgg gac gag tgg cct gac atc gag | 480 |
| Ser Val Val Asp Val Ile Glu Ser Trp Asp Glu Trp Pro Asp Ile Glu | |
| 145                 150                 155                 160 | |

| taa | 483 |

<210> SEQ ID NO 3
<211> LENGTH: 160

<212> TYPE: PRT
<213> ORGANISM: Artificial
<220> FEATURE:
<223> OTHER INFORMATION: Synthetic Construct

<400> SEQUENCE: 3

```
Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160
```

<210> SEQ ID NO 4
<211> LENGTH: 480
<212> TYPE: DNA
<213> ORGANISM: Artificial
<220> FEATURE:
<223> OTHER INFORMATION: synthetic construct; RLuc(F1) with stop codon
    added at end and
    initial "atg" (or Met) removed
<220> FEATURE:
<221> NAME/KEY: CDS
<222> LOCATION: (1)..(480)
<223> OTHER INFORMATION: RLuc(F1) corresponds to a.a. residues 1-160 of
    wild-type R.
    Luciferase

<400> SEQUENCE: 4

```
gct tcc aag gtg tac gac ccc gag caa cgc aaa cgc atg atc act ggg      48
Ala Ser Lys Val Tyr Asp Pro Glu Gln Arg Lys Arg Met Ile Thr Gly
1               5                   10                  15 cct cag tgg tgg gct cgc tgc aag caa atg aac gtg ctg gac tcc ttc      96
Pro Gln Trp Trp Ala Arg Cys Lys Gln Met Asn Val Leu Asp Ser Phe
            20                  25                  30 atc aac tac tat gat tcc gag aag cac gcc gag aac gcc gtg att ttt     144
Ile Asn Tyr Tyr Asp Ser Glu Lys His Ala Glu Asn Ala Val Ile Phe
        35                  40                  45 ctg cat ggt aac gct gcc tcc agc tac ctg tgg agg cac gtc gtg cct     192
Leu His Gly Asn Ala Ala Ser Ser Tyr Leu Trp Arg His Val Val Pro
    50                  55                  60 cac atc gag ccc gtg gct aga tgc atc atc cct gat ctg atc gga atg     240
His Ile Glu Pro Val Ala Arg Cys Ile Ile Pro Asp Leu Ile Gly Met
65                  70                  75                  80 ggt aag tcc ggc aag agc ggg aat ggc tca tat cgc ctc ctg gat cac     288
Gly Lys Ser Gly Lys Ser Gly Asn Gly Ser Tyr Arg Leu Leu Asp His
                85                  90                  95
```

```
tac aag tac ctc acc gct tgg ttc gag ctg ctg aac ctt cca aag aaa      336
Tyr Lys Tyr Leu Thr Ala Trp Phe Glu Leu Leu Asn Leu Pro Lys Lys
            100                 105                 110 atc atc ttt gtg ggc cac gac tgg ggg gct tgt ctg gcc ttt cac tac      384
Ile Ile Phe Val Gly His Asp Trp Gly Ala Cys Leu Ala Phe His Tyr
            115                 120                 125 tcc tac gag cac caa gac aag atc aag gcc atc gtc cat gct gag agt      432
Ser Tyr Glu His Gln Asp Lys Ile Lys Ala Ile Val His Ala Glu Ser
    130                 135                 140 gtc gtg gac gtg atc gag tcc tgg gac gag tgg cct gac atc gag taa      480
Val Val Asp Val Ile Glu Ser Trp Asp Glu Trp Pro Asp Ile Glu
145                 150                 155
```

<210> SEQ ID NO 5
<211> LENGTH: 159
<212> TYPE: PRT
<213> ORGANISM: Artificial
<220> FEATURE:
<223> OTHER INFORMATION: Synthetic Construct

<400> SEQUENCE: 5

```
Ala Ser Lys Val Tyr Asp Pro Glu Gln Arg Lys Arg Met Ile Thr Gly
1               5                   10                  15

Pro Gln Trp Trp Ala Arg Cys Lys Gln Met Asn Val Leu Asp Ser Phe
            20                  25                  30

Ile Asn Tyr Tyr Asp Ser Glu Lys His Ala Glu Asn Ala Val Ile Phe
        35                  40                  45

Leu His Gly Asn Ala Ala Ser Ser Tyr Leu Trp Arg His Val Val Pro
    50                  55                  60

His Ile Glu Pro Val Ala Arg Cys Ile Ile Pro Asp Leu Ile Gly Met
65                  70                  75                  80

Gly Lys Ser Gly Lys Ser Gly Asn Gly Ser Tyr Arg Leu Leu Asp His
                85                  90                  95

Tyr Lys Tyr Leu Thr Ala Trp Phe Glu Leu Leu Asn Leu Pro Lys Lys
            100                 105                 110

Ile Ile Phe Val Gly His Asp Trp Gly Ala Cys Leu Ala Phe His Tyr
        115                 120                 125

Ser Tyr Glu His Gln Asp Lys Ile Lys Ala Ile Val His Ala Glu Ser
    130                 135                 140

Val Val Asp Val Ile Glu Ser Trp Asp Glu Trp Pro Asp Ile Glu
145                 150                 155
```

<210> SEQ ID NO 6
<211> LENGTH: 459
<212> TYPE: DNA
<213> ORGANISM: Artificial
<220> FEATURE:
<223> OTHER INFORMATION: synthetic construct; RLuc(F2)
     an "atg" (or Met) has been added
     at position 1 and a stop codon added at the end of the fragment
<220> FEATURE:
<221> NAME/KEY: CDS
<222> LOCATION: (1)..(459)
<223> OTHER INFORMATION: RLuc(F2) corresponds to a.a. residues
     161-311 of wild-type R.
     Luciferase

<400> SEQUENCE: 6

```
atg gag gat atc gcc ctg atc aag agc gaa gag ggc gag aaa atg gtg       48
Met Glu Asp Ile Ala Leu Ile Lys Ser Glu Glu Gly Glu Lys Met Val
1               5                   10                  15 ctt gag aat aac ttc ttc gtc gag acc atg ctc cca agc aag atc atg      96
```

-continued

```
Leu Glu Asn Asn Phe Phe Val Glu Thr Met Leu Pro Ser Lys Ile Met
            20                  25                  30 cgg aaa ctg gag cct gag gag ttc gct gcc tac ctg gag cca ttc aag      144
Arg Lys Leu Glu Pro Glu Glu Phe Ala Ala Tyr Leu Glu Pro Phe Lys
        35                  40                  45 gag aag ggc gag gtt aga cgg cct acc ctc tcc tgg cct cgc gag atc      192
Glu Lys Gly Glu Val Arg Arg Pro Thr Leu Ser Trp Pro Arg Glu Ile
 50                  55                  60 cct ctc gtt aag gga ggc aag ccc gac gtc gtc cag att gtc cgc aac      240
Pro Leu Val Lys Gly Gly Lys Pro Asp Val Val Gln Ile Val Arg Asn
 65                  70                  75                  80 tac aac gcc tac ctt cgg gcc agc gac gat ctg cct aag atg ttc atc      288
Tyr Asn Ala Tyr Leu Arg Ala Ser Asp Asp Leu Pro Lys Met Phe Ile
                85                  90                  95 gag tcc gac cct ggg ttc ttt tcc aac gct att gtc gag gga gct aag      336
Glu Ser Asp Pro Gly Phe Phe Ser Asn Ala Ile Val Glu Gly Ala Lys
            100                 105                 110 aag ttc cct aac acc gag ttc gtg aag gtg aag ggc ctc cac ttc agc      384
Lys Phe Pro Asn Thr Glu Phe Val Lys Val Lys Gly Leu His Phe Ser
        115                 120                 125 cag gag gac gct cca gat gaa atg ggt aag tac atc aag agc ttc gtg      432
Gln Glu Asp Ala Pro Asp Glu Met Gly Lys Tyr Ile Lys Ser Phe Val
130                 135                 140 gag cgc gtg ctg aag aac gag cag taa                                  459
Glu Arg Val Leu Lys Asn Glu Gln
145                 150
```

```
<210> SEQ ID NO 7
<211> LENGTH: 152
<212> TYPE: PRT
<213> ORGANISM: Artificial
<220> FEATURE:
<223> OTHER INFORMATION: Synthetic Construct

<400> SEQUENCE: 7

Met Glu Asp Ile Ala Leu Ile Lys Ser Glu Glu Gly Glu Lys Met Val
1               5                   10                  15

Leu Glu Asn Asn Phe Phe Val Glu Thr Met Leu Pro Ser Lys Ile Met
            20                  25                  30

Arg Lys Leu Glu Pro Glu Glu Phe Ala Ala Tyr Leu Glu Pro Phe Lys
        35                  40                  45

Glu Lys Gly Glu Val Arg Arg Pro Thr Leu Ser Trp Pro Arg Glu Ile
 50                  55                  60

Pro Leu Val Lys Gly Gly Lys Pro Asp Val Val Gln Ile Val Arg Asn
 65                  70                  75                  80

Tyr Asn Ala Tyr Leu Arg Ala Ser Asp Asp Leu Pro Lys Met Phe Ile
                85                  90                  95

Glu Ser Asp Pro Gly Phe Phe Ser Asn Ala Ile Val Glu Gly Ala Lys
            100                 105                 110

Lys Phe Pro Asn Thr Glu Phe Val Lys Val Lys Gly Leu His Phe Ser
        115                 120                 125

Gln Glu Asp Ala Pro Asp Glu Met Gly Lys Tyr Ile Lys Ser Phe Val
130                 135                 140

Glu Arg Val Leu Lys Asn Glu Gln
145                 150

<210> SEQ ID NO 8
<211> LENGTH: 456
<212> TYPE: DNA
```

<213> ORGANISM: Artificial
<220> FEATURE:
<223> OTHER INFORMATION: synthetic construct; RLuc(F2) with a stop
      codon added at the end
      of the fragment
<220> FEATURE:
<221> NAME/KEY: CDS
<222> LOCATION: (1)..(456)
<223> OTHER INFORMATION: RLuc(F2) corresponds to a.a. residues
      161-311 of wild-type R.
      Luciferase

<400> SEQUENCE: 8

| gag | gat | atc | gcc | ctg | atc | aag | agc | gaa | gag | ggc | gag | aaa | atg | gtg | ctt | 48 |
| Glu | Asp | Ile | Ala | Leu | Ile | Lys | Ser | Glu | Glu | Gly | Glu | Lys | Met | Val | Leu | |
| 1 | | | | 5 | | | | | 10 | | | | | 15 | | |

| gag | aat | aac | ttc | ttc | gtc | gag | acc | atg | ctc | cca | agc | aag | atc | atg | cgg | 96 |
| Glu | Asn | Asn | Phe | Phe | Val | Glu | Thr | Met | Leu | Pro | Ser | Lys | Ile | Met | Arg | |
| | | | 20 | | | | | 25 | | | | | 30 | | | |

| aaa | ctg | gag | cct | gag | gag | ttc | gct | gcc | tac | ctg | gag | cca | ttc | aag | gag | 144 |
| Lys | Leu | Glu | Pro | Glu | Glu | Phe | Ala | Ala | Tyr | Leu | Glu | Pro | Phe | Lys | Glu | |
| | | 35 | | | | | 40 | | | | | 45 | | | | |

| aag | ggc | gag | gtt | aga | cgg | cct | acc | ctc | tcc | tgg | cct | cgc | gag | atc | cct | 192 |
| Lys | Gly | Glu | Val | Arg | Arg | Pro | Thr | Leu | Ser | Trp | Pro | Arg | Glu | Ile | Pro | |
| 50 | | | | | 55 | | | | | 60 | | | | | | |

| ctc | gtt | aag | gga | ggc | aag | ccc | gac | gtc | gtc | cag | att | gtc | cgc | aac | tac | 240 |
| Leu | Val | Lys | Gly | Gly | Lys | Pro | Asp | Val | Val | Gln | Ile | Val | Arg | Asn | Tyr | |
| 65 | | | | 70 | | | | | 75 | | | | | 80 | | |

| aac | gcc | tac | ctt | cgg | gcc | agc | gat | gat | ctg | cct | aag | atg | ttc | atc | gag | 288 |
| Asn | Ala | Tyr | Leu | Arg | Ala | Ser | Asp | Asp | Leu | Pro | Lys | Met | Phe | Ile | Glu | |
| | | | 85 | | | | | 90 | | | | | 95 | | | |

| tcc | gac | cct | ggg | ttc | ttt | tcc | aac | gct | att | gtc | gag | gga | gct | aag | aag | 336 |
| Ser | Asp | Pro | Gly | Phe | Phe | Ser | Asn | Ala | Ile | Val | Glu | Gly | Ala | Lys | Lys | |
| | | 100 | | | | | 105 | | | | | 110 | | | | |

| ttc | cct | aac | acc | gag | ttc | gtg | aag | gtg | aag | ggc | ctc | cac | ttc | agc | cag | 384 |
| Phe | Pro | Asn | Thr | Glu | Phe | Val | Lys | Val | Lys | Gly | Leu | His | Phe | Ser | Gln | |
| | | | 115 | | | | | 120 | | | | | 125 | | | |

| gag | gac | gct | cca | gat | gaa | atg | ggt | aag | tac | atc | aag | agc | ttc | gtg | gag | 432 |
| Glu | Asp | Ala | Pro | Asp | Glu | Met | Gly | Lys | Tyr | Ile | Lys | Ser | Phe | Val | Glu | |
| | 130 | | | | | 135 | | | | | 140 | | | | | |

| cgc | gtg | ctg | aag | aac | gag | cag | taa | | | | | | | | | 456 |
| Arg | Val | Leu | Lys | Asn | Glu | Gln | | | | | | | | | | |
| 145 | | | | 150 | | | | | | | | | | | | |

<210> SEQ ID NO 9
<211> LENGTH: 151
<212> TYPE: PRT
<213> ORGANISM: Artificial
<220> FEATURE:
<223> OTHER INFORMATION: Synthetic Construct

<400> SEQUENCE: 9

Glu Asp Ile Ala Leu Ile Lys Ser Glu Glu Gly Glu Lys Met Val Leu
1               5                   10                  15

Glu Asn Asn Phe Phe Val Glu Thr Met Leu Pro Ser Lys Ile Met Arg
            20                  25                  30

Lys Leu Glu Pro Glu Glu Phe Ala Ala Tyr Leu Glu Pro Phe Lys Glu
        35                  40                  45

Lys Gly Glu Val Arg Arg Pro Thr Leu Ser Trp Pro Arg Glu Ile Pro
    50                  55                  60

Leu Val Lys Gly Gly Lys Pro Asp Val Val Gln Ile Val Arg Asn Tyr
65                  70                  75                  80

```
                Asn Ala Tyr Leu Arg Ala Ser Asp Asp Leu Pro Lys Met Phe Ile Glu
                                85                  90                  95

Ser Asp Pro Gly Phe Ser Asn Ala Ile Val Glu Gly Ala Lys Lys
                            100                 105                 110

Phe Pro Asn Thr Glu Phe Val Lys Val Lys Gly Leu His Phe Ser Gln
                            115                 120                 125

Glu Asp Ala Pro Asp Glu Met Gly Lys Tyr Ile Lys Ser Phe Val Glu
                130                 135                 140

Arg Val Leu Lys Asn Glu Gln
                145                 150

<210> SEQ ID NO 10
<211> LENGTH: 483
<212> TYPE: DNA
<213> ORGANISM: Artificial
<220> FEATURE:
<223> OTHER INFORMATION: synthetic construct; RLuc(F1) with a C124A
      mutation and stop
      codon at end
<220> FEATURE:
<221> NAME/KEY: CDS
<222> LOCATION: (1)..(483)

<400> SEQUENCE: 10 atg gct tcc aag gtg tac gac ccc gag caa cgc aaa cgc atg atc act          48
Met Ala Ser Lys Val Tyr Asp Pro Glu Gln Arg Lys Arg Met Ile Thr
1               5                   10                  15 ggg cct cag tgg tgg gct cgc tgc aag caa atg aac gtg ctg gac tcc          96
Gly Pro Gln Trp Trp Ala Arg Cys Lys Gln Met Asn Val Leu Asp Ser
            20                  25                  30 ttc atc aac tac tat gat tcc gag aag cac gcc gag aac gcc gtg att         144
Phe Ile Asn Tyr Tyr Asp Ser Glu Lys His Ala Glu Asn Ala Val Ile
        35                  40                  45 ttt ctg cat ggt aac gct gcc tcc agc tac ctg tgg agg cac gtc gtg         192
Phe Leu His Gly Asn Ala Ala Ser Ser Tyr Leu Trp Arg His Val Val
    50                  55                  60 cct cac atc gag ccc gtg gct aga tgc atc atc cct gat ctg atc gga         240
Pro His Ile Glu Pro Val Ala Arg Cys Ile Ile Pro Asp Leu Ile Gly
65                  70                  75                  80 atg ggt aag tcc ggc aag agc ggg aat ggc tca tat cgc ctc ctg gat         288
Met Gly Lys Ser Gly Lys Ser Gly Asn Gly Ser Tyr Arg Leu Leu Asp
                85                  90                  95 cac tac aag tac ctc acc gct tgg ttc gag ctg ctg aac ctt cca aag         336
His Tyr Lys Tyr Leu Thr Ala Trp Phe Glu Leu Leu Asn Leu Pro Lys
            100                 105                 110 aaa atc atc ttt gtg ggc cac gac tgg ggg gct gct ctg gcc ttt cac         384
Lys Ile Ile Phe Val Gly His Asp Trp Gly Ala Ala Leu Ala Phe His
        115                 120                 125 tac tcc tac gag cac caa gac aag atc aag gcc atc gtc cat gct gag         432
Tyr Ser Tyr Glu His Gln Asp Lys Ile Lys Ala Ile Val His Ala Glu
    130                 135                 140 agt gtc gtg gac gtg atc gag tcc tgg gac gag tgg cct gac atc gag         480
Ser Val Val Asp Val Ile Glu Ser Trp Asp Glu Trp Pro Asp Ile Glu
145                 150                 155                 160 taa                                                                      483

<210> SEQ ID NO 11
<211> LENGTH: 160
<212> TYPE: PRT
<213> ORGANISM: Artificial
<220> FEATURE:
<223> OTHER INFORMATION: Synthetic Construct
```

<400> SEQUENCE: 11

| Met | Ala | Ser | Lys | Val | Tyr | Asp | Pro | Glu | Gln | Arg | Lys | Arg | Met | Ile | Thr |
|---|---|---|---|---|---|---|---|---|---|---|---|---|---|---|---|
| 1 | | | | 5 | | | | | 10 | | | | | 15 | |

| Gly | Pro | Gln | Trp | Trp | Ala | Arg | Cys | Lys | Gln | Met | Asn | Val | Leu | Asp | Ser |
|---|---|---|---|---|---|---|---|---|---|---|---|---|---|---|---|
| | | | 20 | | | | | 25 | | | | | 30 | | |

| Phe | Ile | Asn | Tyr | Tyr | Asp | Ser | Glu | Lys | His | Ala | Glu | Asn | Ala | Val | Ile |
|---|---|---|---|---|---|---|---|---|---|---|---|---|---|---|---|
| | | | 35 | | | | | 40 | | | | | 45 | | |

| Phe | Leu | His | Gly | Asn | Ala | Ala | Ser | Ser | Tyr | Leu | Trp | Arg | His | Val | Val |
|---|---|---|---|---|---|---|---|---|---|---|---|---|---|---|---|
| | 50 | | | | | 55 | | | | | 60 | | | | |

| Pro | His | Ile | Glu | Pro | Val | Ala | Arg | Cys | Ile | Ile | Pro | Asp | Leu | Ile | Gly |
|---|---|---|---|---|---|---|---|---|---|---|---|---|---|---|---|
| 65 | | | | | 70 | | | | | 75 | | | | | 80 |

| Met | Gly | Lys | Ser | Gly | Lys | Ser | Gly | Asn | Gly | Ser | Tyr | Arg | Leu | Leu | Asp |
|---|---|---|---|---|---|---|---|---|---|---|---|---|---|---|---|
| | | | | 85 | | | | | 90 | | | | | 95 | |

| His | Tyr | Lys | Tyr | Leu | Thr | Ala | Trp | Phe | Glu | Leu | Leu | Asn | Leu | Pro | Lys |
|---|---|---|---|---|---|---|---|---|---|---|---|---|---|---|---|
| | | | 100 | | | | | 105 | | | | | 110 | | |

| Lys | Ile | Ile | Phe | Val | Gly | His | Asp | Trp | Gly | Ala | Ala | Leu | Ala | Phe | His |
|---|---|---|---|---|---|---|---|---|---|---|---|---|---|---|---|
| | | 115 | | | | | 120 | | | | | 125 | | | |

| Tyr | Ser | Tyr | Glu | His | Gln | Asp | Lys | Ile | Lys | Ala | Ile | Val | His | Ala | Glu |
|---|---|---|---|---|---|---|---|---|---|---|---|---|---|---|---|
| | 130 | | | | | 135 | | | | | 140 | | | | |

| Ser | Val | Val | Asp | Val | Ile | Glu | Ser | Trp | Asp | Glu | Trp | Pro | Asp | Ile | Glu |
|---|---|---|---|---|---|---|---|---|---|---|---|---|---|---|---|
| 145 | | | | | 150 | | | | | 155 | | | | | 160 |

<210> SEQ ID NO 12
<211> LENGTH: 480
<212> TYPE: DNA
<213> ORGANISM: Artificial
<220> FEATURE:
<223> OTHER INFORMATION: synthetic construct; RLuc(F1) with C124A
   mutation, initiating
   "atg" removed, and stop codon at end
<220> FEATURE:
<221> NAME/KEY: CDS
<222> LOCATION: (1)..(480)

<400> SEQUENCE: 12

```
gct tcc aag gtg tac gac ccc gag caa cgc aaa cgc atg atc act ggg      48
Ala Ser Lys Val Tyr Asp Pro Glu Gln Arg Lys Arg Met Ile Thr Gly
1               5                  10                  15 cct cag tgg tgg gct cgc tgc aag caa atg aac gtg ctg gac tcc ttc      96
Pro Gln Trp Trp Ala Arg Cys Lys Gln Met Asn Val Leu Asp Ser Phe
            20                  25                  30 atc aac tac tat gat tcc gag aag cac gcc gag aac gcc gtg att ttt     144
Ile Asn Tyr Tyr Asp Ser Glu Lys His Ala Glu Asn Ala Val Ile Phe
        35                  40                  45 ctg cat ggt aac gct gcc tcc agc tac ctg tgg agg cac gtc gtg cct     192
Leu His Gly Asn Ala Ala Ser Ser Tyr Leu Trp Arg His Val Val Pro
    50                  55                  60 cac atc gag ccc gtg gct aga tgc atc atc cct gat ctg atc gga atg     240
His Ile Glu Pro Val Ala Arg Cys Ile Ile Pro Asp Leu Ile Gly Met
65                  70                  75                  80 ggt aag tcc ggc aag agc ggg aat ggc tca tat cgc ctc ctg gat cac     288
Gly Lys Ser Gly Lys Ser Gly Asn Gly Ser Tyr Arg Leu Leu Asp His
                85                  90                  95 tac aag tac ctc acc gct tgg ttc gag ctg ctg aac ctt cca aag aaa     336
Tyr Lys Tyr Leu Thr Ala Trp Phe Glu Leu Leu Asn Leu Pro Lys Lys
            100                 105                 110 atc atc ttt gtg ggc cac gac tgg ggg gct gct ctg gcc ttt cac tac     384
Ile Ile Phe Val Gly His Asp Trp Gly Ala Ala Leu Ala Phe His Tyr
        115                 120                 125
```

```
tcc tac gag cac caa gac aag atc aag gcc atc gtc cat gct gag agt     432
Ser Tyr Glu His Gln Asp Lys Ile Lys Ala Ile Val His Ala Glu Ser
    130                 135                 140 gtc gtg gac gtg atc gag tcc tgg gac gag tgg cct gac atc gag taa     480
Val Val Asp Val Ile Glu Ser Trp Asp Glu Trp Pro Asp Ile Glu
145                 150                 155

<210> SEQ ID NO 13
<211> LENGTH: 159
<212> TYPE: PRT
<213> ORGANISM: Artificial
<220> FEATURE:
<223> OTHER INFORMATION: Synthetic Construct

<400> SEQUENCE: 13

Ala Ser Lys Val Tyr Asp Pro Glu Gln Arg Lys Arg Met Ile Thr Gly
1               5                   10                  15

Pro Gln Trp Trp Ala Arg Cys Lys Gln Met Asn Val Leu Asp Ser Phe
            20                  25                  30

Ile Asn Tyr Tyr Asp Ser Glu Lys His Ala Glu Asn Ala Val Ile Phe
        35                  40                  45

Leu His Gly Asn Ala Ala Ser Ser Tyr Leu Trp Arg His Val Val Pro
    50                  55                  60

His Ile Glu Pro Val Ala Arg Cys Ile Ile Pro Asp Leu Ile Gly Met
65                  70                  75                  80

Gly Lys Ser Gly Lys Ser Gly Asn Gly Ser Tyr Arg Leu Leu Asp His
                85                  90                  95

Tyr Lys Tyr Leu Thr Ala Trp Phe Glu Leu Leu Asn Leu Pro Lys Lys
            100                 105                 110

Ile Ile Phe Val Gly His Asp Trp Gly Ala Ala Leu Ala Phe His Tyr
        115                 120                 125

Ser Tyr Glu His Gln Asp Lys Ile Lys Ala Ile Val His Ala Glu Ser
    130                 135                 140

Val Val Asp Val Ile Glu Ser Trp Asp Glu Trp Pro Asp Ile Glu
145                 150                 155

<210> SEQ ID NO 14
<211> LENGTH: 477
<212> TYPE: DNA
<213> ORGANISM: Artificial
<220> FEATURE:
<223> OTHER INFORMATION: synthetic construct; YFP(F1) with added stop
      codon at end
<220> FEATURE:
<221> NAME/KEY: CDS
<222> LOCATION: (1)..(477)
<223> OTHER INFORMATION: YFP(F1) corresponds to a.a. 1-158 of the full
      length EYFP

<400> SEQUENCE: 14 atg gtg agc aag ggc gag gag ctg ttc acc ggg gtg gtg ccc atc ctg      48
Met Val Ser Lys Gly Glu Glu Leu Phe Thr Gly Val Val Pro Ile Leu
1               5                   10                  15 gtc gag ctg gac ggc gac gta aac ggc cac aag ttc agc gtg tcc ggc      96
Val Glu Leu Asp Gly Asp Val Asn Gly His Lys Phe Ser Val Ser Gly
            20                  25                  30 gag ggc gag ggc gat gcc acc tac ggc aag ctg acc ctg aag ttc atc     144
Glu Gly Glu Gly Asp Ala Thr Tyr Gly Lys Leu Thr Leu Lys Phe Ile
        35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
```

```
                    50                  55                  60
ttc ggc tac ggc ctg cag tgc ttc gcc cgc tac ccc gac cac atg aag    240
Phe Gly Tyr Gly Leu Gln Cys Phe Ala Arg Tyr Pro Asp His Met Lys
 65                  70                  75                  80 cag cac gac ttc ttc aag tcc gcc atg ccc gaa ggc tac gtc cag gag    288
Gln His Asp Phe Phe Lys Ser Ala Met Pro Glu Gly Tyr Val Gln Glu
                     85                  90                  95 cgc acc atc ttc ttc aag gac gac ggc aac tac aag acc cgc gcc gag    336
Arg Thr Ile Phe Phe Lys Asp Asp Gly Asn Tyr Lys Thr Arg Ala Glu
                100                 105                 110 gtg aag ttc gag ggc gac acc ctg gtg aac cgc atc gag ctg aag ggc    384
Val Lys Phe Glu Gly Asp Thr Leu Val Asn Arg Ile Glu Leu Lys Gly
            115                 120                 125 atc gac ttc aag gag gac ggc aac atc ctg ggg cac aag ctg gag tac    432
Ile Asp Phe Lys Glu Asp Gly Asn Ile Leu Gly His Lys Leu Glu Tyr
        130                 135                 140 aac tac aac agc cac aac gtc tat atc atg gcc gac aag cag taa        477
Asn Tyr Asn Ser His Asn Val Tyr Ile Met Ala Asp Lys Gln
145                 150                 155

<210> SEQ ID NO 15
<211> LENGTH: 158
<212> TYPE: PRT
<213> ORGANISM: Artificial
<220> FEATURE:
<223> OTHER INFORMATION: Synthetic Construct

<400> SEQUENCE: 15

Met Val Ser Lys Gly Glu Glu Leu Phe Thr Gly Val Val Pro Ile Leu
  1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Phe Ile
         35                  40                  45

Cys Thr Thr Gly Lys Leu Pro Val Pro Trp Pro Thr Leu Val Thr Thr
     50                  55                  60

Phe Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln
145                 150                 155

<210> SEQ ID NO 16
<211> LENGTH: 474
<212> TYPE: DNA
<213> ORGANISM: Artificial
<220> FEATURE:
<223> OTHER INFORMATION: synthetic construct; YFP(F1) with stop codon
      added at end and
      initial "atg" (or Met) removed
<220> FEATURE:
<221> NAME/KEY: CDS
<222> LOCATION: (1)..(474)
<223> OTHER INFORMATION: YFP(F1) corresponds to a.a. 1-158 of the full
``` length EYFP

<400> SEQUENCE: 16

```
gtg agc aag ggc gag gag ctg ttc acc ggg gtg gtg ccc atc ctg gtc      48
Val Ser Lys Gly Glu Glu Leu Phe Thr Gly Val Val Pro Ile Leu Val
1               5                   10                  15 gag ctg gac ggc gac gta aac ggc cac aag ttc agc gtg tcc ggc gag      96
Glu Leu Asp Gly Asp Val Asn Gly His Lys Phe Ser Val Ser Gly Glu
            20                  25                  30 ggc gag ggc gat gcc acc tac ggc aag ctg acc ctg aag ttc atc tgc     144
Gly Glu Gly Asp Ala Thr Tyr Gly Lys Leu Thr Leu Lys Phe Ile Cys
        35                  40                  45 acc acc ggc aag ctg ccc gtg ccc tgg ccc acc ctc gtg acc acc ttc     192
Thr Thr Gly Lys Leu Pro Val Pro Trp Pro Thr Leu Val Thr Thr Phe
50                  55                  60 ggc tac ggc ctg cag tgc ttc gcc cgc tac ccc gac cac atg aag cag     240
Gly Tyr Gly Leu Gln Cys Phe Ala Arg Tyr Pro Asp His Met Lys Gln
65                  70                  75                  80 cac gac ttc ttc aag tcc gcc atg ccc gaa ggc tac gtc cag gag cgc     288
His Asp Phe Phe Lys Ser Ala Met Pro Glu Gly Tyr Val Gln Glu Arg
                85                  90                  95 acc atc ttc ttc aag gac gac ggc aac tac aag acc cgc gcc gag gtg     336
Thr Ile Phe Phe Lys Asp Asp Gly Asn Tyr Lys Thr Arg Ala Glu Val
            100                 105                 110 aag ttc gag ggc gac acc ctg gtg aac cgc atc gag ctg aag ggc atc     384
Lys Phe Glu Gly Asp Thr Leu Val Asn Arg Ile Glu Leu Lys Gly Ile
        115                 120                 125 gac ttc aag gag gac ggc aac atc ctg ggg cac aag ctg gag tac aac     432
Asp Phe Lys Glu Asp Gly Asn Ile Leu Gly His Lys Leu Glu Tyr Asn
    130                 135                 140 tac aac agc cac aac gtc tat atc atg gcc gac aag cag taa             474
Tyr Asn Ser His Asn Val Tyr Ile Met Ala Asp Lys Gln
145                 150                 155
```

<210> SEQ ID NO 17
<211> LENGTH: 157
<212> TYPE: PRT
<213> ORGANISM: Artificial
<220> FEATURE:
<223> OTHER INFORMATION: Synthetic Construct

<400> SEQUENCE: 17

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
```

```
                130              135             140
Tyr Asn Ser His Asn Val Tyr Ile Met Ala Asp Lys Gln
145                 150                 155

<210> SEQ ID NO 18
<211> LENGTH: 249
<212> TYPE: DNA
<213> ORGANISM: Artificial
<220> FEATURE:
<223> OTHER INFORMATION: synthetic construct; YFP(F2) with added
      "atg" (or Met) at
      position 1 and stop codon at end
<220> FEATURE:
<221> NAME/KEY: CDS
<222> LOCATION: (1)..(249)
<223> OTHER INFORMATION: YFP(F2) corresponds to a.a. 159-239 of the
      full length EYFP

<400> SEQUENCE: 18 atg aag aac ggc atc aag gtg aac ttc aag atc cgc cac aac atc gag    48
Met Lys Asn Gly Ile Lys Val Asn Phe Lys Ile Arg His Asn Ile Glu
 1               5                  10                  15 gac ggc agc gtg cag ctc gcc gac cac tac cag cag aac acc ccc atc    96
Asp Gly Ser Val Gln Leu Ala Asp His Tyr Gln Gln Asn Thr Pro Ile
             20                  25                  30 ggc gac ggc ccc gtg ctg ctg ccc gac aac cac tac ctg agc tac cag   144
Gly Asp Gly Pro Val Leu Leu Pro Asp Asn His Tyr Leu Ser Tyr Gln
         35                  40                  45 tcc gcc ctg agc aaa gac ccc aac gag aag cgc gat cac atg gtc ctg   192
Ser Ala Leu Ser Lys Asp Pro Asn Glu Lys Arg Asp His Met Val Leu
     50                  55                  60 ctg gag ttc gtg acc gcc gcc ggg atc act ctc ggc atg gac gag ctg   240
Leu Glu Phe Val Thr Ala Ala Gly Ile Thr Leu Gly Met Asp Glu Leu
 65                  70                  75                  80 tac aag taa                                                       249
Tyr Lys

<210> SEQ ID NO 19
<211> LENGTH: 82
<212> TYPE: PRT
<213> ORGANISM: Artificial
<220> FEATURE:
<223> OTHER INFORMATION: Synthetic Construct

<400> SEQUENCE: 19

Met Lys Asn Gly Ile Lys Val Asn Phe Lys Ile Arg His Asn Ile Glu
 1               5                  10                  15

Asp Gly Ser Val Gln Leu Ala Asp His Tyr Gln Gln Asn Thr Pro Ile
             20                  25                  30

Gly Asp Gly Pro Val Leu Leu Pro Asp Asn His Tyr Leu Ser Tyr Gln
         35                  40                  45

Ser Ala Leu Ser Lys Asp Pro Asn Glu Lys Arg Asp His Met Val Leu
     50                  55                  60

Leu Glu Phe Val Thr Ala Ala Gly Ile Thr Leu Gly Met Asp Glu Leu
 65                  70                  75                  80

Tyr Lys

<210> SEQ ID NO 20
<211> LENGTH: 246
<212> TYPE: DNA
<213> ORGANISM: Artificial
<220> FEATURE:
<223> OTHER INFORMATION: synthetic construct; YFP(F2) with added
```

```
                        stop codon at end
<220> FEATURE:
<221> NAME/KEY: CDS
<222> LOCATION: (1)..(246)
<223> OTHER INFORMATION: YFP(F2) corresponds to a.a. 159-239 of the
      full length EYFP

<400> SEQUENCE: 20 aag aac ggc atc aag gtg aac ttc aag atc cgc cac aac atc gag gac        48
Lys Asn Gly Ile Lys Val Asn Phe Lys Ile Arg His Asn Ile Glu Asp
 1               5                  10                  15 ggc agc gtg cag ctc gcc gac cac tac cag cag aac acc ccc atc ggc        96
Gly Ser Val Gln Leu Ala Asp His Tyr Gln Gln Asn Thr Pro Ile Gly
             20                  25                  30 gac ggc ccc gtg ctg ctg ccc gac aac cac tac ctg agc tac cag tcc       144
Asp Gly Pro Val Leu Leu Pro Asp Asn His Tyr Leu Ser Tyr Gln Ser
         35                  40                  45 gcc ctg agc aaa gac ccc aac gag aag cgc gat cac atg gtc ctg ctg       192
Ala Leu Ser Lys Asp Pro Asn Glu Lys Arg Asp His Met Val Leu Leu
     50                  55                  60 gag ttc gtg acc gcc gcc ggg atc act ctc ggc atg gac gag ctg tac       240
Glu Phe Val Thr Ala Ala Gly Ile Thr Leu Gly Met Asp Glu Leu Tyr
 65                  70                  75                  80 aag taa                                                                246
Lys

<210> SEQ ID NO 21
<211> LENGTH: 81
<212> TYPE: PRT
<213> ORGANISM: Artificial
<220> FEATURE:
<223> OTHER INFORMATION: Synthetic Construct

<400> SEQUENCE: 21

Lys Asn Gly Ile Lys Val Asn Phe Lys Ile Arg His Asn Ile Glu Asp
 1               5                  10                  15

Gly Ser Val Gln Leu Ala Asp His Tyr Gln Gln Asn Thr Pro Ile Gly
             20                  25                  30

Asp Gly Pro Val Leu Leu Pro Asp Asn His Tyr Leu Ser Tyr Gln Ser
         35                  40                  45

Ala Leu Ser Lys Asp Pro Asn Glu Lys Arg Asp His Met Val Leu Leu
     50                  55                  60

Glu Phe Val Thr Ala Ala Gly Ile Thr Leu Gly Met Asp Glu Leu Tyr
 65                  70                  75                  80

Lys

<210> SEQ ID NO 22
<211> LENGTH: 477
<212> TYPE: DNA
<213> ORGANISM: Artificial
<220> FEATURE:
<223> OTHER INFORMATION: synthetic construct; IFP(F1) with stop codon
      added at end
<220> FEATURE:
<221> NAME/KEY: CDS
<222> LOCATION: (1)..(477)
<223> OTHER INFORMATION: IFP(F1)  corresponds to a F46L mutated form of
      SEYFP(F1)

<400> SEQUENCE: 22 atg gtg agc aag ggc gag gag ctg ttc acc ggg gtg gtg ccc atc ctg        48
Met Val Ser Lys Gly Glu Glu Leu Phe Thr Gly Val Val Pro Ile Leu
 1               5                  10                  15
```

```
gtc gag ctg gac ggc gac gta aac ggc cac aag ttc agc gtg tcc ggc      96
Val Glu Leu Asp Gly Asp Val Asn Gly His Lys Phe Ser Val Ser Gly
         20                  25                  30 gag ggc gag ggc gat gcc acc tac ggc aag ctg acc ctg aag ttg atc     144
Glu Gly Glu Gly Asp Ala Thr Tyr Gly Lys Leu Thr Leu Lys Leu Ile
     35                  40                  45 tgc acc acc ggc aag ctg ccc gtg ccc tgg ccc acc ctc gtg acc acc     192
Cys Thr Thr Gly Lys Leu Pro Val Pro Trp Pro Thr Leu Val Thr Thr
 50                  55                  60 ctc ggc tac ggc ctg cag tgc ttc gcc cgc tac ccc gac cac atg aag     240
Leu Gly Tyr Gly Leu Gln Cys Phe Ala Arg Tyr Pro Asp His Met Lys
 65                  70                  75                  80 cag cac gac ttc ttc aag tcc gcc atg ccc gaa ggc tac gtc cag gag     288
Gln His Asp Phe Phe Lys Ser Ala Met Pro Glu Gly Tyr Val Gln Glu
                 85                  90                  95 cgc acc atc ttc ttc aag gac gac ggc aac tac aag acc cgc gcc gag     336
Arg Thr Ile Phe Phe Lys Asp Asp Gly Asn Tyr Lys Thr Arg Ala Glu
             100                 105                 110 gtg aag ttc gag ggc gac acc ctg gtg aac cgc atc gag ctg aag ggc     384
Val Lys Phe Glu Gly Asp Thr Leu Val Asn Arg Ile Glu Leu Lys Gly
         115                 120                 125 atc gac ttc aag gag gac ggc aac atc ctg ggg cac aag ctg gag tac     432
Ile Asp Phe Lys Glu Asp Gly Asn Ile Leu Gly His Lys Leu Glu Tyr
130                 135                 140 aac tac aac agc cac aac gtc tat atc acg gcc gac aag cag taa        477
Asn Tyr Asn Ser His Asn Val Tyr Ile Thr Ala Asp Lys Gln
145                 150                 155
```

<210> SEQ ID NO 23
<211> LENGTH: 158
<212> TYPE: PRT
<213> ORGANISM: Artificial
<220> FEATURE:
<223> OTHER INFORMATION: Synthetic Construct

<400> SEQUENCE: 23

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
             20                  25                  30

Glu Gly Glu Gly Asp Ala Thr Tyr Gly Lys Leu Thr Leu Lys Leu Ile
         35                  40                  45

Cys Thr Thr Gly Lys Leu Pro Val Pro Trp Pro Thr Leu Val Thr Thr
     50                  55                  60

Leu Gly Tyr Gly Leu Gln Cys Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Thr Ala Asp Lys Gln
145                 150                 155
```

<210> SEQ ID NO 24
<211> LENGTH: 474

<212> TYPE: DNA
<213> ORGANISM: Artificial
<220> FEATURE:
<223> OTHER INFORMATION: synthetic construct; IFP(F1) with initiating
      "atg" (or Met)
      removed and stop codon added at end
<220> FEATURE:
<221> NAME/KEY: CDS
<222> LOCATION: (1)..(474)
<223> OTHER INFORMATION: IFP(F1) corresponds to a F46L mutated form
      of SEYFP(F1)

<400> SEQUENCE: 24

```
gtg agc aag ggc gag gag ctg ttc acc ggg gtg gtg ccc atc ctg gtc      48
Val Ser Lys Gly Glu Glu Leu Phe Thr Gly Val Val Pro Ile Leu Val
1               5                   10                  15 gag ctg gac ggc gac gta aac ggc cac aag ttc agc gtg tcc ggc gag      96
Glu Leu Asp Gly Asp Val Asn Gly His Lys Phe Ser Val Ser Gly Glu
            20                  25                  30 ggc gag ggc gat gcc acc tac ggc aag ctg acc ctg aag ttg atc tgc     144
Gly Glu Gly Asp Ala Thr Tyr Gly Lys Leu Thr Leu Lys Leu Ile Cys
        35                  40                  45 acc acc ggc aag ctg ccc gtg ccc tgg ccc acc ctc gtg acc acc ctc     192
Thr Thr Gly Lys Leu Pro Val Pro Trp Pro Thr Leu Val Thr Thr Leu
50                  55                  60 ggc tac ggc ctg cag tgc ttc gcc cgc tac ccc gac cac atg aag cag     240
Gly Tyr Gly Leu Gln Cys Phe Ala Arg Tyr Pro Asp His Met Lys Gln
65                  70                  75                  80 cac gac ttc ttc aag tcc gcc atg ccc gaa ggc tac gtc cag gag cgc     288
His Asp Phe Phe Lys Ser Ala Met Pro Glu Gly Tyr Val Gln Glu Arg
                85                  90                  95 acc atc ttc ttc aag gac gac ggc aac tac aag acc cgc gcc gag gtg     336
Thr Ile Phe Phe Lys Asp Asp Gly Asn Tyr Lys Thr Arg Ala Glu Val
            100                 105                 110 aag ttc gag ggc gac acc ctg gtg aac cgc atc gag ctg aag ggc atc     384
Lys Phe Glu Gly Asp Thr Leu Val Asn Arg Ile Glu Leu Lys Gly Ile
        115                 120                 125 gac ttc aag gag gac ggc aac atc ctg ggg cac aag ctg gag tac aac     432
Asp Phe Lys Glu Asp Gly Asn Ile Leu Gly His Lys Leu Glu Tyr Asn
130                 135                 140 tac aac agc cac aac gtc tat atc acg gcc gac aag cag taa             474
Tyr Asn Ser His Asn Val Tyr Ile Thr Ala Asp Lys Gln
145                 150                 155
```

<210> SEQ ID NO 25
<211> LENGTH: 157
<212> TYPE: PRT
<213> ORGANISM: Artificial
<220> FEATURE:
<223> OTHER INFORMATION: Synthetic Construct

<400> SEQUENCE: 25

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Leu Ile Cys
        35                  40                  45

Thr Thr Gly Lys Leu Pro Val Pro Trp Pro Thr Leu Val Thr Thr Leu
50                  55                  60

Gly Tyr Gly Leu Gln Cys Phe Ala Arg Tyr Pro Asp His Met Lys Gln
65                  70                  75                  80
```

```
                             His Asp Phe Phe Lys Ser Ala Met Pro Glu Gly Tyr Val Gln Glu Arg
                                             85                  90                  95

Thr Ile Phe Phe Lys Asp Asp Gly Asn Tyr Lys Thr Arg Ala Glu Val
                                             100                 105                 110

Lys Phe Glu Gly Asp Thr Leu Val Asn Arg Ile Glu Leu Lys Gly Ile
                                             115                 120                 125

Asp Phe Lys Glu Asp Gly Asn Ile Leu Gly His Lys Leu Glu Tyr Asn
                                             130                 135                 140

Tyr Asn Ser His Asn Val Tyr Ile Thr Ala Asp Lys Gln
                             145                 150                 155

<210> SEQ ID NO 26
<211> LENGTH: 249
<212> TYPE: DNA
<213> ORGANISM: Artificial
<220> FEATURE:
<223> OTHER INFORMATION: synthetic construct; IFP(F2) with added
      "atg" (or Met) at
      position 1 and a stop codon at the end
<220> FEATURE:
<221> NAME/KEY: CDS
<222> LOCATION: (1)..(249)
<223> OTHER INFORMATION: IFP(F2) corresponds to a V163A, S175G mutated
      form of YFP(F2)

<400> SEQUENCE: 26 atg aag aac ggc atc aag gcg aac ttc aag atc cgc cac aac atc gag      48
Met Lys Asn Gly Ile Lys Ala Asn Phe Lys Ile Arg His Asn Ile Glu
1               5                   10                  15 gac ggc ggc gtg cag ctc gcc gac cac tac cag cag aac acc ccc atc      96
Asp Gly Gly Val Gln Leu Ala Asp His Tyr Gln Gln Asn Thr Pro Ile
                20                  25                  30 ggc gac ggc ccc gtg ctg ctg ccc gac aac cac tac ctg agc tac cag     144
Gly Asp Gly Pro Val Leu Leu Pro Asp Asn His Tyr Leu Ser Tyr Gln
            35                  40                  45 tcc gcc ctg agc aaa gac ccc aac gag aag cgc gat cac atg gtc ctg     192
Ser Ala Leu Ser Lys Asp Pro Asn Glu Lys Arg Asp His Met Val Leu
        50                  55                  60 ctg gag ttc gtg acc gcc gcc ggg atc act ctc ggc atg gac gag ctg     240
Leu Glu Phe Val Thr Ala Ala Gly Ile Thr Leu Gly Met Asp Glu Leu
65                  70                  75                  80 tac aag taa                                                         249
Tyr Lys

<210> SEQ ID NO 27
<211> LENGTH: 82
<212> TYPE: PRT
<213> ORGANISM: Artificial
<220> FEATURE:
<223> OTHER INFORMATION: Synthetic Construct

<400> SEQUENCE: 27

Met Lys Asn Gly Ile Lys Ala Asn Phe Lys Ile Arg His Asn Ile Glu
1               5                   10                  15

Asp Gly Gly Val Gln Leu Ala Asp His Tyr Gln Gln Asn Thr Pro Ile
                20                  25                  30

Gly Asp Gly Pro Val Leu Leu Pro Asp Asn His Tyr Leu Ser Tyr Gln
            35                  40                  45

Ser Ala Leu Ser Lys Asp Pro Asn Glu Lys Arg Asp His Met Val Leu
        50                  55                  60

Leu Glu Phe Val Thr Ala Ala Gly Ile Thr Leu Gly Met Asp Glu Leu
65                  70                  75                  80
```

Tyr Lys

<210> SEQ ID NO 28
<211> LENGTH: 246
<212> TYPE: DNA
<213> ORGANISM: Artificial
<220> FEATURE:
<223> OTHER INFORMATION: synthetic construct; IFP(F2)  with an added
      stop codon at the end
<220> FEATURE:
<221> NAME/KEY: CDS
<222> LOCATION: (1)..(246)
<223> OTHER INFORMATION: IFP(F2) corresponds to a V163A, S175G mutated
      form of YFP(F2)

<400> SEQUENCE: 28

```
aag aac ggc atc aag gcg aac ttc aag atc cgc cac aac atc gag gac      48
Lys Asn Gly Ile Lys Ala Asn Phe Lys Ile Arg His Asn Ile Glu Asp
1               5                   10                  15 ggc ggc gtg cag ctc gcc gac cac tac cag cag aac acc ccc atc ggc      96
Gly Gly Val Gln Leu Ala Asp His Tyr Gln Gln Asn Thr Pro Ile Gly
            20                  25                  30 gac ggc ccc gtg ctg ctg ccc gac aac cac tac ctg agc tac cag tcc     144
Asp Gly Pro Val Leu Leu Pro Asp Asn His Tyr Leu Ser Tyr Gln Ser
        35                  40                  45 gcc ctg agc aaa gac ccc aac gag aag cgc gat cac atg gtc ctg ctg     192
Ala Leu Ser Lys Asp Pro Asn Glu Lys Arg Asp His Met Val Leu Leu
    50                  55                  60 gag ttc gtg acc gcc gcc ggg atc act ctc ggc atg gac gag ctg tac     240
Glu Phe Val Thr Ala Ala Gly Ile Thr Leu Gly Met Asp Glu Leu Tyr
65                  70                  75                  80 aag taa                                                              246
Lys
```

<210> SEQ ID NO 29
<211> LENGTH: 81
<212> TYPE: PRT
<213> ORGANISM: Artificial
<220> FEATURE:
<223> OTHER INFORMATION: Synthetic Construct

<400> SEQUENCE: 29

Lys Asn Gly Ile Lys Ala Asn Phe Lys Ile Arg His Asn Ile Glu Asp
1               5                   10                  15

Gly Gly Val Gln Leu Ala Asp His Tyr Gln Gln Asn Thr Pro Ile Gly
            20                  25                  30

Asp Gly Pro Val Leu Leu Pro Asp Asn His Tyr Leu Ser Tyr Gln Ser
        35                  40                  45

Ala Leu Ser Lys Asp Pro Asn Glu Lys Arg Asp His Met Val Leu Leu
    50                  55                  60

Glu Phe Val Thr Ala Ala Gly Ile Thr Leu Gly Met Asp Glu Leu Tyr
65                  70                  75                  80

Lys

<210> SEQ ID NO 30
<211> LENGTH: 15
<212> TYPE: PRT
<213> ORGANISM: Artificial
<220> FEATURE:
<223> OTHER INFORMATION: synthetic construct, a flexible linker

<400> SEQUENCE: 30

-continued

```
Gly Gly Gly Gly Ser Gly Gly Gly Gly Ser Gly Gly Gly Gly Ser
1               5                   10                  15

<210> SEQ ID NO 31
<211> LENGTH: 5
<212> TYPE: PRT
<213> ORGANISM: Artificial
<220> FEATURE:
<223> OTHER INFORMATION: synthetic construct, "5-mer" building block
      for flexible linkers

<400> SEQUENCE: 31

Gly Gly Gly Gly Ser
1               5
```